(12) United States Patent
Remelius

(10) Patent No.: US 11,585,931 B2
(45) Date of Patent: Feb. 21, 2023

(54) LIGHT DIRECTION DETECTOR SYSTEMS AND METHODS

(71) Applicant: Jebb Remelius, Pittsfiled, MA (US)

(72) Inventor: Jebb Remelius, Pittsfiled, MA (US)

( * ) Notice: Subject to any disclaimer, the term of this patent is extended or adjusted under 35 U.S.C. 154(b) by 0 days.

(21) Appl. No.: 17/496,369

(22) Filed: Oct. 7, 2021

(65) Prior Publication Data
US 2022/0107415 A1 Apr. 7, 2022

Related U.S. Application Data

(60) Provisional application No. 63/191,343, filed on May 21, 2021, provisional application No. 63/088,769, filed on Oct. 7, 2020.

(51) Int. Cl.
*G01S 17/66* (2006.01)
*G01S 17/42* (2006.01)
*G01S 17/86* (2020.01)
*G01S 7/4863* (2020.01)
*A61B 5/11* (2006.01)

(52) U.S. Cl.
CPC ............ *G01S 17/66* (2013.01); *G01S 7/4863* (2013.01); *G01S 17/42* (2013.01); *G01S 17/86* (2020.01); *A61B 5/1114* (2013.01)

(58) Field of Classification Search
CPC ........ G01S 17/66; G01S 7/4863; G01S 17/42; G01S 17/86; G01S 3/784; G01S 5/163; A61B 5/1114; A61B 5/1128; A61B 5/0077; A61B 5/1122; A61B 5/6826; A61B 5/6803
See application file for complete search history.

(56) References Cited

U.S. PATENT DOCUMENTS

2018/0329024 A1* 11/2018 Send .................. G01S 17/46
2020/0146790 A1* 5/2020 Marshall ............. A61B 5/0088

* cited by examiner

*Primary Examiner* — Seung C Sohn
(74) *Attorney, Agent, or Firm* — DLA Piper LLP US

(57) ABSTRACT

Intensity of a light from a light array comprising a plurality of light sources configured to illuminate in sequence may be detected at two optically isolated points of a motion tracker device. The optically isolated points may be disposed at a distance from one another such that a variation in intensity of light due to shadowing effects from the plurality of light sources is different at the optically isolated points. The optically isolated points may be separated by a T-shaped wall. The motion tracker device may generate a current signal representing a photodiode differential between the two optically isolated points and proportional to the intensity of the light. The current signal may be used for sensor fusion with an inertial measurement unit.

20 Claims, 36 Drawing Sheets

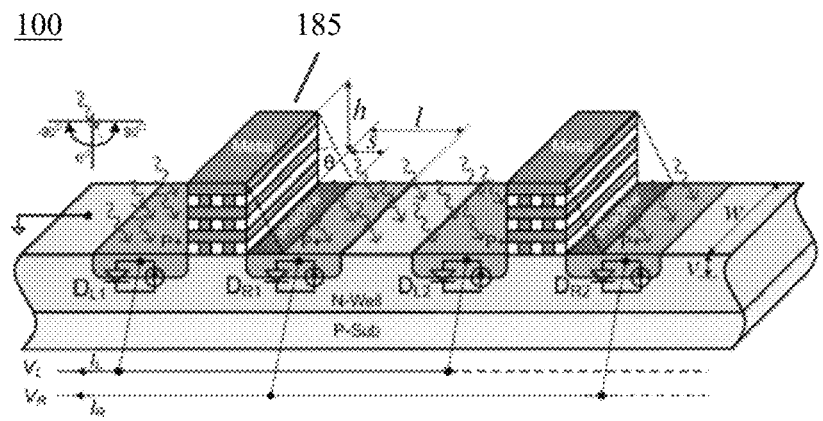
FIG. 1A　　　　　　　PRIOR ART
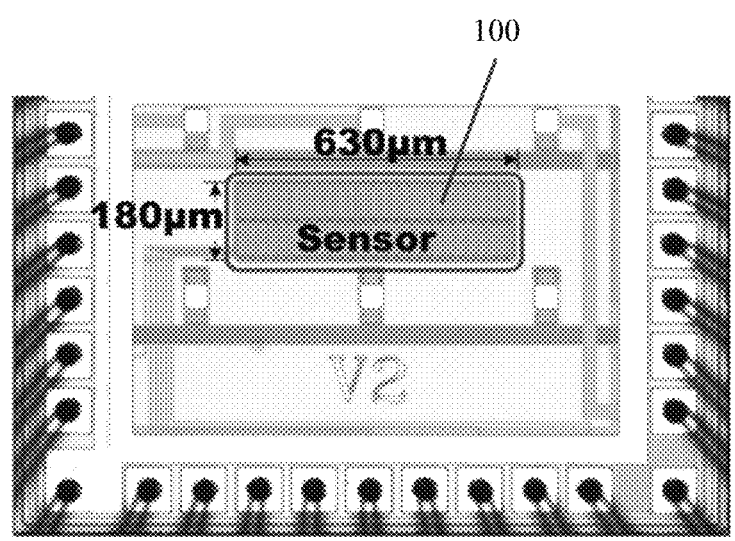
FIG. 1B　　　　　　　PRIOR ART

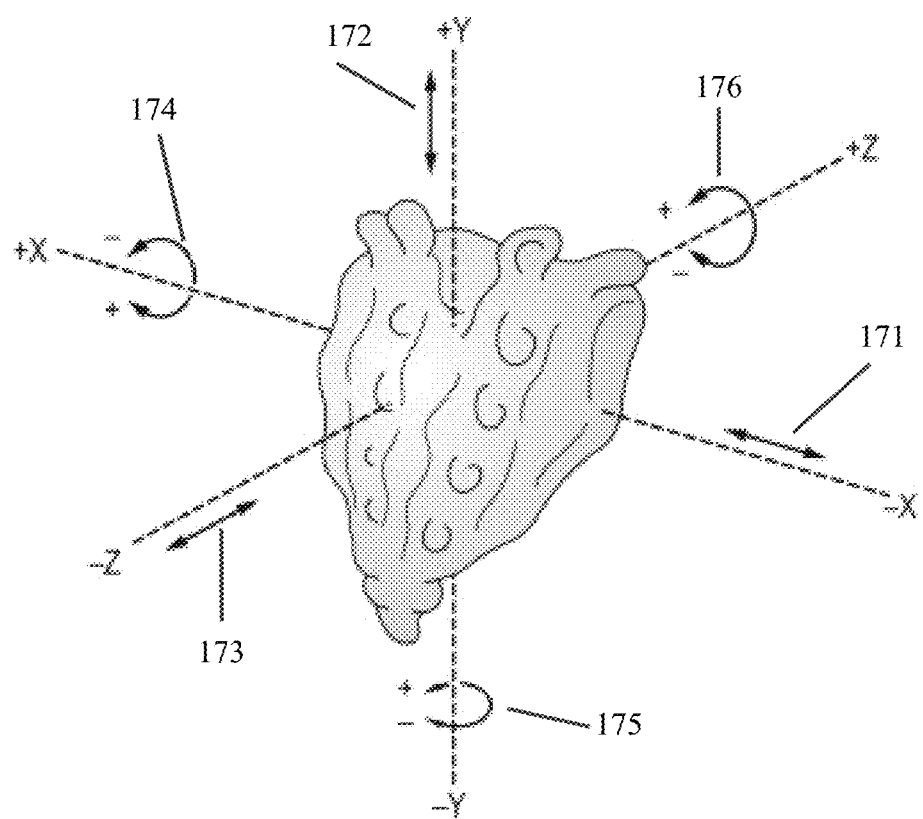
FIG. 1C            PRIOR ART

Automated serial IRED powering (yellow lines) to build a self-calibrating Surf6 volume (left); Outside-in serial Surf6 tracking (center); Inside-out serial Surf6 tracking (right). Surf6 devices NTS.

2100

2100

2200     Make topmost sacrificial layer shaped so next sputtered metal layer deposition leaves last layer cantilevered above photodiodes on either side of wall, then etch framework away

2210

2220

2200     Sputtered metal layer deposition inside photoresist layer

2210

2220

LIGHT DIRECTION DETECTOR SYSTEMS AND METHODS

CROSS-REFERENCE TO RELATED APPLICATIONS

This application claims priority from U.S. Provisional Application No. 63/088,769, entitled "Light Direction Detector Systems and Methods," filed Oct. 7, 2020 and U.S. Provisional Application No. 63/191,343, entitled "Light Direction Detector Systems and Methods," filed May 21, 2021, the entirety of each of which is incorporated by reference herein. This application also incorporates U.S. Provisional Application No. 62/630,364, filed Feb. 14, 2018, and U.S. patent application Ser. No. 16/276,152, filed Feb. 14, 2019, by reference in their entireties.

FIELD OF DISCLOSURE

This disclosure relates generally to motion-capture technology, and, more particularly, to a system for capturing, tracking and analyzing motion in six dimensions without the use of cameras.

BACKGROUND

Existing motion-capture systems may detect infrared (IR) signals with expensive digital cameras having one or more lenses. The IR signals may be emitted from active markers or a ring of light-emitting diodes (LEDs) surrounding each lens which cause light to be bounced off of retro-reflective passive markers affixed to the object being tracked. These motion-capture systems may require at least three cameras to be effective. Some systems operate with more than six cameras, and some systems are scaled up to even 300 cameras.

However, currently available motion-capture systems may only record three-dimensional (3D) positions of single points, describing an object's motion in left-to-right, up-and-down or forward-and-backward. Data with six degrees of freedom (6DoF), including rotational movement about the x-, y- and z-axes, is often highly valuable for body position analysis in medicine, in virtual reality mechanics, and in reality-based animation, among other applications. In order to approximate 6 degrees of freedom, a motion-capture technician may currently need to apply and track three or more passive markers to get a single 6DoF description.

Problems can occur with camera-based motion capture when the three markers are close together physically or have apparent angles, relative to individual cameras, that are very nearly the same. Further issues can arise if the cluster of markers is too far or too close to any of the cameras. Messy merging of these passive markers often results, which contaminates and degrades 6DoF matrix data output. After recording data, each passive marker must be individually labeled, and picked-up again if momentarily dropped. Additionally, even when working with very accurate motion-capture data, animations produced from the captured data often get trapped in the "uncanny valley" where realism is not truly felt and audiences may react negatively. Part of today's failure to create realism occurs because the passive markers used to capture an actor's face may only yield 3DoF data. For example, it may be physically impossible to provide enough adjacent markers to track features such as the pose of the fingertip in 6DoF. There are hybridized motion-capture systems that pair passive markers with inertial sensors, but such systems may have increased complexity and suffer from so-called "double differential" errors.

BRIEF DESCRIPTIONS OF THE DRAWINGS

The accompanying drawings, which are incorporated in and constitute a part of this specification, illustrate an implementation of the invention and, together with the description, explain the goals, advantages and principles of the invention. Corresponding reference numerals indicate corresponding parts throughout the several views of the drawings. In the drawings:

FIG. 1A is a diagram of an example light-direction detector.

FIG. 1B is a top view of an example light-direction detector mounted on a Complementary Metal Oxide Semiconductor (CMOS) chip as the substrate.

FIG. 1C is a diagram showing 6 degrees of freedom of motion for an object.

DETAILED DESCRIPTION OF SEVERAL EMBODIMENTS

Figure 2:
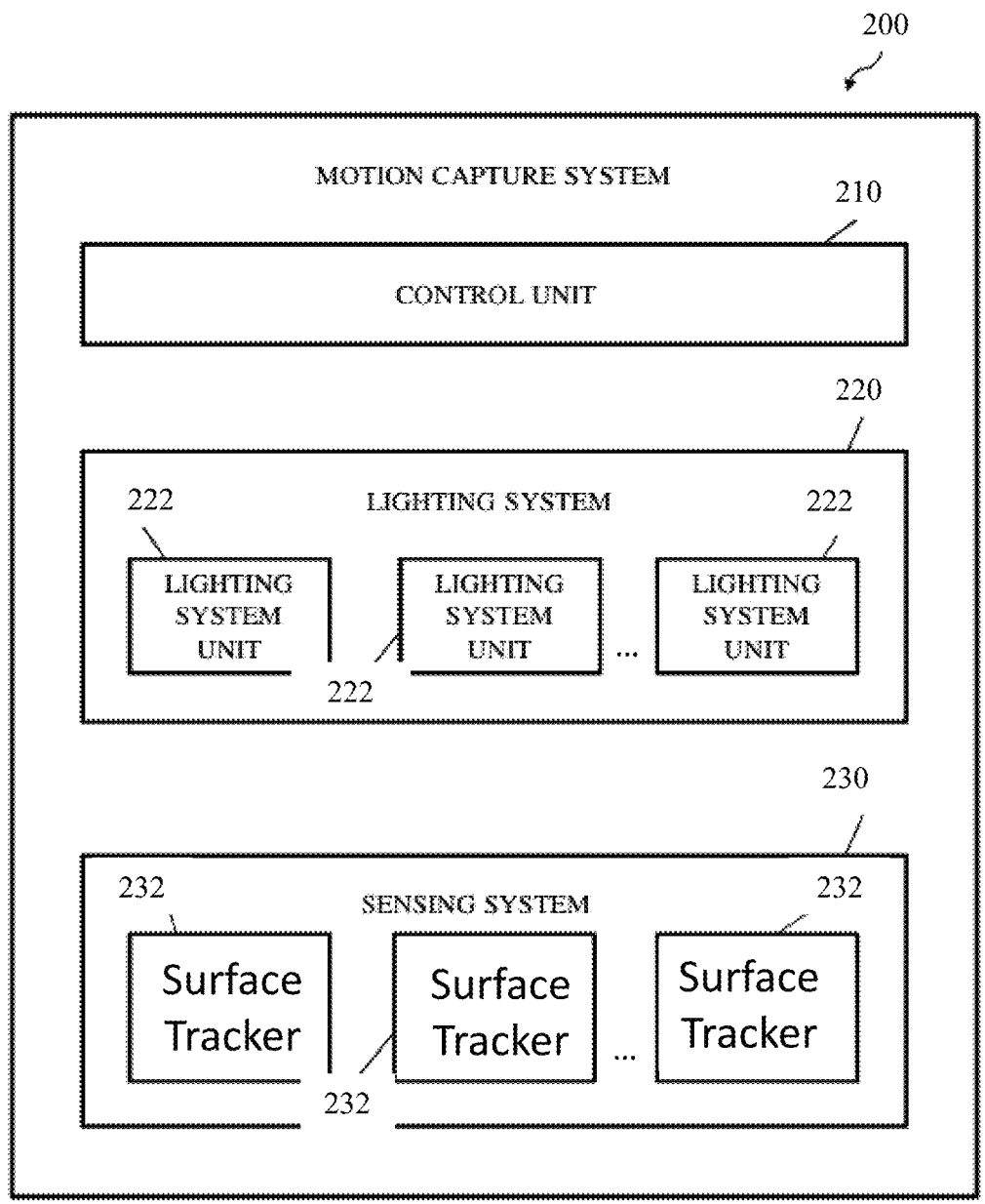
FIG. 2 is a block diagram illustrating a motion capture system, according to some embodiments of the present disclosure.

In the following description, numerous specific details are set forth regarding the systems and methods of the disclosed subject matter and the environment in which such systems and methods may operate in order to provide a thorough understanding of the disclosed subject matter. It may be apparent to one skilled in the art, however, that the disclosed subject matter may be practiced without such specific details, and that certain features, which are well known in the art, are not described in detail in order to avoid unnecessary complication of the disclosed subject matter. In addition, it may be understood that the embodiments provided below are examples, and that it may be contemplated that there are other systems and methods that are within the scope of the disclosed subject matter.

Some embodiments of the present disclosure are directed to a motion tracker device comprising a substrate and a plurality of light-direction detectors (LDD), each configured to detect, at two optically isolated points, the intensity and propagation direction of light emitted from a light source. LDDs are also known as RayIQ devices in some contexts. The LDDs may be configured to generate a current signal representing the photodiode differential and proportional to the intensity of the light, and to transmit the current signal to a computing device. Considering two of the plurality of light-direction detectors, these two light-direction detectors may be mounted on the substrate such that the angle of incidence of the light on the first and second light-direction detectors is different.

In some embodiments, the computing device may be configured to determine the motion of the motion tracker device with six degrees of freedom based on the current signals transmitted from the plurality of light-direction detectors. In some embodiments, each light-direction detector may comprise a microchip. In some embodiments, each light-direction detector may comprise a plurality of photodiodes optically isolated from one another by a stacked metallic layer. In some embodiments, each light-direction detector may be mounted on the substrate at an angle that may be not aligned with or parallel to the surface of the substrate. In some embodiments, each light-direction detector may be mounted on the substrate at an angle of 30 degrees or 60 degrees relative to the substrate. In some embodiments, the motion tracker may comprise a light emission source and the light emission source may an LED. In some embodiments, the light-direction detectors may be mounted on the substrate in orthogonal pairs relative to one another. These orthogonal pairs may also be placed in other discrete angle layouts when mounted on the substrate. In some embodiments, two of the plurality of light-direction detectors may be incorporated into a single microchip. In some embodiments, the motion tracker device may be configured to be mounted on a human fingernail. In some embodiments, the motion tracker device may comprise a second substrate, and a second plurality of light-direction detectors mounted on the second substrate, each configured to detect, at two optically isolated points, the intensity of a light from a light source. The light-direction detectors may be configured to generate a current signal representing the photodiode differential and proportional to the intensity of the light, and to transmit the current signal to a computing device. Considering two of the second plurality of light-direction detectors, these two light-direction detectors may be mounted on the second substrate such that the angle of incidence of the light on the first and second light-direction detectors may be different. The angle of first light-direction detectors relative to the first substrate may be different than the angle of the second light-direction detectors relative to the second substrate. The first plurality of light-direction detectors may be connected to the second light-plurality of light-direction detectors such that the second substrate may be sandwiched between the two layers of light-direction detectors. The light-direction detectors of the first plurality of light-direction detectors may be mounted on the first substrate at an angle of 60 degrees relative to the first substrate and the light-direction detectors of the second plurality of light-direction detectors may be mounted on the second substrate at an angle of 30 degrees relative to the second substrate.

Another aspect of the present disclosure is directed to a system for tracking light comprising a substrate and a plurality of motion trackers mounted at different positions on the substrate. Each motion tracker may consist of a second substrate and a plurality of LDDs, each configured to detect, at two optically isolated points, the intensity of a light from a light source. The light-direction detectors may be configured to generate a current signal representing the photodiode differential and proportional to the intensity of the light; and to transmit the current signal to a computing device. Considering two of the plurality of light-direction detectors, these two light-direction detectors may be mounted on the substrate such that the angle of incidence of the light on the first and second light-direction detectors is different.

In some embodiments, the computing device is configured to determine the motion of the motion tracker device with six degrees of freedom based on the current signals transmitted from the plurality of light-direction detectors. In some embodiments, each light-direction detector comprises a microchip. In some embodiments, two of the plurality of light-direction detectors are incorporated into a single microchip.

The term "light-direction detector," as used herein, refers to any type of optical sensor configured to detect the direction of light from a light source relative to the detector. One example embodiment of such a light-direction detector is discussed in "On-chip sensor for light direction detection", by Hongyi Wang, Tao Luo, Hongjiang Song, and Jennifer B. Christen, Optics Letters 38, 4554 (2013) incorporated herein by reference. FIGS. 1A and 1B provide illustrations of the Wang device. The action of the particular light-direction detector embodiment illustrated in FIGS. 1A and 1B is best described by Wang, > [t]he sensor consists of 50 basic cells connected in parallel. FIG. [1A] shows the structure of two basic cells. The essential feature of this sensor is created by stacking all metal layers, contact, and vias available in the process to create on-chip walls as optical baffles [102]. Two identical photodiodes 104 are located on opposite sides of the wall [185]. When the light comes from directly above the wall [185], the two photodiodes are illuminated equally and produce the same currents. When the light comes from one side above the wall [185], the wall [185] blocks part of the light from the opposite photodiode, which therefore produces less current than the other photodiode. The difference of these two currents depends on the angle of the incident light. It is possible to calculate the angle based on these two currents. id.

The term "six degrees of freedom (6DoF)," as used herein, refers to six potential movements made by a body in space. FIG. 1C illustrates this motion as: side-to-side movement 171 (along the x-axis); up and down movement 172 (along the y-axis); forward and backward movement 173 (along the z-axis); turning about an x-axis movement 174 pitch); turning about a y-axis movement 175 (yaw); and turning about a z-axis movement 176 (roll) (From *A suspensory system for the sacrum in pelvic mechanics: biotensegrity*. S M Levin, in Movement, Stability & Lumbopelvic Pain (Second Edition), 2007. Found online at https://www.sciencedirect.com/topics/medicine-and-dentistry/six-degrees-of-freedom, last visited 2/8/2019).

The present disclosure describes a camera-less optical motion-capture system. Wearable sensors may measure six degrees of freedom (6DoF) of motion of the object to which they are attached by triangulating between angle measurements. This may be made possible by placing light emitting diode (LED) lights, in groups or as single light sources, around a room, for example. Each LED array may be controlled (e.g., by a computer system) to flash in a particular pattern with other individual LEDs or groups of LEDs in a particular pattern (e.g., circular, spiral or linear). A particular group of LEDs may include two, three, four, or greater numbers of LEDs. The light source of a single LED or LED array may be estimated as a point source. By presenting lights that flash in linear arrangements, the angular relationship between light source and sensor may give additional data on 6DoF of the motion of the sensor. By increasing the number of lights flashed at a specific location, the distance from the light source to the sensor may be calculated.

In some embodiments, the system may include a light source located directly on a 6DoF sensor. In some embodiments, the camera-less motion-capture system may be hybridized by combining it with a camera-based motion-capture system measuring only 3DoF. Hybridizing the camera-less system with a camera system for motion capture may be made possible by hardware or software additions that enable serial flashes of LED rings that may surround each motion-capture camera and typically flash simultaneously with the shutter of the camera. With the camera LED rings flashing in a serial sequence, sensors may compute 6DoF relative to statically mounted cameras. With patterned flashing of the LED on the 6DoF sensor, an identifying signature of each sensor may be transmitted to the cameras, and the sensors' 3DoF positions may be constructed in the standard motion-capture process. Hybridizing the camera-less system with a camera-based system may give resiliency to the data by adding redundancy and double checks on the computed results.

FIG. 2 shows a block diagram of a motion-capture system 200, according to some embodiments of the present disclosure. The system may be described as a camera-less optical motion capture. In some embodiments, the system may include a computer system 210, a lighting system 220 and a sensing system 230. The computer system 210 may control the operation of the lighting system 220 and collect data from the sensing system 230. The computer system may calculate motion or position data of the target based on the collected data. The lighting system 220 may include one or more lighting system units (LSUs) 222 which may be controlled by the computer system 210 to flash in a known sequence alone or in clusters of LSUs as close as physically possible as adjacent pairs, triads, quads, or greater numbers. While FIG. 2 shows 3 LSUs, a person of ordinary skill in the art would understand that fewer or more LSUs can be used in some embodiments of the present disclosure and that the particular number of LSUs may be selected based on the requirements for a given application.

The sensing system 230 may include one or more motion trackers 232 which may determine the light intensity at its surface and send readings to computer system 210 where the angle of incidence and motion can be calculated. The sensing system 230 may include any number of motion trackers 232. While FIG. 2 shows 3 motion trackers, a person of ordinary skill in the art would understand that fewer or more motion trackers can be used in some embodiments of the present disclosure and that the particular number of motion trackers image be selected based on the requirements for a given application.

The lighting system 220 may include a number of lighting-system units (LSUs) 222 connected to a computer system, with wires or wirelessly, and configured to emit light. In some embodiments, the number of the LSUs may be between 4 and 100 or more. Each LSU 222 may have a wide angle of light dispersion (>180 degree hemispherical) and may be arranged such that its light saturates a rectangular volume or area within which motion capture of movement may occur. The wide angle of light dispersion from an LSU 222 may enable motion capture by motion trackers located near the walls of the room. The LSUs 222 may emit light in the spectrum from violet to infrared (e.g., having a wavelength of 400 nm to 1.2 mm). Each discrete LSU may include a number of LEDs, Wi-Fi, digital communication equipment, a battery or some combination of these elements. In some embodiments, the number of LEDs may be 40 or more. The powering of all or a select number of LEDs on each LSU may be controlled by the computer system to illuminate with a specific duration and frequency.

Figure 3A:
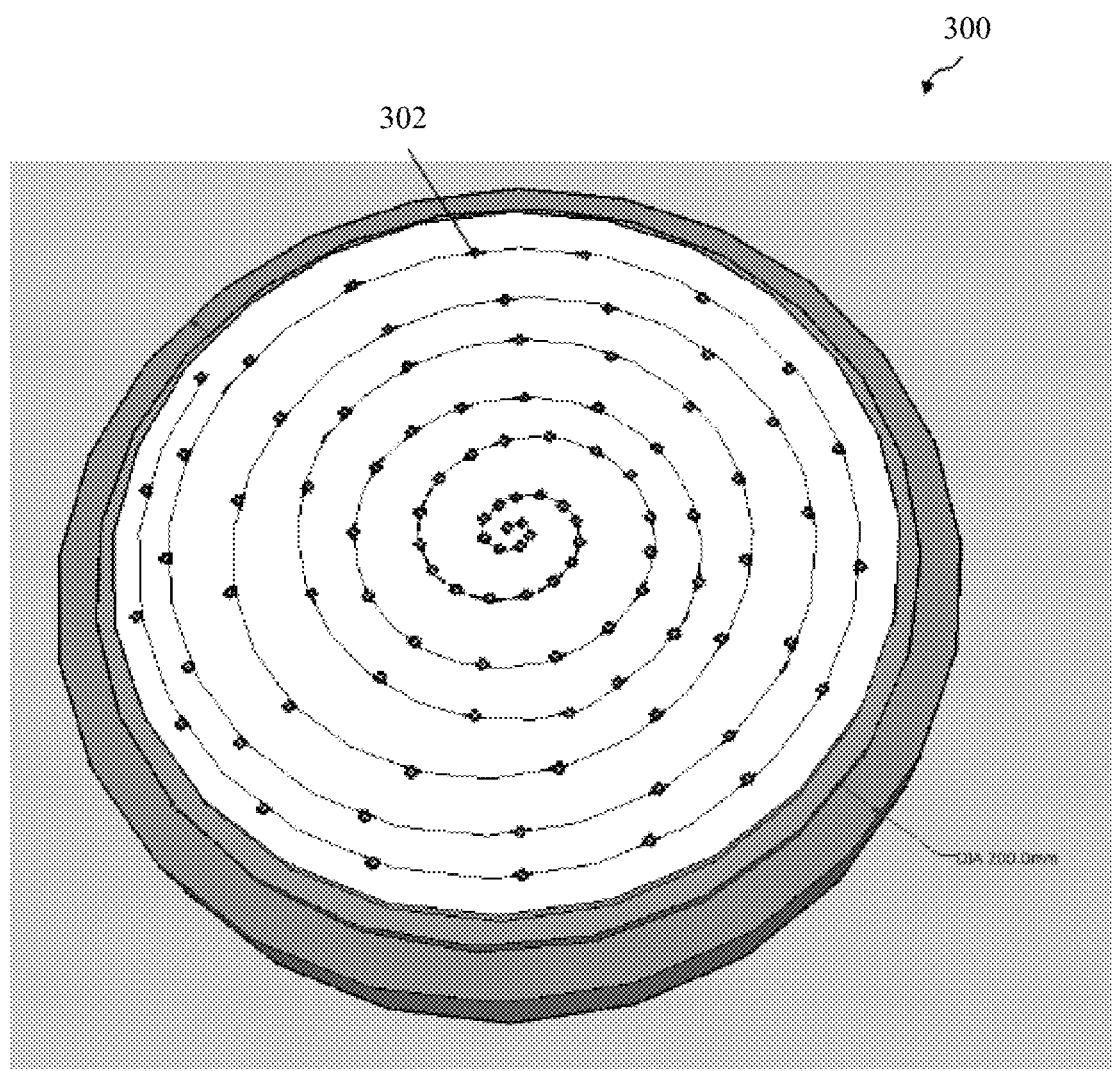
FIG. 3A is a perspective view of a lighting-system unit (LSU), according to some embodiments of the present disclosure.

FIG. 3A shows an example LSU 300 with a plurality of light emitting diodes (LEDs) 302 arranged in a spiral layout, according to some embodiments of the present disclosure. In some embodiments, the LEDs may also be arranged in a concentric circular layout.

Figure 3B:
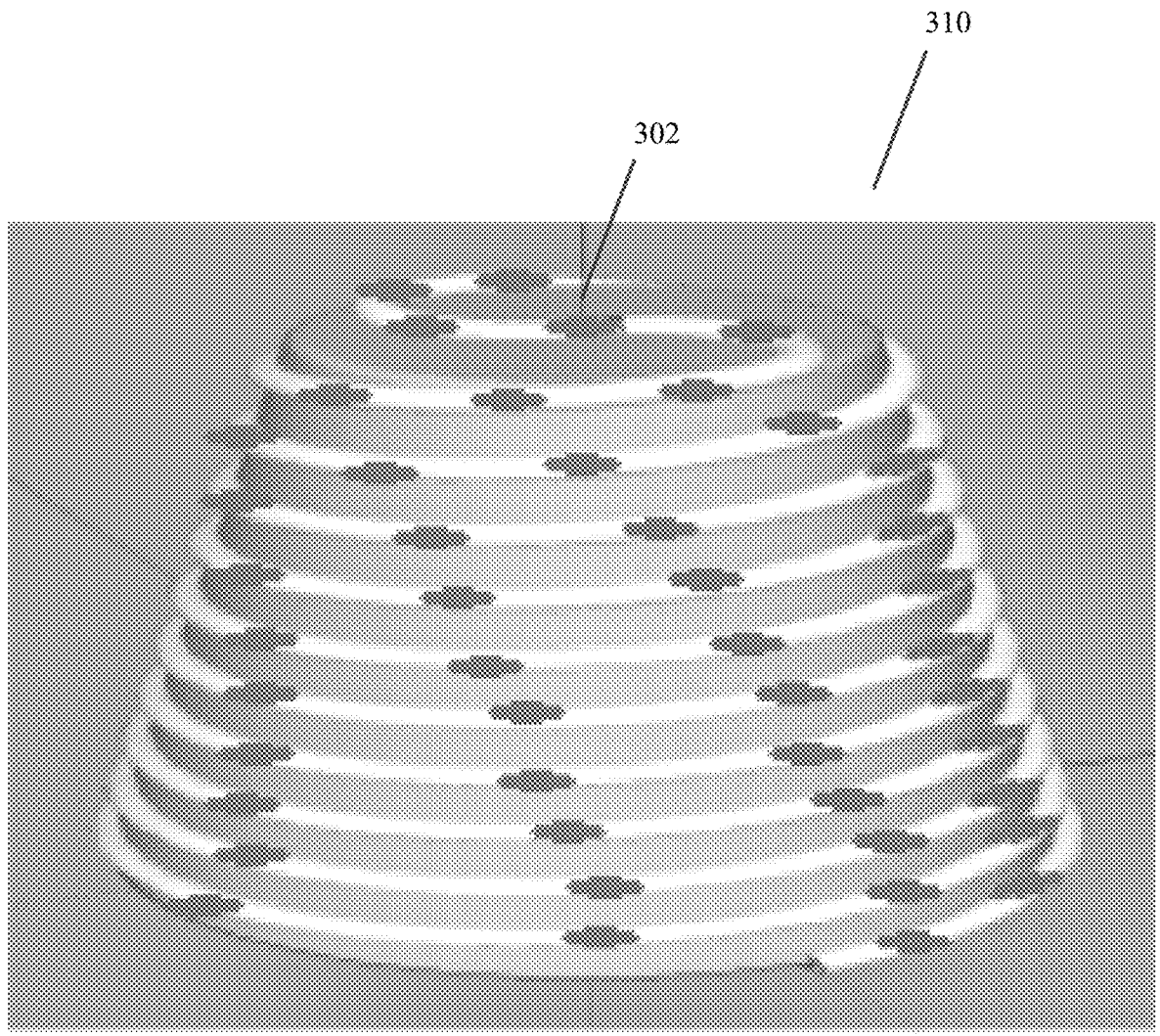
FIG. 3B is a perspective view of an LSU, according to some embodiments of the present disclosure.

FIG. 3B shows an example LSU 310 with a plurality of LEDs 302 arranged in a spiral conical layout, according to some embodiments of the present disclosure.

Figure 3C:
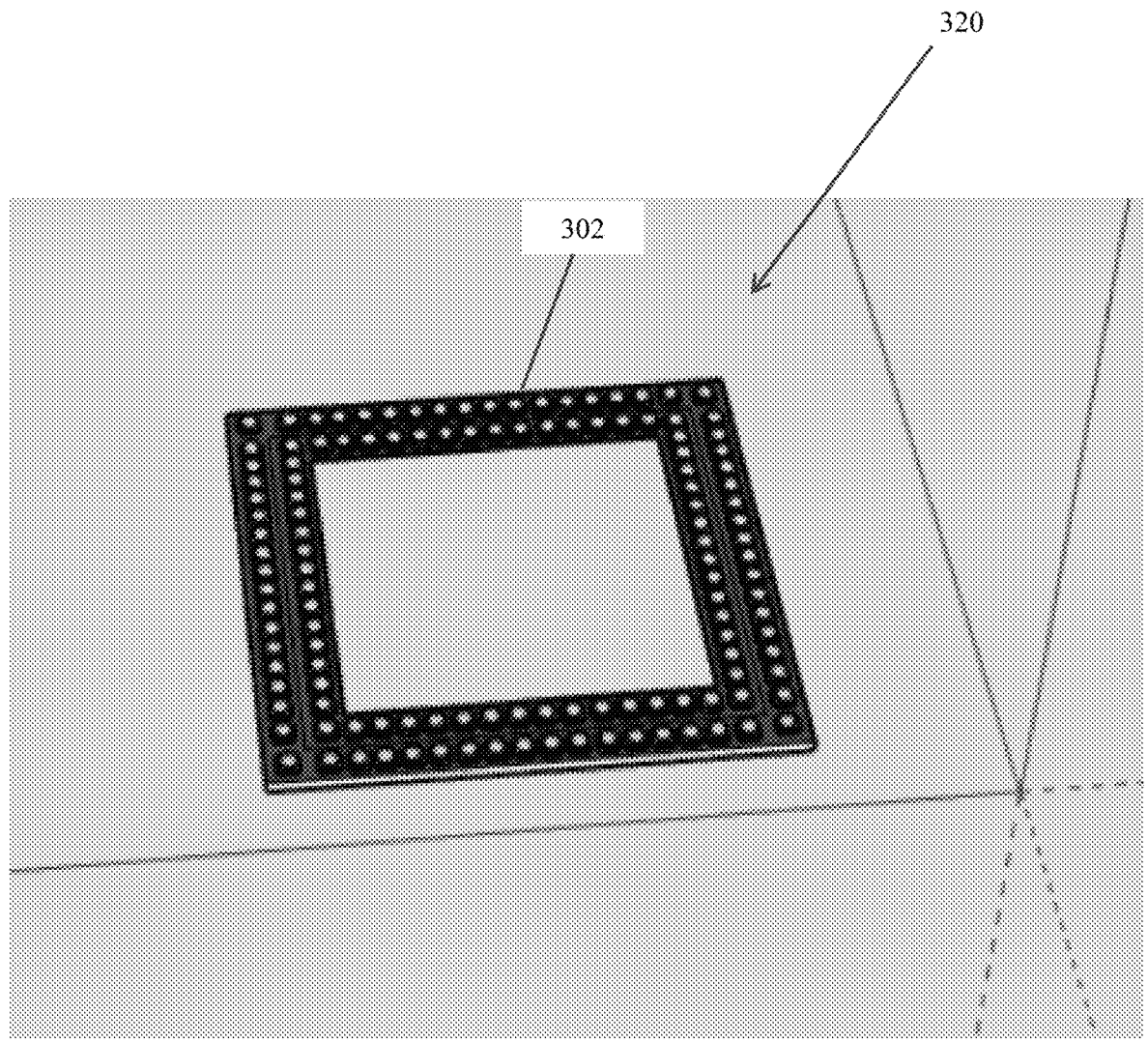
FIG. 3C is a perspective view of an LSU, according to some embodiments of the present disclosure.

FIG. 3C shows an example LSU 320 with a plurality of LEDs 302 arranged in a linear layout, according to some embodiments of the present disclosure. The LSU may be very small (e.g., a few millimeters long) or very large (e.g., several feet long). In some embodiments, the LEDs may be arranged in a number of rows (e.g., 3, 4, 5 rows or more) with any number of LEDs in each row (e.g., 20, 40, 50 or more). In some embodiments, the LEDs may be arranged in rows about the perimeter of a rectangle where the center of the rectangle may be open as depicted in FIG. 3C.

Figure 3D:
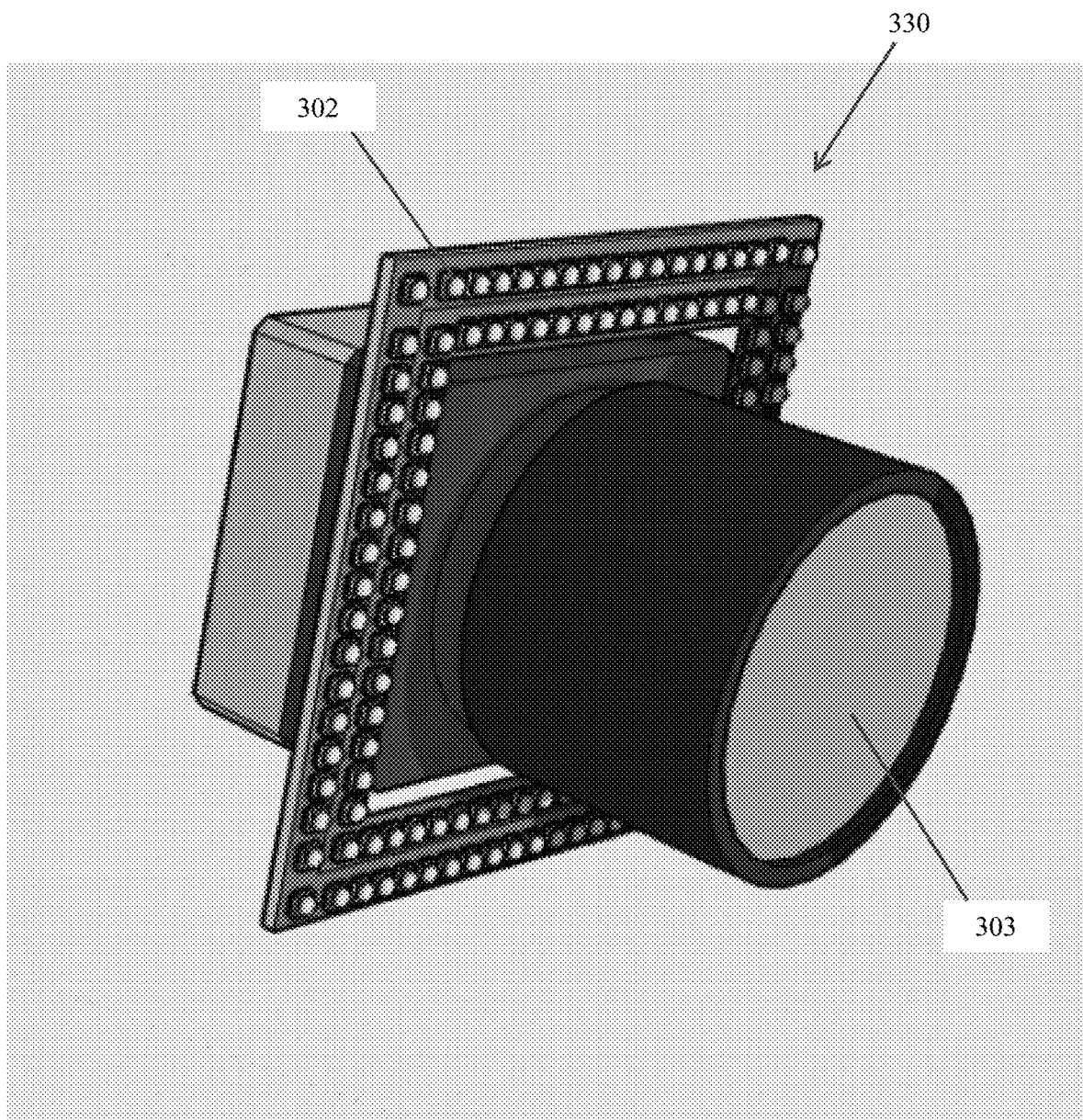
FIG. 3D is a perspective view of an LSU mounted on a generic motion-capture camera, according to some embodiments of the present disclosure.

FIG. 3D shows an example LSU 330 with a plurality of LEDs 302 arranged in a quadrilateral arrangement (similar to that shown in FIG. 3C), and mounted to a generic motion-capture camera 303 according to some embodiments of the present disclosure. In some embodiments, LEDs in a lighting system unit may be arranged in another layout.

Figure 4:
FIG. 4 is a view of an example lighting system, according to some embodiments of the present disclosure.

FIG. 4 shows an example lighting system 400 including four LSUs 420. This type of example lights system 400 may include as few as one LSU 420 or as many as the stand apparatus can support. In some embodiments, the LSUs 420 may be mounted on a supporting stand or a mobile tripod 402 for specialized motion capture, according to some embodiments of the present disclosure.

Figure 5A:
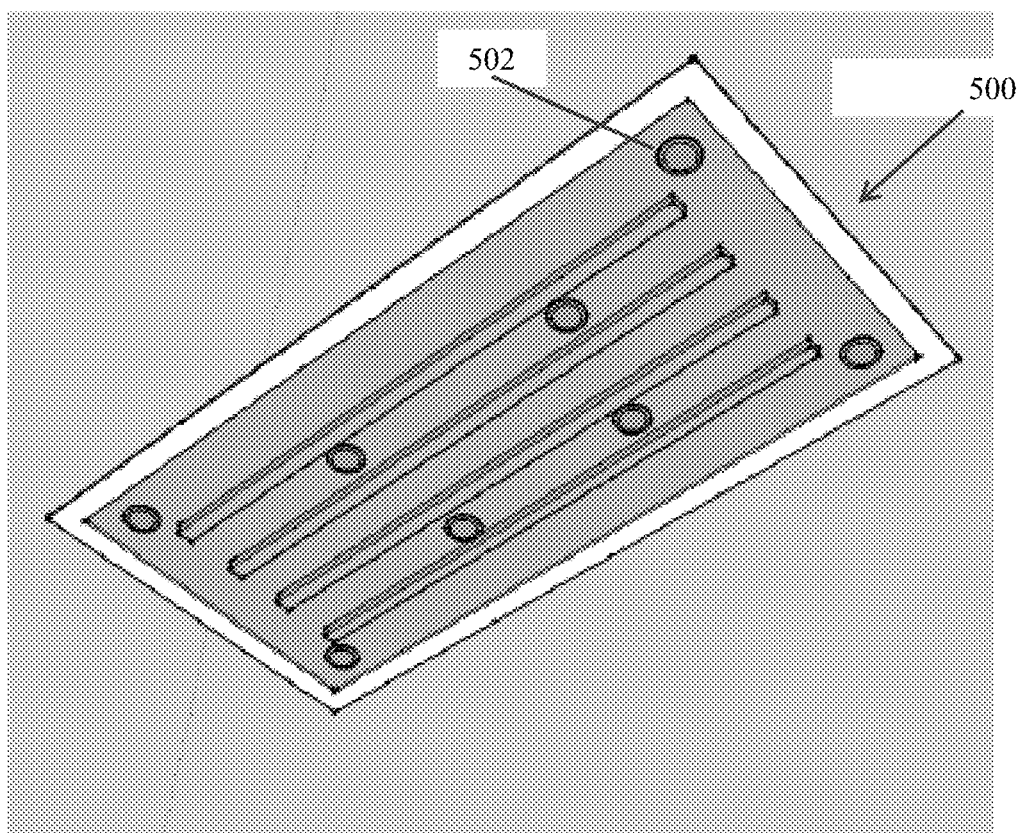
FIG. 5A is a view of an example lighting system, according to some embodiments of the present disclosure.
Figure 5B:
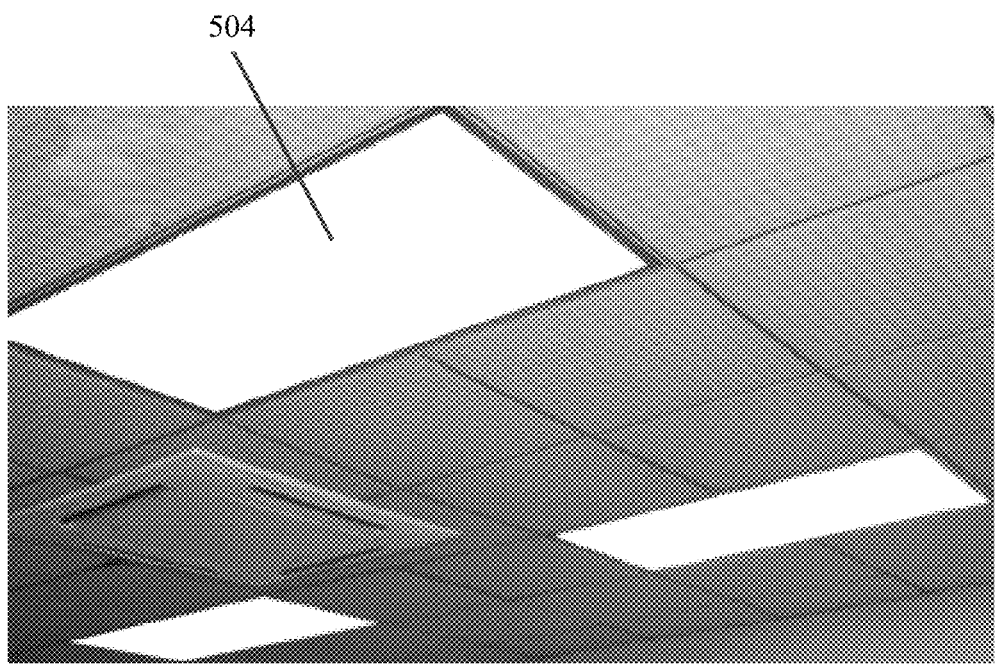
FIG. 5B is another view of an example lighting system, according to some embodiments of the present disclosure.

FIG. 5A shows an example layout of an LSU 500, according to some embodiments of the present disclosure. The LEDs 502 may be arranged in panels of room lights. For example, the LEDs 502 may be mounted in a standard 4'×2' recessed ceiling panel lighting fixture. FIG. 5B shows an example embodiment of a standard 4'×2' ceiling panel lighting fixture 504.

Figure 6:
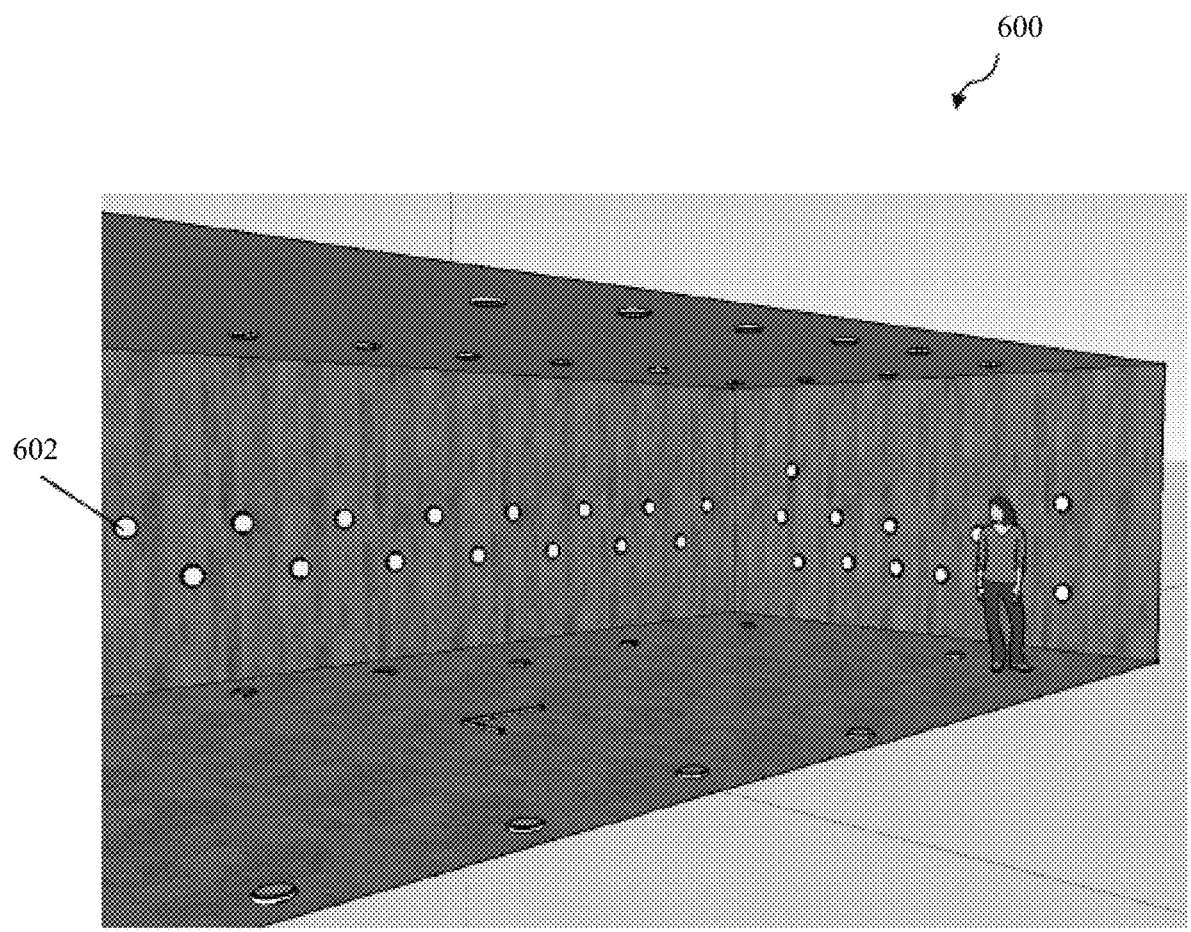
FIG. 6 is a view of an example motion capture lab, according to some embodiments of the present disclosure.

FIG. 6 shows an example layout of a motion-capture lab 600, according to some embodiments of the present disclosure. Any number of LSUs 602 may be mounted on the walls, floors and ceilings of such a motion-capture lab 600.

Referring to FIG. 7, a motion tracker 700 may generally comprise two or more light-direction detectors 702 mounted on a substrate 703. Each light-direction detector 702 may be configured to detect, at two optically isolated points, the intensity of a light from a light source, to generate a current signal representing the photodiode differential and proportional to the intensity of the light, and to transmit the current signal to a computing device. The light-direction detectors 702 may be mounted on the substrate at an angle that is not aligned with or parallel to each other. Each light-direction detector 702 may be mounted on the substrate at an angle that is not aligned with or parallel to the surface of the substrate. One light-direction detector 702 may be mounted on the substrate such that the angle of incidence of the light on that light-direction detector is different than the angle of incidence of the light on one other of the light-direction detectors 702 attached to the same substrate. The mounting of the light-direction detectors 702 at these angles may allow the motion of a motion tracker to be determined with six degrees of freedom. This mounting of the light-direction detectors 702 at positions yielding different angles of incidence is critical because the varied angles increases the breadth of the light receptivity of the motion tracker and the data available from the sensors, thus allowing the 6DoF analysis.

Each light-direction detector 702 may be configured as a microchip capable of mounting on the substrate, similar to the prior art light-direction detector shown in FIGS. 1A and 1B and discussed above.

Figure 7A:
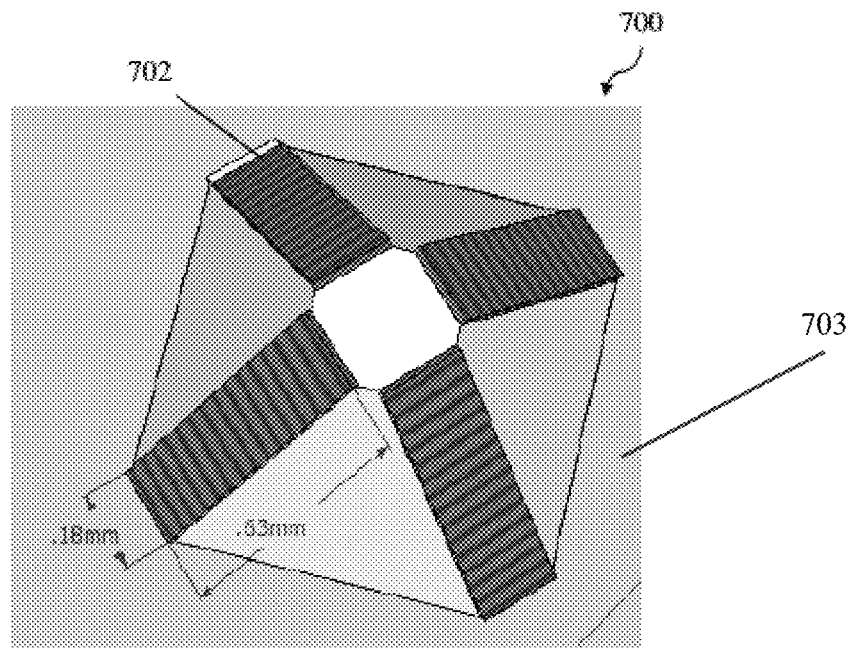
FIG. 7A is a view of an example motion tracker, according to some embodiments of the present disclosure.

The light-direction detectors 702 may be mounted to the substrate at 45 degrees to the plane of the substrate. FIG. 7A shows a motion tracker 700 with 4 light-direction detectors 702 angled at 45 degrees to the horizontal substrate plane, combined to give a sensitivity hemisphere of approximately 200-degree, according to some embodiments of the present disclosure. As shown in FIG. 7A, each light-direction detector 702 may have a width of 0.18 mm and a length of 0.63 mm. In some embodiments, the light-direction detectors 702 may have other dimensions.

Figure 7B:
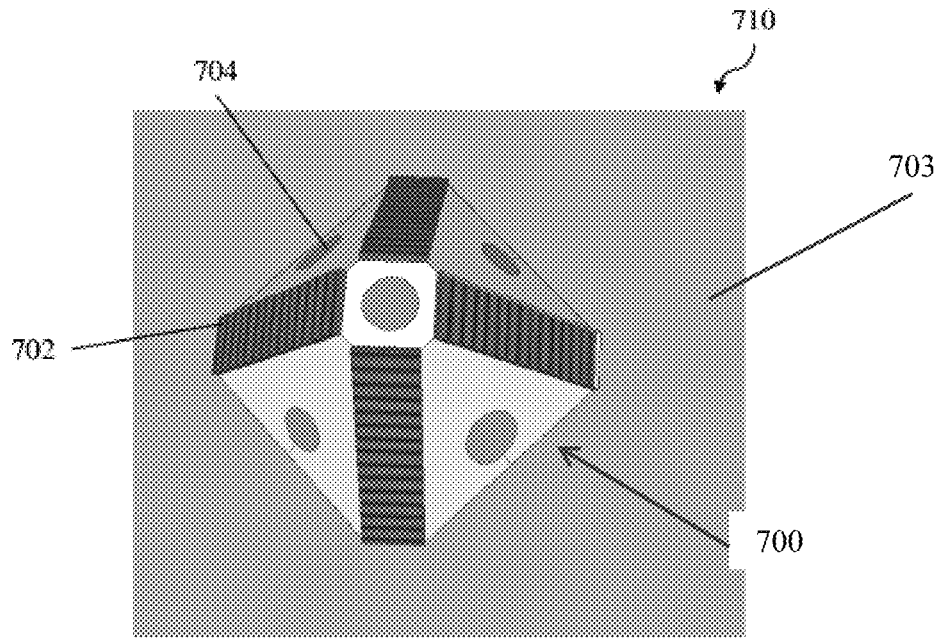
FIG. 7B is another view of an example motion tracker, according to some embodiments of the present disclosure.

FIG. 7B shows a motion tracker unit 710 with 4 light-direction detectors 702 angle at 60 degrees to the horizontal plane, according to some embodiments of the present disclosure. The light-direction detector 702 detects light direction in one direction (perpendicular to the chip long axis), thus for a two-dimensional angle, two light-direction detectors 702 may be paired at orthogonal orientation relative to each other. If the light-direction detector 702 has a maximal angular detection range of 110 degrees, (55 degrees left and right of perpendicular to the light-direction detector), the final design of the motion tracker may be comprised of a 2 pairs of light-direction detectors, offset in angle to increase angular detection range to 180 degrees or greater. If further angular range above a 180-degree hemisphere were deemed necessary, additional pairs of light-direction detectors 702 may be fabricated onto the motion tracker. Other embodiments may have the light-direction detectors 702 mounted at different angles relative to the substrate, such as 15 degrees, 30 degrees, 60 degrees, or any other angle deemed necessary.

The motion tracker may include a light emission source. The light emission source may be an LED bulb or any other type of light emitter known in the art. FIG. 7B shows a motion tracker unit 710 with 5 LED bulbs 704, according to some embodiments of the present disclosure. The motion tracker may be equipped with a LED fabricated adjacent to the array of light-direction detectors 702 in a single device. The primary location of an LED 704 may be the top of the pyramid of light-direction detectors, and secondary locations radial from the center point along 45-degree directions relative to the primary coordinate system of the paired light-direction detectors. These light emission sources on the motion tracker allow relative Tracker-to-Tracker 6DoF to be directly computed, even without being within an LSU. This would allow motion detection from any one motion tracker to another (e.g., from eyeglass frame to smartphone, from vehicle to vehicle, from vehicle to structure). The light emission source may also assist in locating the motion trackers.

The light-direction detectors 702 may be integrated circuit chips mounted to any suitable substrate 703 type known in the art, such as a CMOS chip. Two light-direction detectors 702 may be formed in the same chip and mounted to a substrate 703 as a single unit.

The motion tracker may be configured to be mounted to any type of wearable or movable device. Such devices may include tripods, selfie sticks, brackets, eyeglasses, fingernails, smartphones, or any other suitable device.

Figure 7C:
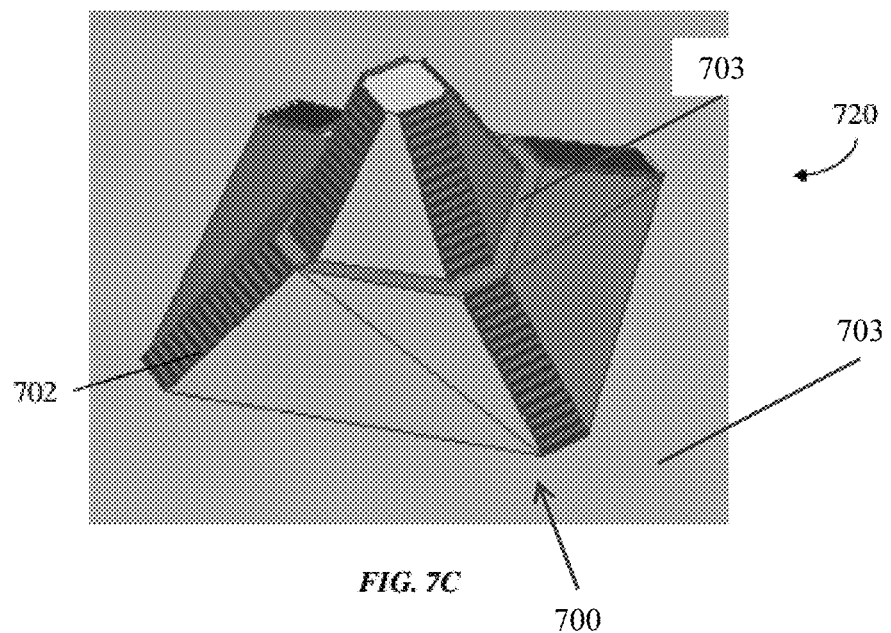
FIG. 7C is another view of an example motion tracker, according to some embodiments of the present disclosure.

In an alternative embodiment, the motion tracker device may comprise two substrates 703 and two light-direction-detector layers. FIG. 7C shows an example embodiment having a motion tracker unit 720 with two light-direction-detector layers. Each layer 704 may comprise two or more light-direction detectors 702 mounted to a substrate 703. In each layer, one light-direction detector 702 may be mounted on the substrate such that the angle of incidence of the light on that light-direction detector is different that the angle of incidence of the light on one other of the light-direction detectors 702 attached to the same substrate.

The mounting of the light-direction detectors 702 at these angles may allow the motion of a motion tracker to be determined with six degrees of freedom. This mounting of the light-direction detectors 702 at positions yielding different angles of incidence is critical because the varied angles increases the breadth of the light receptivity of the motion tracker and the data available from the sensors, thus allowing the 6DoF analysis.

The light-direction detectors of the first layer may be mounted to the first substrate at an angle that is not aligned with and not parallel to the substrate (60 degrees in FIG. 7C). The light-direction detectors 702 of the second layer may be mounted to a second substrate 706 at an angle that is not aligned with and not parallel to the substrate (30 degrees in FIG. 7C). Further, the angle of the light-direction detectors of the first layer relative to the first layer's substrate may be different that the angle of the light-direction detectors of the second layer relative to the second layer's substrate. As shown in FIG. 7C, the two light-direction-detector layers 704 and 705 may be mounted on top of one another such that the second substrate 706 is sandwiched between the two layers. Configurations with different angles of the light-direction detectors 702 relative to the substrate increase the overall breadth of light angles that can be detected by the motion tracker. The different LDD-to-substrate angles of the two layers is critical because the combination of these different angles increases the breadth of the light receptivity of the motion tracker and the data available from the sensors, thus allowing the 6DoF analysis. The combination in the example embodiment of FIG. 7C may result in a 230-degree hemisphere of light detecting sensitivity. Other combinations of angles are possible and may be selected to achieve the desired angular end result as would be understood in the art. Additionally, overlapping angular detection ranges may increase precision and accuracy of the motion tracker, such that the increase in complexity of the light-direction detector 702 may be a worthwhile tradeoff for the increased complexity of analysis. Increased precision and accuracy may also be obtained through multiple discrete readings of direction by separate light-direction detectors 702 while referencing a single LSU.

Figure 7D:
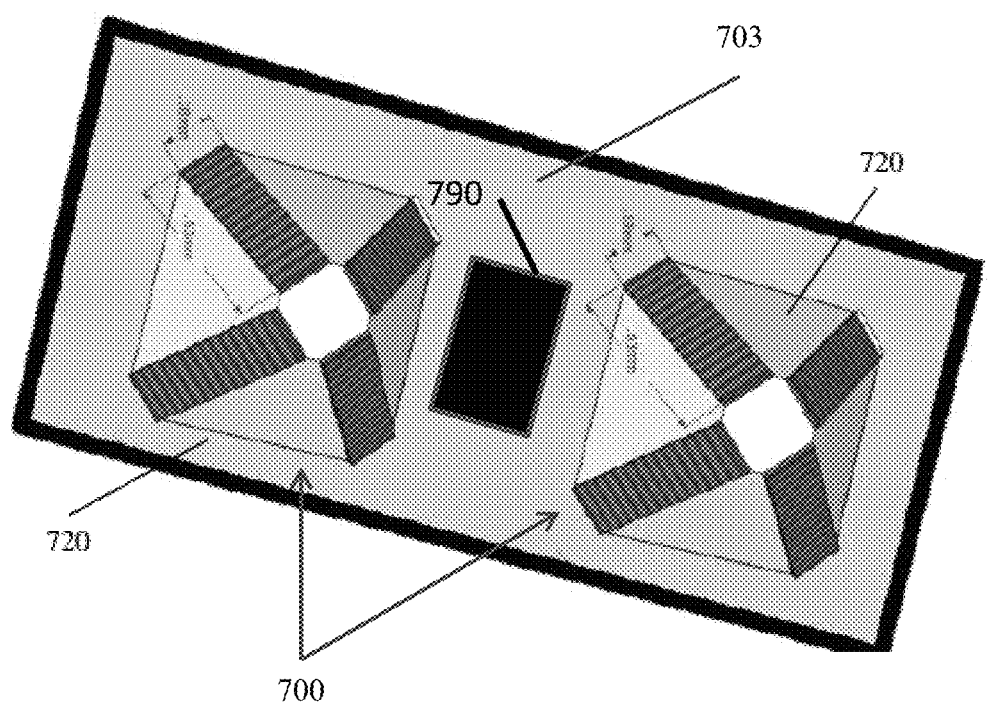
FIG. 7D is another view of an example motion tracker, according to some embodiments of the present disclosure.

In an alternative embodiment, multiple motion tracker devices may be mounted to a single substrate 703. FIG. 7D shows a pair of motion tracker units 720 attached to a single rigid substrate 703, according to some embodiments of the present disclosure. The angles of the light-direction detectors 702 may be the same in each motion tracker device mounted to the substrate or different motion trackers may have different angles.

In order to perform calculations on the 6DoF data of a motion tracker, each LSU of the lighting system must have known 3D coordinates. The precise coordinates of each light unit may be determined through a calibration process. To calibrate the motion-capture system, a calibration frame consisting of three motion trackers at a known and precise physical spacing may be placed in the area where most of the lighting system units will be pointed or visible. The precision calibration frame may have a known geometry that allows a mathematical triangulation of each lighting system unit in turn.

The lighting computer system may record and transmit time-stamped data describing the timing of power on and off events for each LSU. These events may occur at assigned times. In some embodiments, each LSU may be turned on for as little as 20 microseconds in a set sequence. There may be no delay between one unit turning off and the next turning on. The number of LSUs grouped in the lighting system may determine the cycle time (for instance 50 LSUs may give a 100 Hz cycle time). Any number of LEDs may be turned on during the unit's active time in each cycle, but may be grouped into sets that illuminate at the same time. Each sequential group size may get larger as the distance from the center point increases. Group sizes may increase from 1 (center point), next 2, next 4, next 8, next 16, next 32 or similar group-size growth trend. The center most LED may be powered on during each cycle, and additional numbers of LEDs may activate in sequence following adjacent neighbor LEDs in the spiral arrangement. The lighting of LEDs on an LSU may be patterned to emulate a point source of light at varying intensities. When the motion tracker is close to the LSU in 3D space, one central LED may be lit on that LSU, and as the motion tracker moves farther from an LSU, more lights may be turned on, and the LSU may still be perceived as a point light source by the system. The number of LEDs turned on at each unit's designated time point may be adjusted via system optimization commencing at the initiation of the lighting system. Initial cycles of the units may initialize with all LEDs illuminating simultaneously, and the number of LEDs illuminated may be reduced to lower light intensity from most those that are most distal on the spiral to those most proximal relative to the center point of the spiral on each unit, or by turning on and off expanding concentric rings in a circular arrangement of LEDs. The reduction in light output serves as a signal of the distance to the object the lighting system may be illuminating. One quiescent period of 20 microseconds more or less may be incorporated into the cycle of powering the LSUs in order to take a background reading of ambient light direction and intensity conditions to subtract from both net light intensity and net light direction (sunlight, room lights or other).

When an LSU is formed into linear segments of LEDs (single line, square or rectangular quadrilateral), the LEDs may flash in a sequence such as: top row, bottom row, left row, then right row. The flashing may be organized to create unique shadow patterns on the light-direction detectors of each motion tracker. These unique shadows are due to the physical distance from left to right LEDs, and top to bottom LEDs. The location and linear equation of each segment may be taken from the calibration operation and stored in software, and these LSUs may be considered as other than a point light source. The different shadows created by light coming from adjacent locations may be used to create a better definition of the Shadow Tracker 6DoF through linear interpolation of subsequent readings and pattern matching. The software may anticipate shifting shadows from the series of adjacent LSU linear segment flashes. When light from linear arrays strikes the motion tracker may read the direction of the light relative to a line of known location and orientation, which may be used to refine the 6DoF of the motion tracker. The use of linear arrangement of LEDs allows for greater intensity of light to be delivered without creating large areas of penumbra in the cast shadows. The linear arrangement may be placed parallel with the principal axes of an associated camera. The spatial arrangement of the linear segments may serve to emphasize edge detection of shadows aligned with the linear sections. For example, top and bottom flashes may discretize the upper and lower limits of a physical object, while left and right flashes may discretize vertical edges of an object. Small penumbra effects may influence object measurements in perpendicular directions to the linear light segment in use but may still contain usable motion-capture data.

Figure 8A:
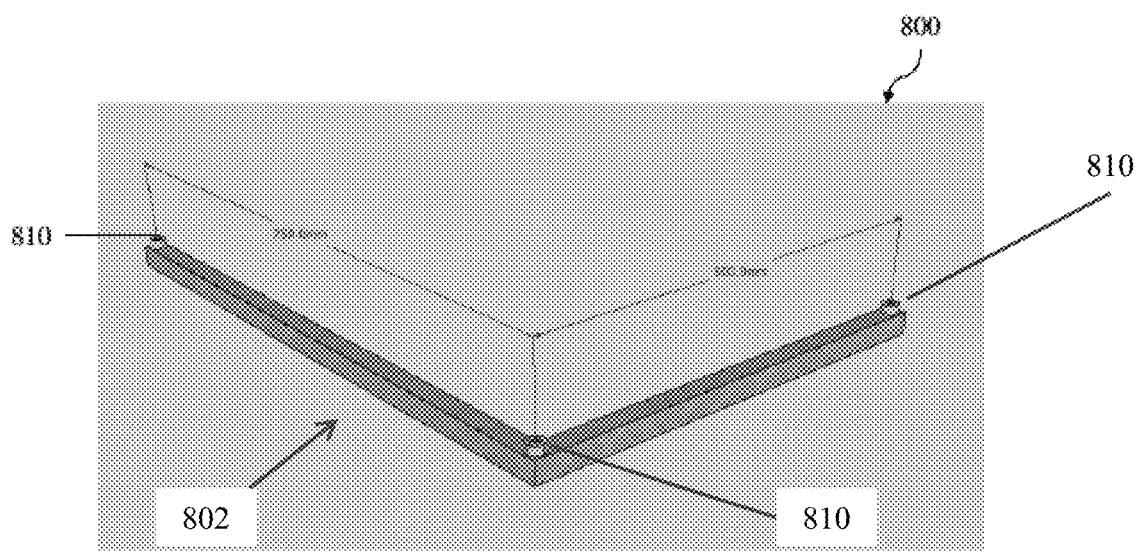
FIG. 8A is a view of an example calibration frame, according to some embodiments of the present disclosure.

FIG. 8A shows an example embodiment of a calibration frame 800 with 3 motion trackers 810, according to some embodiments of the present disclosure. The calibration frame may take the form of an L (L-Frame 802) with one motion tracker 810 at the vertex and one motion tracker 810 at each end point. In some embodiments, the length of the two arms may be 750 mm and 500 mm respectively.

Figure 8B:
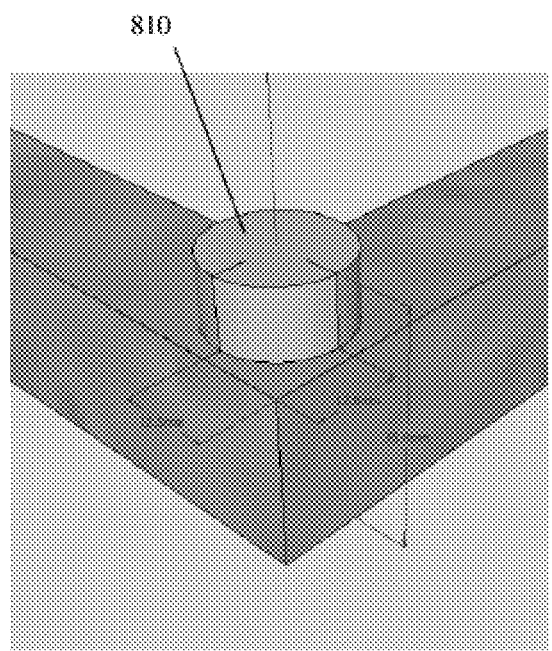
FIG. 8B is another view of an example calibration, according to some embodiments of the present disclosure.

FIG. 8B is a close-up view of a calibration frame corner with a motion tracker 810, according to some embodiments of the present disclosure. Data describing the intersection of 3 vectors allows for 3 paired calculations and by averaging the solutions, the 3D coordinates of each LSU impinging on the calibration frame can be determined. In calibration, three measurements may be made simultaneously of each LSU on the frame, from motion trackers labeled as Origin (at the corner of L-Frame 802), long (at the end of the long arm of the L-Frame 802), and short (at the end of the short arm of L-Frame 802). From these 3 measurements, triangulations may be constructed to locate the LSU in 3 dimensions, relative to the L-Frame 802 origin (translated to physical corner of L-Frame 802). Origin-Long, Origin-Short, Long-Short triangulations may be averaged to describe the 3D coordinate of the LSU currently illuminated. The calibration frame allows identification of the 3D location of each LSU within its range, which in turn may be linked to the sequence of each unit's on/off timing in a lighting cycle. For an LSU configured as a linear array, where each line of LEDs is a subset of the LSU, the endpoints of each linear segment may be individually mapped, and the structure of the light formation may be automatically determined in the calibration procedure.

Figure 9:
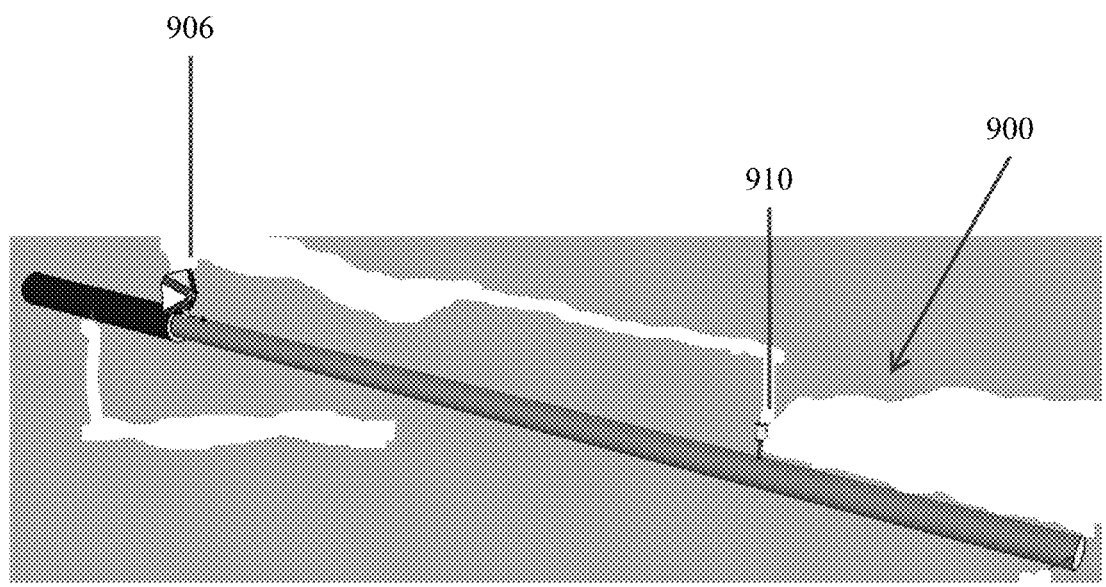
FIG. 9 is a view of an example wand, according to some embodiments of the present disclosure.

FIG. 9 shows an example wand 900 for calibration, according to some embodiments of the present disclosure. In addition to the calibration frame, this wand may be an adjunct tool. The wand 900 may be an elongate tool having a motion tracker 906 near one end and an LSU near the opposite end. The wand 900 may be long or short as needed for the particular application (e.g., 1 foot, 4 feet). The wand 900 may be comprised of any suitable material as known in the art (e.g., fiberglass, plastic, polyvinyl chloride (PVC)). The motion tracker 906 may be offset from the end of the wand 900 and offset from the longitudinal center of the wand 900. The LSU 910 may be offset from the end of the wand. The space between the LSU and the motion tracker may be any distance that affords reliable data (e.g., 12 inches, 25 centimeters, 100 centimeters).

The wand allows the motion-capture system operator to locate landmarks, calibrate additional light system units in the plane of the calibration frame, and to perform other functions. In some embodiments, the wand 900 may be moved into the area with the calibration frame. Once the locations of the majority of LSUs are calculated with the frame, the wand can be brought into play. The LSUs may excite the motion tracker on the wand. The motion tracker on the wand then reads the location of the LED on the wand and the calibration frame motion trackers read the wand LED. Given the data from the wand motion tracker, the wand may be used to locate other LSU in the area that are not in readable positions relative to the L-Frame 802 (e.g., on the same plane as the L-Frame, or around a corner in a complex lab set-up with doorways or furniture).

In some embodiments, the wand 900 may be pointed at important landmarks such as a knee joint, or somewhere spot in a space where a motion tracker is not located. These would be positions that should be referenced to other motion trackers in the capture process. When tracking a human body, for example, the motion tracker would typically be at the mid-point of a thigh segment and of a lower leg segment, but a researcher may need to know where the knee joint is. By referencing the knee joint with a palpation and measuring location with the wand relative to the thigh segment, calculations may be compared to the 6DoF of one segment transformed into the coordinate system of an adjacent 6DoF object. As such when performing landmarking operations, the object to be captured and the wand may be in the area at the same time, and the computations may be the same for locating LSUs, L-Frame, and wand. The motion trackers 700 on the object measure the coordinate system of the LSU in the area, and can indicate the location of the wand LSU 910 relative to the wand tip 902. The system LSUs may excite the motion tracker 906 on the wand 900, and, given the resultant 6DoF information about the motion tracker, the 6DoF information about the wand tip can be interpolated. The LSU on the wand may flash serially with those LSUs in the area such that a special wand-LSU timing may be incorporated into the LSU activation pattern as controlled by the computer system. The computer system "knows" that the wand-LED is a non-stationary light source. The motion tracker of the wand, the L-Frame 802 and the object to be tracked can be computed based on the wand-LED location relative to the 6DoF of each motion tracker in line of sight to the wand-LED.

Another use of the wand 900 may be to point the wand 900 directly at an LSU to determine the direction that each LSU may be pointing at that moment in time. If the wand is generally perpendicular to the LSU, this added information (besides the 3D coordinates of the LSU) consists of the direction from which the light of each LSU may be coming into the area. Since the LSU has two sides, one where the light comes out, and one mounting side (mounted to a wall, a ceiling, a floor, an object, etc.), the light emitted by the LSU may only be projected from roughly a 180-200 degree portion of a sphere. Giving the system software the center point and orientation of the LSU, and thus the spherical portion of light, may assist in reducing the complexity of computations.

Figure 10:
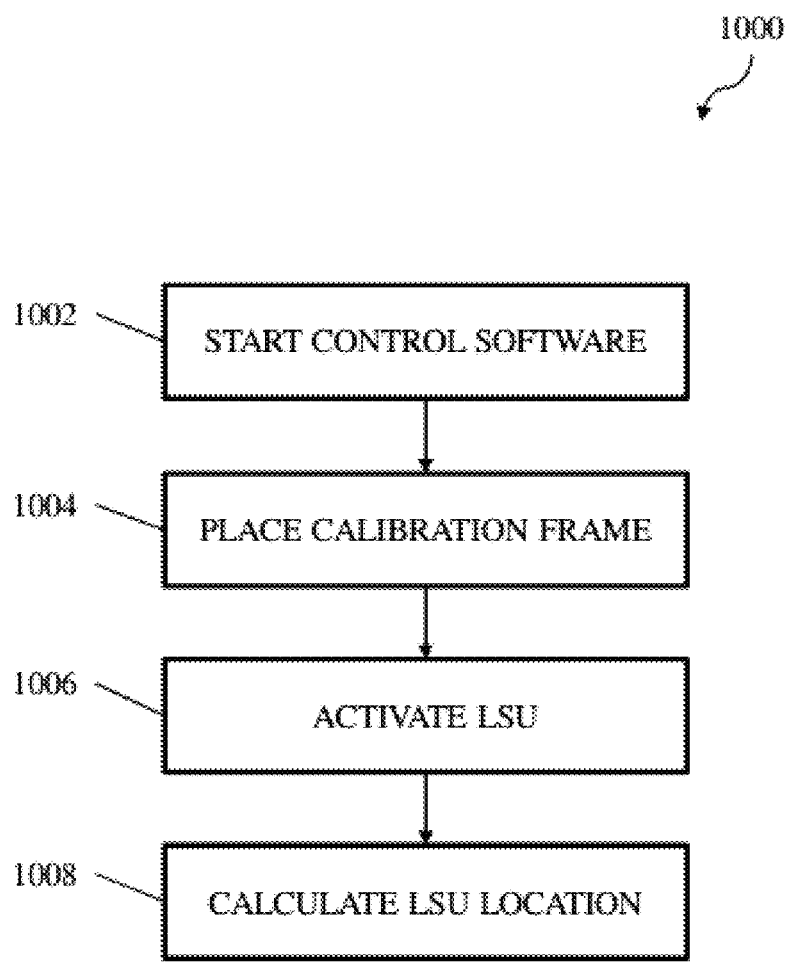
FIG. 10 is a flow diagram illustrating an example calibration method, according to some embodiments of the present disclosure.

FIG. 10 is a flowchart showing an example calibration method 1000 for a camera-less motion detection system, according to some embodiments of the present disclosure, as shown generally in FIG. 2. At step 1002, a proprietary software (e.g., system software) may be started on a computer system, the computer system may turn on all LSUs. Each LSU may illuminate in a sequence, repeating on/off cycle with 2 ms on times. The system software may detect (via radio, Wi-Fi, or Bluetooth transmission of data) for the presence of motion trackers in the vicinity.

At step 1004, the calibration frame may be placed at a desired location and orientation, aligning the desired origin with the corner of the frame, and the long and short arms pointing in desired X and Y directions. This location of the L-shaped frame sets the Global Coordinate System (GCS) of the volume or area. When the calibration frame is placed in a position such that both arms are horizontal, by default, the origin of the GCS (0,0,0) is at the physical corner of the L-Frame, the short arm of the frame describes the x-axis (usually to the right), the long arm describes the y-axis (usually anterior to the person holding the L-Frame 802), and the z-axis would then be, by definition, pointing upward (away from the transverse plane of the frame or ground). The origin may be further translated mathematically from the corner of L-Frame 802 to any location in the volume or area, and the long and short arms may be designated as any coordinate direction, and the coordinate system may be tilted in any of three directions relative to the L-Frame 802 as well.

In one embodiment, the L-Frame 802 has 3 motion trackers on it, one near the junction of the short and long arms and called "Origin," and one near the end of each arm, called "Long" and "Short." The motion trackers may be attached to the L-Frame 802 with the local coordinate system of the motion trackers aligned with the arms of the L-Frame. The L-Frame 802 may provide a consistent way to align the Global Coordinate System of the volume or area in the system software with other structures in the space. These structures may include an instrumented force plate, a treadmill, stairs or other any other structure or feature. Conveniently, the two arms of the L-Frame 802 ensure that the calibration device lays parallel to the transverse plane of the floor. Other smaller calibration frames may be fabricated with discrete spacing between motion trackers to allow for smaller or larger measurement volumes, and or for measurement volumes with local coordinate system origins not aligned with the transverse plane of the ground. Calibration frames may be in the shape of a right triangle or any other shape that allows calibration of the system.

At step 1006 of the method embodiment depicted in FIG. 10, the LSU to be calibrated may be turned on and off with a 20 microsecond interval. The system then records and transmits (via RF, Wi-Fi or any other transmission method) one 2-dimensional (2D) angle from each of the three example motion trackers on the calibration frame to the system software on the computer system. With three 2D angles between the calibration frame and the first LSU, and known physical separation between the motion trackers on the rigid L-Frame, a geometric triangulation process may compute the 3 dimensional coordinates of the first LSU. At step 1008, the location of the LSU may be calculated based on the transmitted readings. Two motion trackers on the L-Frame 802 may be sufficient for computation of the LSU locations, yet three motion trackers allow for redundancy and error checking (i.e., Origin—Long, Origin—Short, and Long—Short). The coordinates of the LSU may be calculated in a global coordinate system relative to the corner of the L-Frame 802 with directions parallel to the long and short calibration frame arms. In this manner, the 3D coordinates of every LSU in the volume may be stored in the system software and referenced each time the software commands the corresponding LSU to illuminate.

With the system software, the newly computed LSU location may be rendered as a green icon in a wireframe representation of the motion-capture volume in 3D. As each LSU is located and calculated, it too may be placed in the 3D preview. The L-Frame 802 and its motion trackers may also be shown in the 3D preview.

In some embodiments, for LSUs that are located on the floor or in other locations where it may be difficult to obtain a line of sight between the LSU and the motion trackers on the L-Frame, a secondary portion of an example calibration process may be invoked. An LSU with sub-threshold location accuracy, as determined by preset values in the system software, may be displayed in red in the 3D preview, near the best-approximation location. If no 3D location approximation is possible, the non-located LSU may be displayed in a list of items, in a side panel adjacent to the 3D view.

Such secondary calibration may continue from the standard calibration with each LSU still flashing in the same 20 microsecond on/off preset sequence. The operator may pick up the L-Frame 802 and point the side of the L-Frame 802 with the motion trackers toward the unresolved LSU. The operator may hold the L-Frame, in a relatively motionless position, to present the motion trackers to the missing LSU until enough light system cycles occur to reliably compute the 3D coordinates of the missing LSU. The system software, utilizing the data from LSUs with known 3D coordinates, may track the 6DoF of the L-Frame 802 as it is moved. Then the coordinates of the unknown LSUs may be computed, via the intermediate transformation of coordinates from the 6DoF information of the L-Fame relative to the GCS origin set in the first calibration step. The 3D preview may change the color representing each LSU to indicate to the operator whether each LSU has been successfully located or not. The operator may check in the system software that all LSU coordinates have been computed. The system software may clearly indicate which if any LSU do not have coordinate data and prompt the operator to rectify that situation, by bringing the L-Frame 802 back into the volume such that the system software may extract more data on the missing or weak motion tracker coordinate data.

Figure 11:
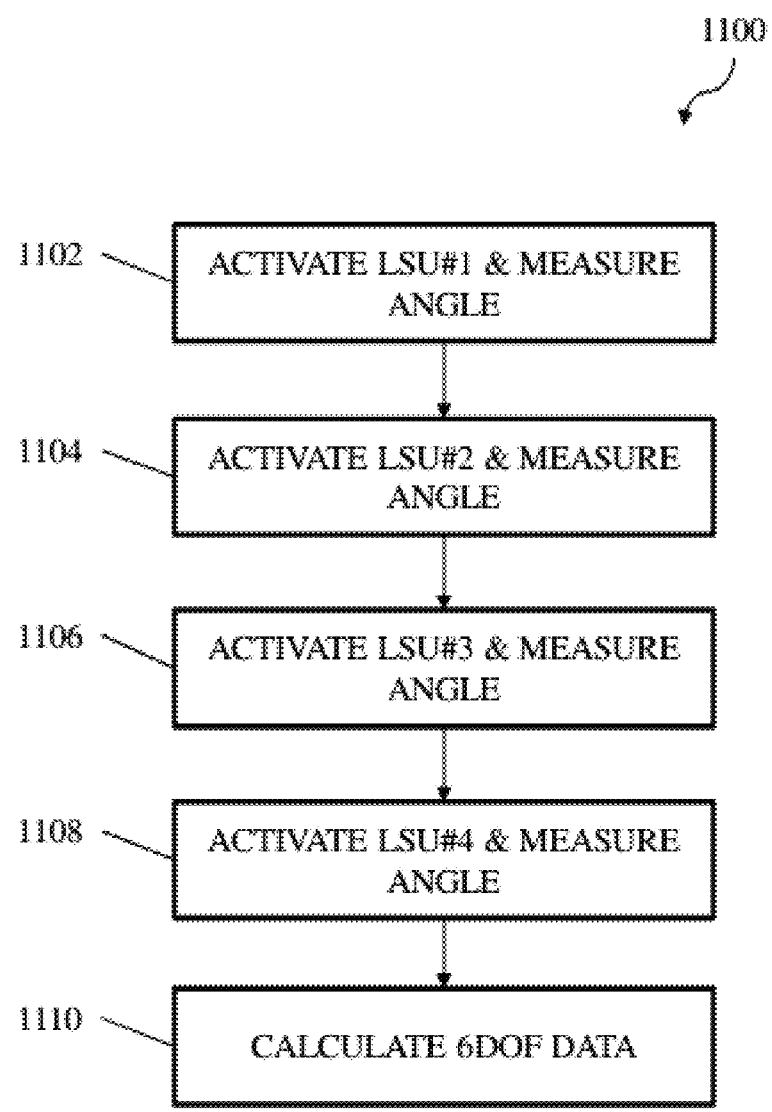
FIG. 11 is a flow diagram illustrating an example method of motion capture, according to some embodiments of the present disclosure.

FIG. 11 is a flowchart showing a method of motion capture 1100, according to some embodiments of the present disclosure. At step 1102, a first LSU may be activated and a motion tracker may transmit data that allows calculation of the 2D angle in the local coordinate system (LCS) of the motion tracker to the known coordinate location of the LSU #1. This yields the two angles between the motion tracker and the LSU. The distance between LSU #1 and the motion tracker may not be required, although light intensity could approximate the distance between motion tracker and LSU #1, if the power of LSU #1 is known. If the exact direction of LSU #1 to the motion tracker is unknown, and it could be anywhere on a sphere surrounding the LSU, no GCS coordinates or rotations of motion tracker may be determined without additional input.

At step 1104, a second LSU may be activated and the motion tracker may transmit data that allows calculation of the 2D angle between the LSU and the motion tracker in the LCS of the motion tracker to the known coordinate location of LSU #2. Thus, in a triangle among LSU #1, LSU #2, and the motion tracker, one side and one angle may be known. The distance of the motion tracker from the line between LSU #1 and LSU #2 may be calculated via triangulation between the three objects. The motion tracker may be anywhere on a circle of known radius perpendicular to the line between LSU #1 and LSU #2.

At step 1106, a third LSU may be activated and the motion tracker may transmit data that allows calculation of the 2D angle between the LSU and the motion tracker in the LCS of the motion tracker to the known coordinate location of LSU #3. This third observation may allow a second triangle construction (LSU #2—LSU #3—motion tracker). A coordinate system transformation may be performed from LCS of the motion tracker into GCS of lab and LSUs #1, #2 and #3. The intersection of 2 circular equations, so determined, may result in two 3D coordinate locations, and the intersection closest to the origin of the GCS may be selected. The angles of motion tracker may be taken from the three pairs of angles read during previous measurements. 6DoF of the motion tracker may be set.

At step 1108, a fourth LSU may be activated and the motion tracker may transmit data that allows calculation of the 2D angle between the LSU and the motion tracker in the LCS of the motion tracker to the known coordinate location of LSU #4. This fourth observation may allow LSU #3—LSU #4—motion tracker triangle computation. Since 2 circular intersections occur, the solution closest in 3D space to the prior motion tracker location may be selected. The 6DoF data may be updated.

At step 1110, after the four measurements and calculations, the final 6 DOF data of the motion tracker may be calculated.

During active collections of motion-capture data, the computer system may combine the time at which each LSU turns on and the location where the LSU is located in 3D space, as well as how the LSUs are oriented and propagating light. By this combination of time, space, and layout, each motion tracker may indicate its current orientation relative to each LSU in series, and, by the time a motion tracker unit makes 4 measurements, its 6DoF data may be realized. In some embodiments, the motion tracker may only measure 200 degrees of angular excitation, and there may be instances where the 3 measurements required to determine the 6DoF may be not in sequence. Thus, interpolation may be introduced to correct for excitations of a motion tracker due to occlusion or other failures to obtain line of sight between a motion tracker and the lighting system unit at a particular instant. The computation, even with 3 sequential measurements, may be based on a serial computation where linear predictive estimates may be employed. Thus, once an initial computation of 6DoF data is made, no accelerations greater than 1000 meters per second squared may be accepted, and no large shifts in displacement or orientation may be accepted. Also, the last location, current location and predicted future location of the motion tracker may be known.

The LSUs may turn on and off at microsecond intervals, with no delay between pulses. The LSU may operate in a seek/standby mode where the location and the number of clusters in its configuration may be transmitted for each LED. Whichever cluster may be recognized initially becomes the first LED of its local group of clusters to be illuminated. As other LED clusters in the group get recognized, the cycle of cluster on/off pattern increase speed such that each recognized cluster signature may be added to the list of known 3D coordinate points that each particular recognized cluster has shared. Each new LED cluster may cease to flash it's coordinates or ID, and simply turns on and off at a prescribed time interval following the master LED up to a number divisible by the total number of clusters in the group. Once 4 lights have been recognized and added to the light sequence, the 6DoF of a sensor may begin to be computed uniquely. The light system may operate in this mode preliminarily, to initialize the 6DoF of each motion tracker in the volume. As the 6DoF of each motion tracker is determined, the system may select a standard operating mode.

A metaphor of how the system operates may be the tightening of lug nuts. In a five bolt pattern, a first bolt may be tightened, then its most opposite may be tightened, then across to the third bolt most opposite to both the first and second, then the fourth and finally the fifth. This forms a 2D pattern. Using this metaphor as a method for the sequence of 3D light flashing, the first five lights to flash in such a system may be a base light near a computer system, then the light most distal from that base light in 3D space, then a point distal to both the first and second light point, and so on. The maximal distance from light source to light source may cycle until all lights in the system have lit once. This initial cycle of flashing light units may allow a low frequency cataloging of the 6DoF information for each motion tracker in the light saturation area, thus allowing for a specialized LSU flashing pattern designed to capture as many motion trackers at the highest sampling frequency possible. This scheme of light flashing may then be optimized to create the widest dispersion of lights illuminating in sequence surrounding the greatest number of motion trackers. As such the largest number of motion trackers oriented with their light sensitivity aperture or arcs facing a group of light units may allow the greatest number of light readings by the greatest number of motion trackers, with the largest apparent separation between light units, as the greater the apparent separation, the more robust the computation of each triangulated location of a motion tracker may become.

In this embodiment, once the cycle of all lights is passed, and 6DoF is computed for each motion tracker, the pattern of flashing may change. This change from all lights flashing in series to subsets of lights flashing in series may allow an increase in the sampling frequency of each motion tracker if desired. By considering the motion trackers in FIGS. 8 and 9 with a 200 degree hemispherical detection angle and the 6DoF of each, the system may compute the light sources at the location most visible by all motion trackers. These lights may flash preferentially.

Second, in one embodiment, to best track a single motion tracker five lights within the 200 degree visibility cone of a specific motion tracker may light in as close a timeframe as possible. These 5 lights may be selected to maximize the apparent angle between the motion tracker and the light. It may look like the 2D image attached above. In this way the five light activations detected by the motion tracker occur near in time and at the greatest angular departure from the light source neighbors.

Third, in one example embodiment, a set of non-common lights may be programmed to flash simultaneously, such that two (or more) data points may be acquired at the same instant in two (or more) separate groups of motion trackers. This may be visualized as a person wearing a suit covered with motion trackers, and the lights on the left may potentially be flashed at the same time as lights on the right side of the body, as the motion trackers on the left may be occluded by the body (and the physical limits of angular sensitivity–200 degrees) such that lights on the opposite side of the room may be not detected, and may serve to excite other groups of motion trackers chips facing that general direction. Furthermore, individual motion trackers may measure these non-common LSU lights simultaneously if the orientation and position of each motion tracker allows. Since a motion tracker may have 4 (or more) discrete light direction detecting chips built into it, intentionally selecting LSUs in the system to flash that strike different chips on the motion tracker (likely on orthogonal or opposite walls of an LSU setup) enable a motion tracker to take readings from two, three, or more LSUs simultaneously. This may allow a parallel mode of data capture to be taken preferentially over serial data interpolated to a master frame rate. Non-common LSU operation may begin after each motion tracker has an established 6DoF initialized and may be controlled by the system software.

In some embodiments, two or more motion trackers may be affixed to a single rigid platform such that the known layout geometry of the motion trackers may facilitate extraction of the platform's 6DoF, including velocity and direction of the platform from fewer than 4 light signals. This may be similar conceptually to the calibration frame, yet the platform may be fabricated small enough to allow unimpeded movement dynamics of the object the platform is attached to, for the purposes of motion capture.

In some embodiments, motion trackers may be always on and actively measuring light strike angle. Once a motion tracker detects two 20 microsecond light pulses from two different directions (incoming angles) within 1 second, the second pulse may be measured and the data may be broadcast via RF with a "Hello, serial number xxx motion tracker may be here" signature. Each subsequent 2D angle measure may be transmitted along with serial number of the motion tracker sending it.

The motion tracker trajectory in 6DoF may be conditional, and checked for plausibility, by limiting the moment-to-moment 3D displacements and 3D rotations to lower than user selected maximums. The motion tracker for instance may not be allowed to rotate 180 degrees, or translate 1 meter between two measurements less than 10 ms apart.

In some embodiments of the system, the LSU, motion tracker and the system software may be serial. This means only one reading between motion tracker and LSU may be made at a time, and motion of the motion tracker occurring between one discrete measurement at one LSU and the next measurement at a nearby LSU may induce error into the 6DoF solution. Subsequent readings by the motion tracker at each LSU recorded as part of the capture process may have the option to be linearly interpolated in order to approximate a synchronous recording. These measurements may then be brought to a master collection frequency with a single frame rate similar to other types of motion capture. The linear interpolation of direction toward each LSU may be performed on the two angles recorded from the motion tracker recording data.

In some embodiments, system software is provided to collect the motion tracker data and assign each 2D measurement to a particular LSU. The system software may then perform linear interpolation on the two angle data sets at each LSU, at user-defined limits. The limits on interpolation may define a default set to fill data gaps of no greater than 1 second (to be determined). The primary use of interpolated data may be to bring the computation of the 6DoF of a motion tracker to a master frame interval. The second function of interpolated data may be to add error checking to the 6DoF motion tracker data, by creating additional triangulated solutions from data points missing from an LSU that was seen by the motion tracker, was occluded from the motion tracker, and reappeared to the motion tracker.

System software may respond and start recording 2D angle information from each subsequent 20 ms LSU pulse. After three successful 2D angle measurements paired with 3 LSU locations, an initial 6DoF motion tracker solution may be output. Based on the vector direction perpendicular to the 6 DOF plane of the motion tracker, and an angular detection range of 110 degrees (+/−55 degrees in four cardinal directions from this vector), a map of LSUs visible to the motion tracker may be created. The LSU locations within this cone of visibility to the motion tracker may be then flashed referentially, along with a set of LSU locations slightly beyond this scope, as the motion of the motion tracker may bring the LSU outside the initial cone inside a new cone in the subsequent frames. With 4 chip motion trackers, the cone of visibility may be increased to 200 degrees, with a central area of 20 degrees that may be read by both light-direction detector 702 pairs. These ranges increase with the more complex 8 light-direction detector 702 motion tracker of alternative embodiments. After two determinations of the 6DoF of the motion tracker, a prediction envelope may be created. The prediction envelope may take what the 6DoF was in previous measurement, what it currently is, and with a linear extrapolation predicts where it may be on the next measurement. Thus the LSU locations ahead of where the motion tracker may be pointing may again be given preference to pulse next, just as the LSU locations trailing where the motion tracker was facing may be de-prioritized.

In some embodiments, the system may have LSUs placed on all 4 walls, ceiling and floor. In some embodiments, the system may only have LSUs on one wall or part of a wall only. In some embodiments, a retail store may wish to have interactive single wall displays for augmented reality reflections of a window shopper to appear in their brand's apparel. Thus, the single wall or portion of a wall may house the lighting system. The sensing system may use multiple points of reference all situated in a single 2D wall or window surface. The motion trackers facing away from the wall may not pick up these light flashes, but enough motion trackers on the anterior of a person's body may be excited by the lighting system and create a mathematical description of the anterior facade of a person's body (in the window shopper example), with enough detail to allow the appropriate rendering of the augmented reality aspects onto a motive reflection of a person in real time. For example, the motion tracker may be temporarily affixed to skin or clothing or woven into the fabric (embedded) in clothing. This may give retailers a way to measure your body size and make custom fitted clothing for instance.

In some embodiments, a lighting system may be installed to a machine, such as an automobile, so that another vehicle equipped with motion trackers may measure the approach and proximity of the car with the lighting system for warning the driver or as an information source for an autonomous driving system. In some embodiments, watercraft and aircraft may have docking or landing facilities equipped with the lighting system, and ships, airplanes and helicopters may have a single or multiple motion trackers to sense their position and orientation relative to the LSUs, again as a collision warning system, or for future autonomous navigation and docking systems. Lighthouses along shipping routes may be information sources for the motion tracker based motion-capture system. In these scenarios, individual lights at a distance may appear as a single light source, and a motion tracker motion-capture system may detect orientation relative to that single light source (appear as a single light albeit flashing as individual lights). As a vehicle (land, air or sea), approaches the facility or another vehicle with a lighting system and the individual light sources may be discriminated from one another (placed to maximize inter-light source distance), the full 6DoF data of the motion tracker thus relates the orientation of the vehicle with the motion tracker system to the position and orientation of each and every other vehicle (or object) equipped with the lighting system.

In some embodiments, the lighting system may be incorporated into a television display. A liquid-crystal display (LCD), or individual pixels formed in other technologies, may flash with a signature pattern to identify its position to a pair of eyeglasses or other head mounted device equipped with the motion tracker motion-capture system. The lighting of pixels in the display (e.g., near each of the four corners of a rectangular display) may allow calculation of the viewer's position and orientation relative to the viewing medium (screen) with 6DoF. With this information, 3D display elements may be inserted into the video content on the screen being viewed to allow a 3D view of the image and perhaps virtual reality interaction. In addition to adaptive, external LCD screens, transmitting the 6DoF of the motion of each eyeglass lens surface of a wearer to a projector system, left and right video images may be directly painted on the lenses thus creating a 3D video effect. (The Texas Instruments digital micro-mirror device (DMD) may be one such technology.) With a wall mounted DMD, images may be presented to the eyewear of multiple wearers simultaneously with motion tracker lenses having 6DoFs. Alternatively, for users wearing the motion tracker eyeglasses, a smartphone could be built with a DMD instead of a screen.

Figure 12A:
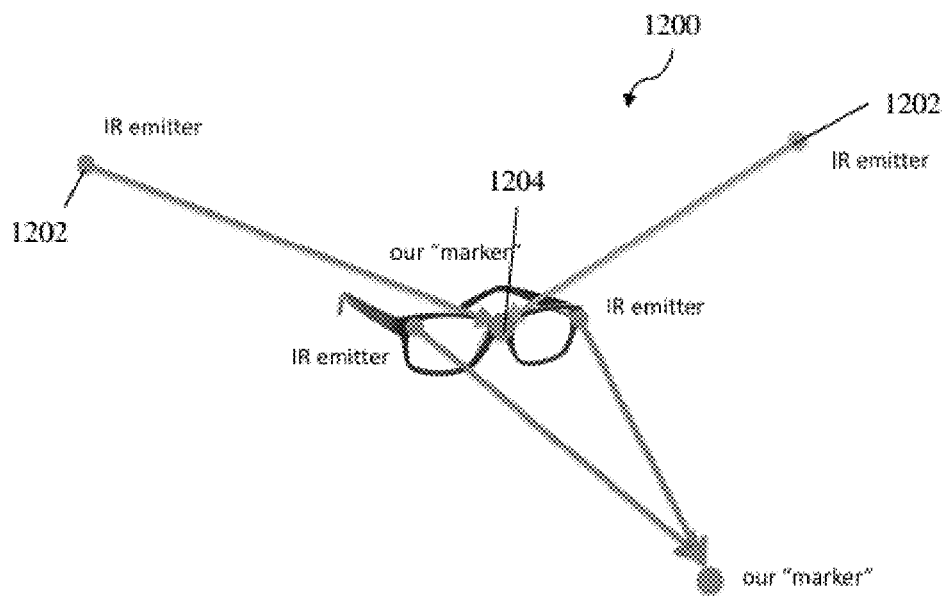
FIG. 12A is a view of an example motion tracker mounted on an eyeglass frame, according to some embodiments of the present disclosure.

FIG. 12A shows an example motion-capture system 1200 with a motion tracker mounted on an eyeglass frame, according to some embodiments of the present disclosure. In some embodiments, a small lighting system (up to 10 individual lights) 1202 and a motion tracker 1204 with LEDs may be attached to an eyeglasses frame. With the ability to receive and transmit 6DoF of each eyeglass lens relative to each of the wearer's eyes, augmented reality systems may project correct stereoscopic imagery onto the lenses for the wearer as rendered digital information. To present to proper stern imagery on a pair of eyeglass lenses, knowledge of the Point of View (PoV) of the wearer is necessary. A frame mounted pair of RayIQ microchips delivers stereopsis without cameras to ascertain the glasses' and wearer's PoV. Furthermore, the 6DoF of the eyeglass frame mounted lights may then be used as a system-within-a-system to enhance finger tracking. The flashing of LSU LEDs on an eyeglass frame may be patterned in timing and spatial layout (arrangement of LSUs on the frame) to provide a signature ID to authenticate users or provide password access to software, and devices (smart phones or door locks as examples). Similarly, the ID flash of a wearer's eyeglasses may selectively allow or block advertisers from presenting content, based on the wearer's opting into promotions etc. As IR light overwhelms video capture, the flashing of LSU on eyewear may be patterned to serve as a privacy screen from unauthorized cameras and may be synchronized to allow authorized image capture. Using RayIQ instead of cameras for PoV tracking eliminates privacy concerns induced by cameras.

Figure 12B:
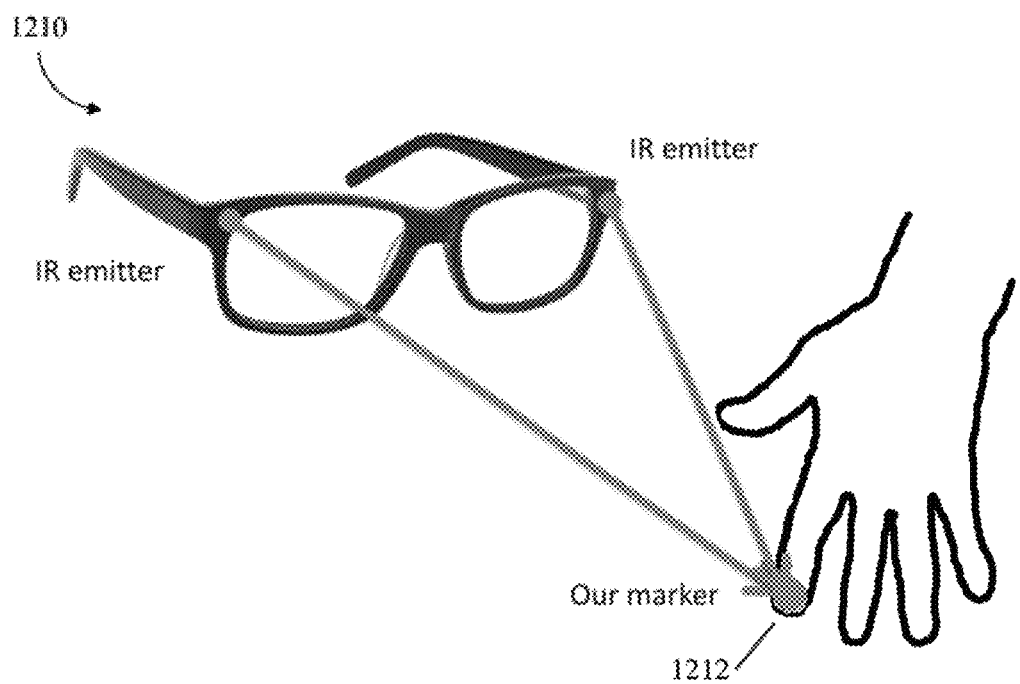
FIG. 12B is a view of an example motion tracker mounted on a human fingernail, according to some embodiments of the present disclosure.

FIG. 12B shows an example motion-capture system 1210, according to some embodiments of the present disclosure. In some embodiments, the motion tracker/LED unit 1212 may be glued to each fingernail. The finger (and toe) nail devices with motion tracker/LED and bending/vibration of the nail bed operate as a response to 6DoF configurations and motions of the fingertips, but also may operate on a programmable schedule to vibrate or provide bending specific types of signals to the wearer. One type signal would be an alarm, or alert to wake the user in the morning, with a gentle pulsating of the fingertips. By alternating which finger vibrates or bends, specific information may be ingrained in the pattern of alerts, such as the identity of a caller, or from whom an email or text message has arrived. These signals may be repeating patterns of stimuli. These signals may serve as general notifications or reminders from a wearer's calendar, email, web search results, phone calls, and likes, but also the vibrations may and may be patterned to illicit physiological effects, including but not limited to scalp hair re-growth. In some embodiments, by creating a cascade of vibrations and bending moments on each fingernail in sequence or simultaneously, the effect of a nail rubbing (or "balayam") practice may be delivered without the need to remember to perform the practice, or to perform the practice manually at all. Furthermore, to enhance the sense of touch, stochastic resonance vibration patterns may be embedded at sub or supra sensation thresholds, which have been shown to improve lower the tactile sensitivity threshold and when applied to the feet, the elderly show reduced postural sway. In some embodiments, the haptic fingernail may perform the function of touch without touching.

In some embodiments, the lighting system may have the shape of an arch or arbor, with a constant or non-constant radius, shaped to fit the needs of the application. This setup may allow a mobile lighting system to be placed over and above a piano keyboard, for example, so motions of a performer's hands may be captured when motion trackers are affixed on each finger segment (or simply on each fingernail) while they play the piano. In some embodiments, an arbor of lights (or a pair of arbors) may be placed facing the frets on the neck of a guitar, and motion trackers may be placed on the body for study of a performer. In some embodiments, a similar arbor of lights may be used for other instruments such as clarinet, oboe, saxophone, trumpet or violin.

For use in reality-based animation, the sensing system may have a small form factor such that it may be applied to an actor's body and face, to give an animator much more exact data, namely the rolling, pitching and twisting of the skin's surface during the unique expressions of a character, which exist beyond the simplistic 3D positional data. The sensing system may narrow the uncanny valley and bring hyper-realistic animations greater believability and a more natural appearance. This ability may be unattainable with 3DoF systems, and also serves to greatly simplify the process of tracking the major segments of the body in 6DoF as a single sensor may be attached to the midpoint of a segment instead of a triad or group of four as historically practiced.

Capturing the curl of the lip, or the pose of a fingertip, may be easy to accomplish with a few motion trackers strategically attached. When the shadow across each pair of light-direction detectors 702 may be read, cast by at least 3 individual light sources, it extracts both 3D position and the 3 angular descriptions of that a single point, thus the user gets twice the information from one discrete location. Importantly, the motion tracker may function as part of a stand-alone system as it does not need to be hybridized with inertial motion sensors or other separate systems, which often yield inconsistent results.

The lighting system units may be added to improve the function of an existing motion-capture systems, such as those produced by SiMi® Reality Capture Systems GmBh. The SiMi® system has ring lights but they may be primarily used during their calibration procedure and not during collections. One SiMi® product called Shape uses the camera system to capture the silhouette of a human actor inside the FoV, by background subtraction. The SiMi® Shape system uses 8 cameras, and the data output may be a result in combining these 8 silhouettes. By alternatively flashing the LED rings on each of the 8 SiMi® system cameras, and by flashing LSU added to the periphery of the volume, shadows that may be cast may be collected as part of the standard video frames of the measurement. Each of these cast shadows may be the projected result of the light interacting with the human in the volume. The silhouette tracked model built by SiMi® Shape may be likewise be projected onto the walls and floor of the volume, determined by the point light sources of the SiMi® camera LED rings and LSU. To utilize this added data, the flat surfaces in the lab must be mapped during the calibration process (walls, floor, ceiling, furniture, etc.), and measurements of light absorption added. Non-absorptive or transmissible or reflective surfaces or irregularly textured surfaces may not create an adequately defined shadow. Some cameras may not be positioned to see both the human actor and the cast shadow from other light sources. Thus a comparison between actual shadows on the walls and floor in the video file may be made with the shadow projection from the 3D SiMi® Shape model. Bringing in extra LSUs effectively increases the number of shadow silhouettes while keeping the SiMi® Shape system at 8 cameras. Furthermore, the 2D appearance of the shadow cast by the LSU or the SiMi® camera LED ring may be native to the LCD chip used to capture the video images, and a direct transformation may be made from shadow projection to image. The LSUs may be placed into the SiMi® system at locations that cast the shadows containing the most information for given human postures and activities, locations that may not be ideal for camera placement.

Figure 13A:
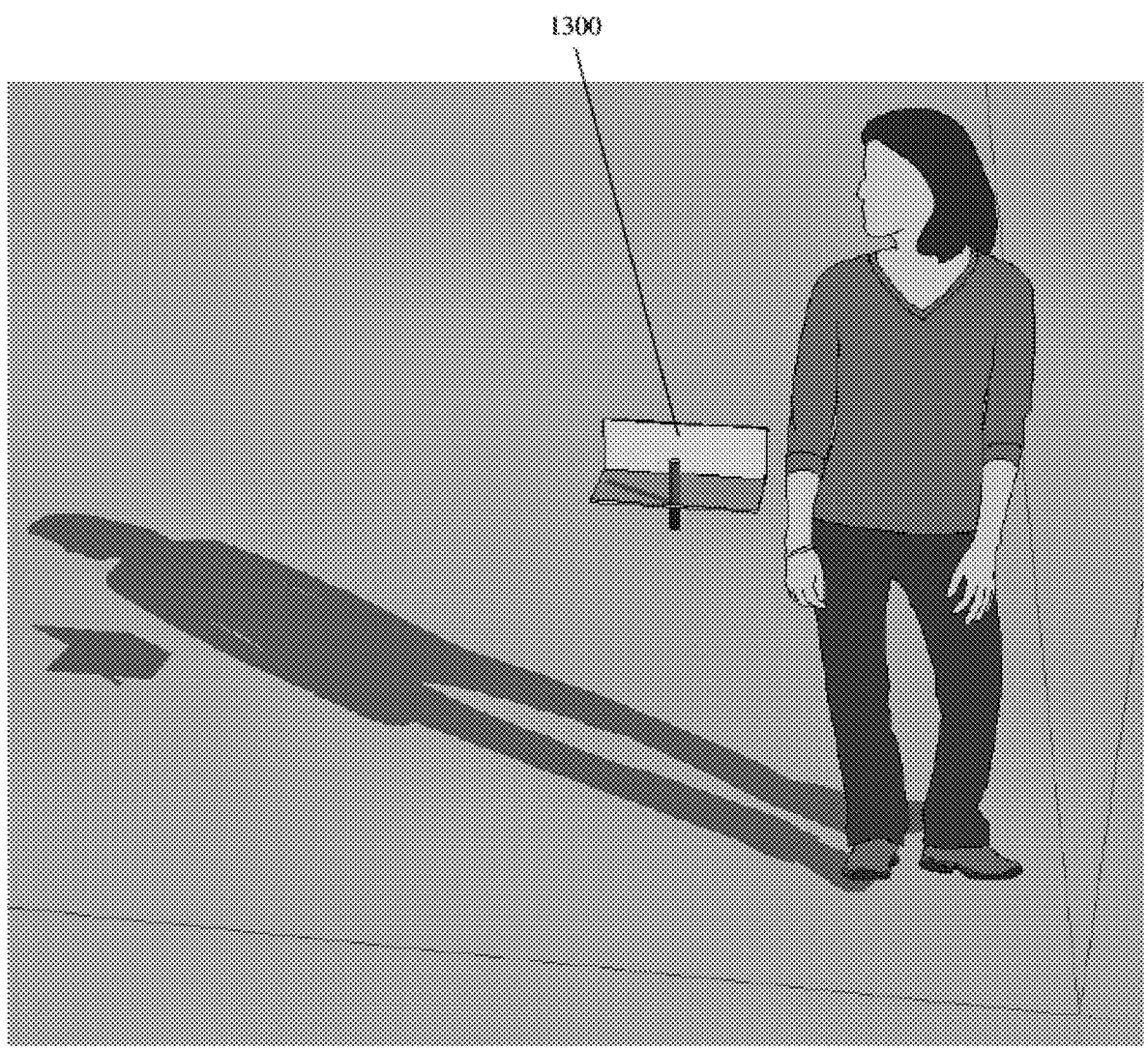
FIG. 13A is a view of an example calibration tool, according to some embodiments of the present disclosure.

FIG. 13A shows a calibration tool 1300, according to some embodiments of the present disclosure. The shadow box calibration tool 1300 may allow the verification of light source location (both LSUs and SiMi® LED rings), and consists of a cylinder on a handle, and a two-sided box with a floor and one wall at 90 degrees. This device allows measurement of the shadow cast by the light source with the known geometry of the box casting the shadow and the dimensions of the surfaces that the shadow is projected upon. From these measurements, the 3D location of the light source may be computed, and then utilized in subsequent SiMi® Shape recordings of a human actor.

The hybridizing of the SiMi® Shape system with LSUs and motion trackers, the SiMi® silhouette tracking, the projected shadow tracking, and the body surface tracking may all happen concurrently and in a manner that serves to reinforce the quality of the whole-body, motion-capture output.

Figure 13B:
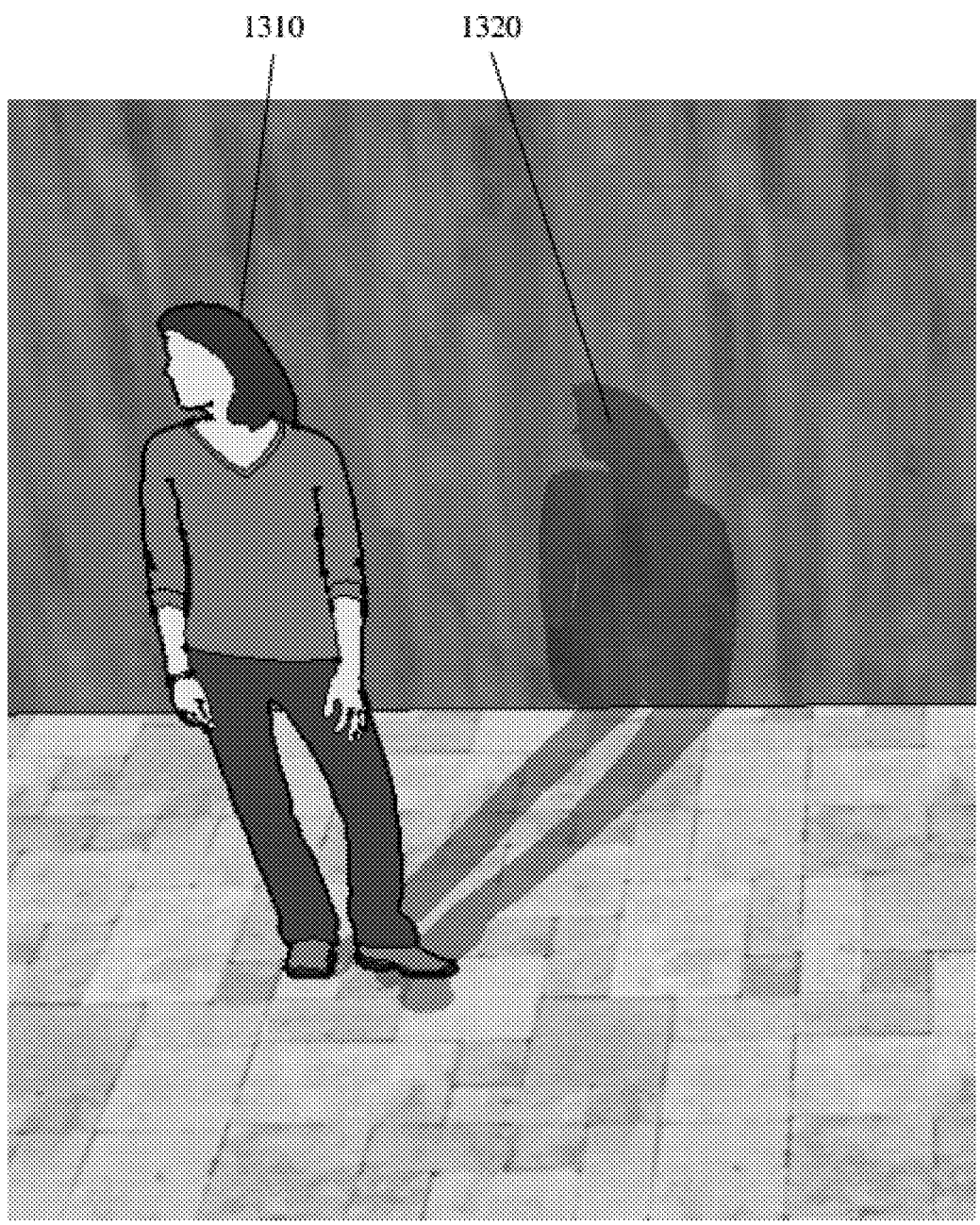
FIG. 13B is a view of an example silhouette effect, according to some embodiments of the present disclosure.

FIG. 13B shows an example silhouette effect, according to some embodiments of the present disclosure. The light source creates a shadow based on the curved surfaces of the human body 1310, and the shadows 1320 are cast on the wall. These shadows may be transformed back to silhouettes at the actor's location and may contain segmentation not apparent in the direct view of the subject (i.e. arm/torso). The curvature of human limb segments may be thus added information beyond the intersection of silhouettes that rely on assumptions of roughly cylindrical segments.

The benefit of hybridizing the motion tracker with onboard LEDs, and a camera-based motion-capture system such as SiMi® Motion may be that with the motion tracker LED active and being tracked in 3D by 3 or more cameras, a single light direction measurement may be sufficient to determine the 6DoF of the motion tracker, thus enabling 6DoF data capture in a parallel mode at the master frame interval, and avoiding the interpolation errors that may occur during stand-alone serial capture of motion tracker data. The downside may be as always, cost of the camera-based system.

Some embodiments described herein may provide sensor fusion between a multi-plane LDD sensor that reports a 3D unit vector of direction with a magnitude equal to net and differential light intensity, an Inertial Measurement Unit (IMU) comprising a 3D linear accelerometer paired 3D rotational acceleration gyroscope sensor (and sometimes with a 3D magnetic field sensor or magnetometer), as a 12-axis sensor and with an Infrared Emitting Diode (IRED) built into one microchip. The sensor fusion may be accomplished at varying levels of multi-plane LDD sensing contribution from one light source up to 3 or more.

One or more such embodiments may act as an independent mocap system when there are at least three light sources with or without digital power control, in the vicinity of a single LDD sensor. The output of a single LDD sensor delivers a pair of 2 signal channels, which may be the sensor-local and orthogonal xz and yz angles. The xz angle is the sensor local ordinate direction, and the yz angle is the abscissa. This angle pair can be represented as a sensor-local 3D unit vector with an origin at the center of the LDD sensor. The photoexcitation level of the photodiode arrays on each side each wall in each array plane of measurement may be ascribed as a sum relating to the net light intensity. The photoexcitation on each side of the wall array can be used for a differential measurement that relates to the arriving light direction. Three LDD readings of three light sources, each at a known 3D coordinate point allow full six degree of freedom (6DoF) computation of the LDD sensor independent of any other fused sensor. Three-point LDD 6DoF computation may be accomplished as described above. Multi-plane single LDD sensors may be referred to as Angle of Arrival (AoA) sensors.

As the LDD sensor may be moving during operation, different light sources in the periphery may enter the LDD sensor field-of-view (FoV), and by the same mechanism (the movement of the LDD sensor in 6DoF) other light sources may exit the LDD sensor FoV during normal operation. If the dynamics of the LDD sensor causes this entry and exit of lights into the FoV of the LDD sensor, that LDD sensor motion may utilize more than the minimum number of 3 light sources with known 3D coordinates. Any number of additional lights may be present in the vicinity of the LDD sensor, and the 3D coordinates of each may be mapped.

For example, coordinate mapping of lights to be included in the system may have occurred prior to dynamic motion capture by using an instrumented L-Frame with 4 two-plane LDD CMOS sensors arranged with one at the vertex (origin), one at the end of the short arm of the L and two on long arm: one at the end of the arm and one at a point ⅓ of the long arm length from the origin, or with video cameras performing SLAM (Simultaneous Location And Mapping) or other stereopsis pair of cameras or single camera image based mapping technique. With the 3D coordinates of the system lights inside and around the volume measured and in memory, each light may be assigned a unique identifier. The ID of each light may be transmitted by a coded pulsing of the particular system light. The 3D coordinates and the light ID may be stored onboard the IC memory of the mobile device. In another example, a method to map light source 3D coordinates may include the use of room-mounted system lighting devices that have a LDD sensor mounted adjacent to a LED fixture. In this way the LDD/LED system devices can preclude the need for the temporary use of an instrumented L-Frame by reciprocally mapping each system device by an alternating mode of LDD measurements to line-of-sight accessible LEDs, and LED activations which in turn are measured by system LDD devices with line-of-sight to it. With the L-Frame method, the stereopsis camera method, and the LDD/LED system device method of calibrating the measurement volume, all system lights in the vicinity may be measured, mapped and given an ID specification regardless of if they are part of built LDD/LED system devices, independent light source only, or part of a rigid array of LED fixtures wired together into a system lighting apparatus. For standard "always on" lights (LED, incandescent, or other), cameras using SLAM can locate them in their fixture(s) as they will contribute additively to the net shadow present at all times, and predictive tracking of the LDD sensor may reveal periods when these lights may be the principal casters of shadow on the LDD at its given orientation and position inside their light steradian(s). Additional camera SLAM operations can locate room windows and glass doors that may admit ambient light from adjacent room(s) or the outdoors during daylight hours (the sun). Even general information on the lighting conditions inside a mocap volume may be included that can be described as the "light-shadow-map" of a space, built from SLAM or other apparatus (L or T frames with LDD sensors) utilized to characterize all light conditions inside the prescribed mocap volume. Lighting conditions characterization can include for example all present point and panel lights, which lights can be strobed, and the Sun and Moon as they enter the space through doors or windows with massively parallel rays at a specific angle that is coupled with time of day, date and location on Earth. When multi-plane LDD(s) operates in lit spaces where no single light(s) has digitally controllable intensity the LDD(s) act as light angle and intensity rate-sensors, measuring changes in light intensity and net direction.

While the system may use three light source readings to compute 6DoF independent of other mocap systems of components, the system need not rely on making repeated LDD readings to the same three lights. If for example one light exits the LDD FoV, by parallelizing the serial LDD measurements using linear interpolation or curve fitting to earlier LDD reading of that light, prediction of new LDD readings to each other light and other mathematical means of estimating the contribution that three separate in time LDD readings can contribute to an instantaneous measurement of LDD sensor 6DoF. System sensor devices may be created with known physical properties, for example including the location of the device center of mass and known values of rotational inertia relative to the three principal planes of the device. By factoring in the inertial properties of the system sensor device, and once the system devices are initialized and have begun tracking the dynamics of an attached object, the total inertial properties of the system device and tracked object, including any and all influences due to linked rigid-body segments connected to the attached object, deliver a loosely constrained range of modeled expected accelerations and rotations. The maximum expected limit of linear accelerations and angular rotational accelerations based on the preceding recorded dynamics, and all stored libraries of reference object motion that describe similar linked rigid-body dynamics, can be utilized to place limits on how much the LDD system device can be expected to have moved between LDD readings. The previous behavior of the system device may be plotted in system memory in all six dimensions (local and global X, Y, Z, roll, pitch, yaw) and, with a linear prediction and and/or with a 2nd order equation or spline prediction, the potential next 6DoF solution may be predicted. This prediction may be cross checked with the limits on linear translation and angular rotation to ensure the prediction is physically possible based on all that is known about the inertia of the system device and the system device plus motion capture object as a unit (shared inertia). The LDD device can deliver geometrically relevant direction data to the resulting capture. When system lighting line-of-sight drops to a single light source, preceding 6DoF with ascribed limits on possible translations and rotations can be leveraged to continue accurate 6DoF computations with limited veracity. The 6DoF computations made from a single light with predictive system device plus mocap object inertia may retain true measurement capacity in all but one direction: the distance along the path from light source to LDD. Increasingly accurate distance estimates are possible based on existing knowledge on system light power, the shape(s) of each light emission, the LDD photo net and differential intensity, and resulting knowledge on the angle computed between the light and the principal plane of the sensor circuitry, and the estimated location of the sensor within the steradian or other shape of light emission. All influence of system device/mocap object inertia may be directed to solve for and describe any departure from measured 6DoF in this one dimension: along the line from light source to system LDD. In the case where only one system light is visible to the LDD for a period of time, cases where the inertia of the system device/mocap object must be factored in may be flagged on the time series record of results as potentially un-verifiable. Furthermore, when a second or third system light is again visible, a backwards recursive trace on system device 6DoF may be employed to smooth any discontinuity formed by one-ended predictive estimates, as both tangent directions of each of the 6DoF data records will be known and "gap filled" accordingly with first a linear fit and then by a spline or 2nd order power law fit per channel. This mathematical parallelizing of serial LDD measurements may be necessary as the LDD sensor can be as a whole moving with its own dynamics with 6DoF motion while the sequence of serial measurements is occurring, as the LDD sensor is designed to be attached to moving objects of interest.

Adding IMU sensor fusion at each serial LDD measurement augments the 6DoF output measurement, by combining the IMU primary (native) function of 6DoF acceleration measurement, by in-software integration of those accelerations to estimate 6DoF sensor linear and angular velocity, and again to estimate 3D position and the three rotations of orientation, with direct measurement of specific 3D angles in directions aligning the LDD sensor body with the light that is shining on it. The IMU strength is quantifying change of state. An IMU measures change in state over time of acceleration very well, somewhat less well for velocity, and quite poorly for position owing to sensor noise amplified by subsequent integrations and the lack of the integration constant required to determine each of the 6DoF position solutions. Furthermore, when an IMU is at rest, or near rest (stationary), little to no change in acceleration is occurring and sensor drift increases more rapidly, making LDD measurements more useful.

By taking advantage of the native function of the IMU in an LDD/IMU sensor fused computation, the change in sensor state between serial LDD measurements in terms of dynamic accelerations and velocities may be used to aid in the parallelization of LDD measurements. When the LDD/IMU is stationary or nearly stationary, the serial LDD measurements may need less sensor-local motion artifact correction and may directly aid the IMU in measurement. The motion of the LDD/IMU device can be accounted for between LDD readings with a complete IMU reading at each serial LDD measurement. For example, the unified coordinate system made possible by creating an LDD/IMU sensor as a monolithic device can store on board (e.g., in firmware) the discrete and fixed geometrical separations between each component of the fused sensor: between the origin of each of the three directions of linear acceleration, each of the directions between rotational acceleration, and the plane LDD. The triangulation of light direction may be converted to a device or body-local unit vector and the three components (x, y, z) of that on-chip direction derived unit vector may be used to directly map each new measurement from the IMU channels that measure change of state to corroborate double integrated IMU displacement during IMU dynamics and supply a drift and distortion free IMU position when the IMU is at or near stationary as IMU channels accrue the majority of signal drift when they are not moving. A second LDD measurement made shortly after the preceding LDD measurement may be used to compare the two adjacent measurements of the body-local direction unit vector and using the first central difference, take the derivative of position for body-local translation and rotation velocity. Thus, the LDD/IMU device may be used to compare raw direction measurements with double integrated IMU measurements, pairs of directional measurement data via first central difference differentiation to singly integrated IMU data, and with additional LDD readings that allow additional body-local direction encoded 3D unit vectors for second central difference method LDD estimates of acceleration that are directly comparable to the IMU native data. In this way the LDD/IMU system corrects IMU measurements contaminated by drift and integration distortion by using line of sight measurements of direction that brings IMU data to the precision and accuracy standard of a camera-based optical mocap system.

The multi-plane LDD sensor is a physical Integrated Circuit device with mass and inertia. Furthermore, the LDD IC microchip is socketed and mounted on a Printed Circuit Board or flexible circuit board or other system for supplying power and ground and collecting measurement signals from the LDD in order to operate. Packages such as these are known in the art and/or may be developed. Each physical component added to the LDD microchip contributes to the inertial and mass of the LDD device in a specific way, and by using the known physicality of the LDD device as a whole to map the entire LDD sensor moment of inertia, and center of mass about all 3 planes relative to the xy surface plane of the LDD IC (z direction being normal away from the surface plane of the microchip) mathematical predictive models may be made to parallelize serial LDD measurements. For example, a detailed materials-based model of the system device including the PCB may include the density of the materials utilized, and the distribution of specific electronic components and their locations on the PCB. Each component has a mass and a center of inertia, and in an additive method of drafting the system device, each component contributes to the system device mechanical properties. For example, a radio device for Wi-Fi communication can be part of the production PCB device, and will have a geometric location on the PCB, and that information can be added to the geometric and inertial map of the system device as a unit. When other parts such as a plastic system device case are designed and fabricated, the inertial properties of the protective case can be modeled in software and checked in the prototype stages with manual device geometry mapping (either by touch probe mapping or an optical 3D scanner) to ensure the modeled geometry and mass distribution matches the physical device.

Once the LDD and lights have initialized to solve for the 6DoF of the LDD sensor, each additional LDD driven 6DoF measurement may contribute to a prediction of where the LDD was, where it is and where it might be at the time the next serial LD measurement is made. By adding the inertial constraints of the LDD sensor, predictions of LDD 6DoF at subsequent LDD readings are made more realistic. The system device can only move so far and so fast in translation and rotation, especially when the object of interest, which it is attached to, is of a far greater mass (and inertia) than the system device. The prediction of where the system device might be at the point when the next serial measurement occurs, based on the path of each of the six degrees of freedom (3 translations and 3 rotations) even with a simple linear prediction will bring a piece of data to the system computation that feeds into the solver that computes the most current 6DoF description of a system device. Furthermore, polynomial curves can be applied to each of the six channels of 6DoF data based on preceding results farther back in the time series of computed results, which can be used not only as the data record of 6DoF path, but also to predict the direction of each path as a forward estimate based on a tangential direction.

Adding an IMU to the LDD sensor either on-chip or mounted adjacent to the LDD chip forces the inclusion of the additional components and wiring connections in the whole device inertial properties, but those differences are accounted for in a LDD based IC of any format (with or without an IMU or other sensor such as GNSS or Global Navigation Satellite System). With the inertial properties of the entire device known, and with the collection of inertial based changes in trajectory measurements by the IMU, a more accurate and precise estimate of the 6DoF of the sensor as a complete unit is measurable and can thus be corrected for. Prediction estimates now become measured quantities, and output of the whole device 6DoF is a combination of LDD, device inertia, and inertial measurement by the IMU. This can be especially relevant in rotation measurements, which typically accumulate nearly twice as much error as linear acceleration measurements owing to the design of the devices. Furthermore, when measuring with the common consumer IMU "strap-down" type device, the error prone rotation measurements are first taken to orient the acceleration channels relative to gravity, embedding the error in the determination of initial conditions for translation measurement. By measuring the angle of the sensor directly, strap-down errors can be minimized, true acceleration orientation can be properly quantified, and further corrections such as the direction of gravity can be more effectively assessed. For deep space missions, tracking health by monitoring movement patterns is important, but challenges of using IMUs to do so are compounded by the lack of gravitational and magnetic fields, which IMU sensors enjoy on Earth. It is here that the aid of an LDD sensor assumes an even more central role in reporting the position and orientation of each sensor. Eyewear with an LDD on each hinge or endpiece, and an IMU at the apex of each arch crafted in each of the two temples that make up the glasses frame that has been approximated to fit along the top curve of each ear for wearing comfort, combine in a simple biomimicry of the human visual-vestibular system. By locating the LDDs near each eye, and the IMUs near each inner ear, digital measurement of innate human biological sensor fusion is accomplished.

With two (less than 3) lights in the FoV of an LDD sensor (either currently or entering) with known inertial properties of the sensor unit, and an IMU on-chip or on-board, the change in position as measured by the IMU supplements the 3D LDD reading to solve additional components of the sensor 6DoF motion. As two LDD sensor measurements result in a solution that is described as a circle in 3D space with a center point along the line between the two lights and with an orientation perpendicular and relative to that line between lights, there may be a strictly limited solution for the point on that circle of the measurement sensor, which is further reduced when supplemented with IMU measurements and other available prior knowledge. The closure onto the single solution of 3D position and orientation can be made possible by using the IMU data to estimate the discrete change in position and orientation of the system device between LDD readings. Thus, with two direction measurements made adjacent in time and the ongoing capture of the system device change in position and orientation from the IMU portion of the system device, a single resulting 6DoF is made. This combination of unit vector direction (from the LDD) and change in physical position and orientation (from the IMU) allows for continued tracking of the system device 6DoF once its initial state is mapped at the beginning of the time series mocap collection. When a lower number of system lights are in the FoV of the LDD, previously measured 6DoF data is utilized in a stepwise prediction of current state. As the time duration between LDD readings increases, the resulting data may be flagged with a color-coded confidence meter that ranges from green (high confidence as measurement has many recent optically validated measurements) to red (low confidence as measurement has IMU only validated measurements). These flagged regions can receive extra examination in software for massively gap filled optical data with continuous IMU data, but can be a simple linear detrending, for example. The 6DoF data confidence color-coding may also be based on the dynamics the system device is undergoing, as large amounts of device motion leverage the ability of the IMU channels to measure acceleration well, and the color-coding may be set towards the green end of the spectrum. Conversely, if the system device is at or near rest, and the IMU channels are not measuring sufficient accelerations, and the LDD data is sparse, the confidence color-coding may shift towards red (although a IMU determined lack of motion coupled with a LDD determined lack of motion combine to a relatively high level of confidence the system device is at or near rest and has not moved or changed orientation to a great extent). Machine Learning can be used to recognize patterns between these separate IMU and LDD channels. With the knowledge of the LDD sensor position and orientation within a SLAMed space, the LDD data can be verified by creation of a constructed image as if taken from the perspective of the LDD sensor, since the perspective and angle to the scene, and the informational content of the scene (lights, rigid objects in the map, etc.) are known. This gives a user a visually verifiable tool to spot-check the performance of the tracking performed by the LDD and lights.

Figure 14:
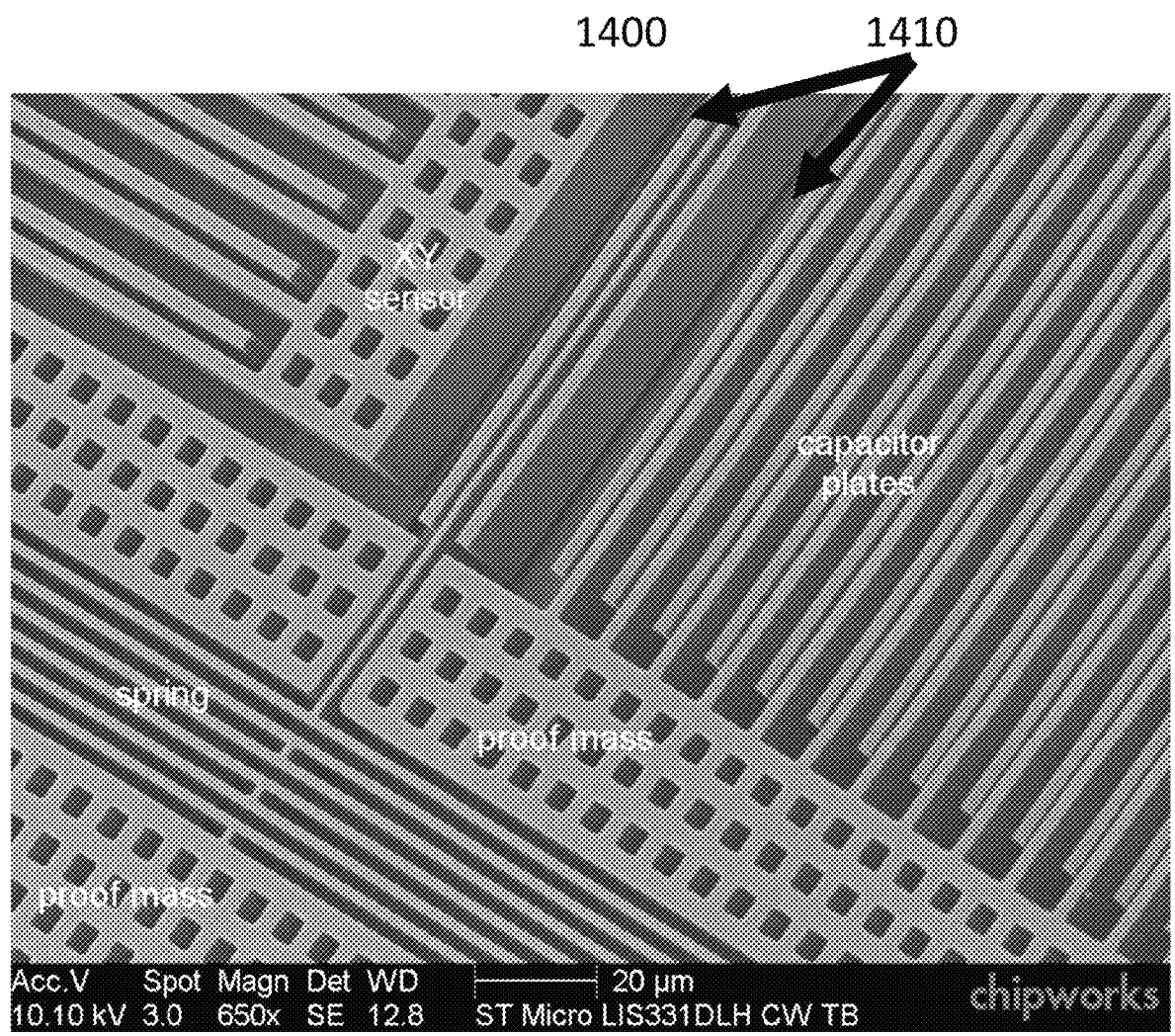
FIG. 14 is a view of an accelerometer circuit, according to some embodiments of the present disclosure.

Some embodiments may integrate the LDD and IMU as follows. FIG. 14 shows an accelerometer circuit 1400. Pairs of differential photodiodes may be placed in the troughs 1410 (e.g., at different scales) to measure shadow. This way when the accelerometer is at rest, it may be given (light) directionally verified orientation and position in a 3D volume. The bars and troughs may be open to the environment (and suitably covered) in this embodiment. The accelerometer local +x and +y directions may be derived on-chip and leave chip normal z unmeasured in light direction (still functions as our 3rd axial sensor). It may be possible to measure two angles because those two angles do give a 3D unit vector direction. The accelerometer beams may be allowed to bend up to their mechanical limits and/or design thresholds for the purpose of measuring a single plane of acceleration. The bending induces a current change at the sensing elements that may be distributed into capacitors that measure deflection as a change in charge state. The beams are part of the accelerometer proof mass that moves as a monolithic structure in one plane. Between the beams (on either side of each beam) a photodiode may be cast into the substrate beneath. By creating the proof mass composed of beams structures above the substrate embedded photodiode pairs on opposite sides of each beam and exposing the beam/photodiode to light, a shadow is cast onto one side of the beam or the other, depending on the light direction that a photo-differential measurement is realized for light direction detection.

Even a single light reading benefits the LDD/IMU sensor. The single light reading by the LDD sensor component may yield a 3D unit vector that emanates from the measurement center of the sensor and passes through a 3D location of known description, as well as a photoexcitation level based on arriving light intensity and spatial relationship between the light source and sensor. As the 3D unit vector is computed based on the LDD sensor body-local coordinate system, the 3D unit vector has meaning in the local coordinate system of the LDD sensor. While the direction to that light is known, the distance to that light is approximated based on light intensity. With a known distance to a light source the 3D unit vector becomes a 3D vector describing a 3D line from sensor center to light origin. The relative orientation of the line in global coordinates is not known from the LDD measurement alone, and only by sensor fusion with the IMU can the complete description of each line segment starting at the LDD and ending at each light be described in the global coordinate system. Having an LCS direction unit vector and a LCS based inertia-based description of the hybrid sensor device (LDD+IMU) gives the system additional means to "connect the dots" between sensor and measured light sources. Hybrid LDD+IMU sensors can be a single MEMS build or individual microelectronic components that are rigidly mounted into a single rigid device such as a pair of glasses. With directions to individual lights at isolated point in time, and the IMU measurements at those same instants, the change in 6DoF of the sensor may be compared, from both the optical measurements that lack inertial constraints, to software corrections based on the inertia of the sensor unit, to the measurements of change in motion form the inertial sensor portions of the sensor yield a unified description of the device as a whole of its 6DoF of movement in the GCS. The combining of inertial and non-inertial measurements provides a previously unavailable double check on the values of each data stream (physical translation acceleration and optically derived change in position) since they are occurring in a monolithic senor device. Repeated measurement by both the physical (IMU) and optical (LDD) senor modalities provide a cross reference of expected and observed behavioral (motion) data that is utilized for a single description that has a unified ground truth reference. The ground truth data may be lacking in IMU data as these sensors are internal. The LDD has no mass value to reference to its measurements as inherent to all optic ray-tracing systems. By combining an onboard inertial measurement system and an optical ray-tracing measurement system, some embodiments may have the ability to converge on the true system state (6DoF) with a direct comparison and localization within its body-local global environment.

With a single point light source with line-of-sight for two consecutive readings, triangulation is possible given the IMU measurements of 6DoF change of state between the two LDD readings to that single light source. Utilizing a single light source to spatially locate an IMU may work with a set of discreetly separate IMUs positioned in a standardized layout on objects with known geometrical relationships such as the human body. A potential arrangement includes but is not limited to: one IMU on each foot, shin, thigh, pelvis, torso, head, and upper and lower arms. Using the built-in assumptions of the IMU software that, for example, keep the feet near to the floor in general when initialized (the zero Z elevation relative to the XY plane of the floor as described during the calibration T pose adopted by the IMU set wearer). The layout of an IMU set may be fairly standard for a human body-tracking schema. By taking advantage of a predetermined and expected layout, the model scale is introduced based on the LDD determined system device-device layout, arrangement, and separation. For example, a short person will have system devices that are much closer together than a tall person, but in either case their feet will be on the floor after they have donned the system device "suit" and have initiated the calibration routine once they are in the mocap volume. With the system calibrated to map the system device layout specific to the individual wearing the suit, any and all poses are measurable, and the rule that the feet are in contact with the floor is lifted. Thus, an actor can climb stairs of a ladder, do a cartwheel or other jump where the feet lift off of the ground, and the ground truth location of each floor and all other segments with devices is reported in the GCS, and not simply referenced internally to one another's previous initial position and relative position. For example, walking around the floor of a room delivers a repeatable and expected pattern of accelerations and rotations of the IMU, and by interspersing direction measurements within those trajectories, some embodiments may map any single light source relative to the floor as the foot location continues to change, especially during periods immediately following heel strike when each foot becomes quasi-static and in the stance phase of gait. As each foot assumes a very similar orientation on the floor during stance, it can be thus used to triangulate from each step landing location to the light source that we wish to include in the mocap volume instrumentation. Every light in the room or volume that casts a shadow can be included in volume construction, even spanning a room or rooms, or any configuration of space. This ability to collect the "suit" as equipped with LDDs on each linked rigid segment also allows inclusion of LDD sensors (that are not a part of the suit) to be captured in a common GCS, for example a motorcycle instrumented with an IMU and LDD, and its rider in a suit. Other examples include a horse and rider, an automobile and driver, and an aircraft cockpit and pilot, including the rider's saddle or driver's/pilot's seat itself.

Some embodiments may function by measuring LDD to any number of fix mounted IREDs, Internet of Things light bulbs or other light emitting appliances such as the Intel RealSense depth sensing camera IR projector. Additionally, an IR or other visible spectrum light source may be on-chip with or adjacent to the LDD sensor for use as a light source in a similar manner as the independent light sources. Control access to the IoT light bulb over Wi-Fi may be exploited for sequencing the powering of its diode(s) (on and power off changes of state). Since the power on and off times required to measure direction are very short, the illumination from the IoT light bulb will appear continuous to the naked eye. In the case of pairing with a camera that has an InfraRed projector as part of the camera system such as the Intel RealSense, synchronization with the IR pulse may be performed. Furthermore, when the IR light pattern is utilized for 3D mapping, a special case may exist where the exact pixel coordinates of the IR projected light are estimated by aligning the direction measurement performed by the LDD with the projection of the light, and the stereo pair of lenses and IR cameras of the RealSense. Furthermore, the LDD device can include a special region of the surface area exposed to light that is retro-reflective or nano-textured at specific light frequencies or intensities, or can change the IR light spectrum in specific ways such that the returning light is detected by the RealSense stereoscopic pair of IR cameras or single RGB camera, with a unique signature such that the camera set can individually identify each LDD sensor and its 3D position, and general attitude or orientation. Thus, by identification of the 3D location of where each LDD is located via the depth sensing action of the RealSense, the three directions of rotation of each LDD at its 3D location are refined using extracted LDD direction measurement between the IR projector and each LDD and combined into pose (6DoF) data. This two way mapping (3D location from the depth sensing camera pair and IR projection field) and rotation of that point in 3D space from the LDDs in the camera's FoV can only occur when the LDD sensor is moving into or out of or otherwise crossing one of the IR projection array "dots" which are acting as rays of light and converge at the emitter, and continue to diverge from their neighboring dots the farther away from the IR projector that the light is cast. The dots' actual sizes grow larger along with the inter-dot spacing as distance away from the emitter increases. In this case the LDD must be in the IR dot long enough and completely enough in the LDD sensor cross section to adequately be illuminated to have enough shadow cast on the "shady side" of the sensor array. Partial strikes by an IR "dot" will be filtered and scaled according to the amount of light that is exciting the "sunny side" of the LDD array. The portion of the sensor being lit by the IR dot does not affect measurement capacity since it is simply a photo-differential and not a total light power reading and even a small amount of illumination will result in a measurable shadow cast.

Some embodiments may include GNSS LDD IMU sensor fusion. Sensor fusion between GNSS IMU and LDD may be used, for example, outside under sunlight or moonlight. Azimuth and elevation to the sun or moon from your known GNSS coordinates and time of day (and day of year) may be a known value reported by a GNSS sensor. Some embodiments may leverage that information. If the light source is, for example, the sun, all light rays can be assumed to be parallel. The principal contribution of LDD readings to the sun correspond to the transit of the sun in the sky from Easterly to Westerly (+/−X) throughout the day, which when combined with magnetometer signals combining to yield a Northerly direction (+Y), will aid in determining the global orientation of the LDD/IMU and a more precise and reliable way to identify the gravity direction (−Z) by the triad of accelerometers.

A GNSS gives a geocentric location on the surface of the earth (Latitude. Longitude, rough elevation), but not the orientation of the GNSS unit. The GNSS signal essentially measures a 3D point in the space on or above the surface of the earth. The general rule for using GNSS is that the measurement error in vertical direction is three times that of the horizontal error. With the LDD giving a 3D unit vector direction to the sun or moon, and by taking the origin of the 3D unit vector and the signal from the GNSS as a single coordinate system with one unified sensor origin, adding a single light sighting allows the 3 rotations of the hybrid LDD+GNSS sensor to be fed into the on-chip or on-board IMU to correct all accumulated IMU drift thus aiding the IMU/GNSS sensor fusion already in most similar devices as found in a smartphone, some tablets and augmented reality eyewear. Many smart phones, watches and tablets come equipped with an ambient light sensor that automatically adjusts screen brightness and by substituting these sensors with a LDD, ambient light levels can continue to be extracted, while supplying light direction to lights in the vicinity. This power from the added direction information is magnified when the sun or moon is casting a shadow from near the horizon, as this can provide correction (aiding) that can be supplied to the native measurement accuracy of the GNSS sensor technology in the description of elevation. The dual role of direction in supplying both the IMU and the GNSS with additional information on their state completes the sensor fusion by bringing in a third frame of reference at the same time measurement is occurring and thus does not need to wait for subsequent measurement operations to make a differential or average (first central difference) determinations of location which are extrapolated into a single heading. By measuring heading or direction instantly, other methods of signal direction from the fused signal are now available at the same level of integration and or differentiation, and higher order analysis can be applied directly, such as principal component analysis for finding the direction and rotation of the greatest magnitude from the 3 planes of standard Cartesian coordinate systems. This results in substantially instantaneous and correct augmented reality video overlays to be displayed on a tablet, or eyewear, especially in where knowing precise elevation is important. The only other path to this data today is to locate the observer (GNSS sensor) on a hyper local 3D surface contour map of the earth, assume the observer is in contact with the earth (not flying or floating), within a range but unknowable instantaneous specific distance from the ground (handheld device for example). For indoor functionality GNSS and solar maps can be combined to estimate natural sunlight ingress through doors, windows and other transparent or translucent solid wall perforations to quantify ambient sensor-local intensities and directions.

The GNSS sensor functions to map its global position by measuring relative timing differences to map distances to satellites with known orbits. The GNSS cannot determine the orientation of a single sensor antenna, although it can string together a series of observations over time to estimate a heading. For high precision accurate GNSS use, a second GNSS sensor can be placed at or above a known location such as a land (property) survey pin, and 2-way communication between the mobile GNSS sensor and the fixed GNSS sensors may be used to triangulate relative distances, but still no directionality of either sensor is imparted. The major gain in accuracy is in determining elevation, and only by physically measuring the vertical distance from the ground at the survey pin to the GNSS measurement antenna perfectly above it and leveled such that differential elevation measurement is possible can elevation be measured with sufficient accuracy. An IMU has no external reference except gravity and easily distorted magnetic field measurements, and pairing GNSS with an IMU for sensor fusion only works when elements of the device as a whole move together for extended periods of time, as in for example elements attached to a vehicle or other such whole-system configurations. Typically, there is only one GNSS sensor per system, which limits usability under specific conditions, for example a phone only, vs. when the phone, head, and hand relative positions and orientations are needed. Today to geo-locate a camera with an IMU and GNSS, hundreds of pictures must be taken to align the three systems. This problem may be lessened with 5G, but will not function unless the phone is receiving a GNSS signal (mostly only outdoors) and has 5G or greater cellular service, and a user does not mind "waving" the camera around to calibrate the IMU, and waiting for processing to occur prior to alignment of virtually augmented information appearing correctly and coincident with features in the environment (examples: Mount Denali, Ak., inside the Louvre), without the need to have two-way wireless connection (GNSS is a passive one-way receiver sensor).

Based on on-device star maps, that include our sun and moon and their transits based on time of year and GNSS position (and elevation estimate) the 3D unit vector direction to those known sources of light that can cast a shadow on the LDD, the only conceivable orientation of the LDD sensor lies along that line. When triangulation between the direction line, the GNSS position, and the last known IMU translation estimate from dynamic (moving) readings taken at preceding GNSS derived locations, as well as the uncorrected IMU rotation signals, sensor fusion with the LDD supplied 3D sensor-based body-local direction is performed by trigonometric transformation.

The ability to take a single geo-located photograph without taking hundreds of extra photos to derive the lens 6DoF from camera motion provides a better user experience, more certainty that the information can be trusted, and a presentation of augmented information that is closer to real-time and that stays in perfect relative synchronicity. Today, time is needed to resolve large features like a mountain, or the rolling hills of a vista, and it takes many images to fill in the gap of information of which way the camera lens is pointing. Another problem that may be solved by some embodiments herein is that as the IMU/GNSS/Camera slows in its 3D translation velocity (nears rest), the signals tend to drift apart as error unavoidably accrues in translation and doubly in rotation, which is further contaminated by sensor distortion, which invariably leads to lower performance the less the device is kept moving. Embodiments may aid this existing sensor fusion during initial conditions acquisition by supplying a ground-truth to sensor alignment, and continue to correct readings during quasi-static periods, both when the device has ceased to be translated and doubly so when rotations have ceased. Such embodiments may be twice as helpful for aiding periods of rotational quiescence due to how gyroscopes are commonly constructed. A series of LDD measurements to one light can supply compensation to the gyroscopes, especially during periods when the sensor is at rest, or nearly stationary. A series of LDD measurements to two or more lights can supply compensation to the accelerometers, especially during periods when the sensor is at rest, or nearly stationary.

With some embodiments described herein, only one GNSS device is needed per individual. All other relative relationships can be handled by S6M/IMU sensor fusion. With 3D data, one may b forced to use at least 3 points or "watch" how one point moves over time. The disclosed system of vision naturally "measures" position and orientation or "slope" of things. In our visual perceptions of things, there is no separation between where something is and which way it is pointing it is a whole thing, in a specific relative place that moves and rotates together. In an effort to employ biomimicry, the science of making computerized systems process information the way that biology has evolved to do, the LDD process seeks to construe the orientation and position of objects in one single measurement. Biomimicry may exist in the LDD's ability to measure position and orientation simultaneously, as natural vision does. Biomimicry may exist in the LDD/IMU function akin to the natural biological fusion between the visual senses and the vestibular senses in vivo.

The fusion of this LDD sensor can form with a 3D camera (e.g., the Intel RealSense camera) by exploiting the camera's onboard infrared (IR) projector. As the stereo IR cameras map the depth to surfaces by stereopsis, the system may determine the distance between the LDD and the IR projector, while the LDD is measuring sensor angle to the projector, giving the complete solution of the relative orientation between the RealSense camera and the LDD at the sensor. This assumes the pattern of IR light has large enough "dots" and these projected light dots strike the LDD. As the LDD is in motion, the LDD will cross paths with a hardware prescribed number of "dots" that are part of the patterned IR light emitted by the RealSense IR projector. From the point of view of the stereo camera pair on the RealSense observing any and all reflected light and or conditioned light that has passed from the IR projector bounced of the LDD paired device's surface and back into both of the 2 (stereoscopic) cameras in the RealSense array, the 3D position of that reflective or textured patch region of or adjacent to and surrounding the LDD is measurable. From the LDD sensor measurement of the direction from which IR projected light is striking the sensor elements adjacent to the reflective or textured patch, in the same plane as the patch, the rotations of the LDD sensor are extracted to give the fully described pose of the sensor/reflector device in the same instant in time. Having a 3D point and a line that passes through it fully describes an object. Having this data collected instantaneously and in parallel (location and direction) as a combined measurement allows the computer system to eliminate the need for using a series of motion capture frames to understand and report movement dynamics. Instead, full descriptions of static time points are available and usable in creating real-time data for system post-processing of measured data. Furthermore, integrating the direction by comparing a series of direction measurements will lead to better prediction algorithms of rotation similar to what is being done with positions and translation to give velocity.

Some of the systems and methods described herein may be employed in lightweight aerial drones using the LDD microchip energy harvesting to generate power to fly the drone and perform mocap with serial light direction detection. The mocap equipment the drone carries into flight may be much lighter than a camera, as the LDD does not require a lens or camera housing. The disclosed capture measurement strategy is to measure and report 3D angle direction data to light sources, which is comparatively much less data dense than a camera system that captures entire image frames. To fly efficiently, a drone must be made as light as possible. If a function of the drone is to perform motion capture, the lighter weight the mocap system, the longer the drone can stay airborne, as battery power can be used for longer flight times instead of capturing and processing image data and transporting relatively heavy cameras. See, for example, https://arxiv.org/abs/1804.06112 (retrieved 9/11/20), incorporated by reference herein.

Figure 15:
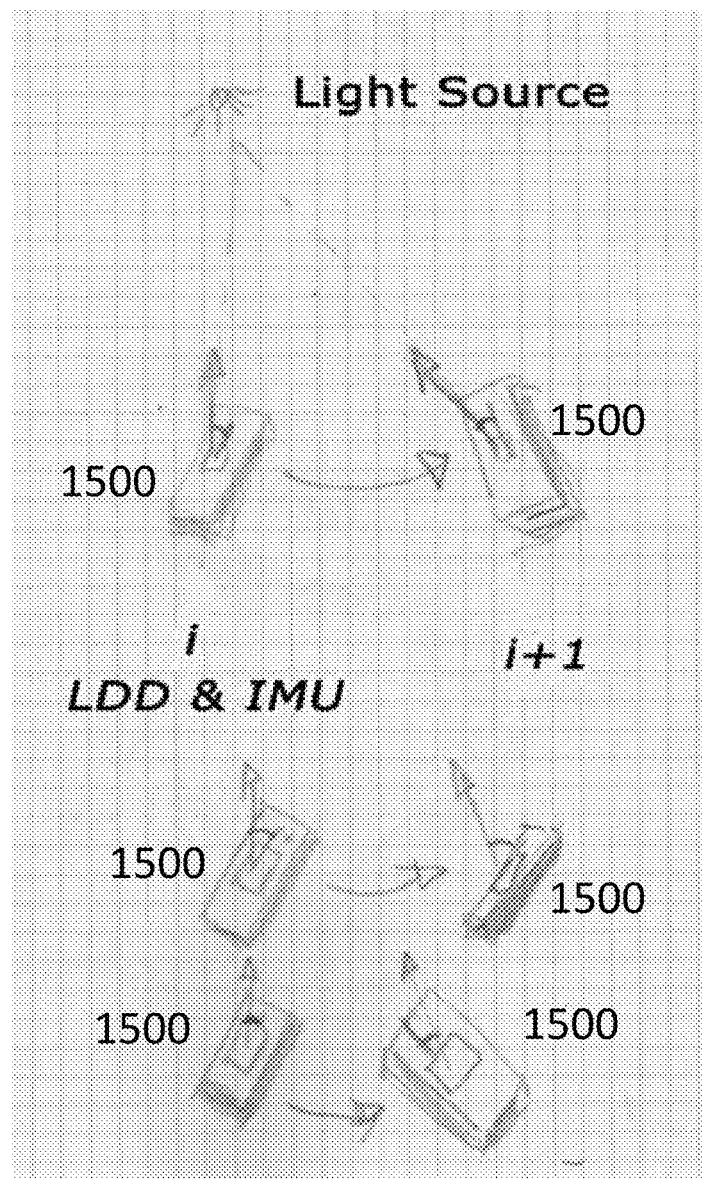
FIG. 15 is a view of a monolithic build of a 2 plane LDD measurement device, a 3D accelerometer, and a 3D gyroscope, according to some embodiments of the present disclosure.

FIG. 15 shows a monolithic build of a 2 plane LDD measurement device, a 3D accelerometer, and a 3D gyroscope (and possibly a 3D magnetometer) 1500. This is a MEMS or NEMS device and they can operate synchronously or asynchronously. In FIG. 15 a synchronous measurement scheme is illustrated, where a measurement occurs by the LDD and the IMU (accelerometer, gyroscope and magnetometer) simultaneously at i and i+1. The IMU measures the translation and rotation of the device 1500 in a sequence of two time points (start and end of curved solid line between i and i+1), and the LDD portion of the device 1500 measures direction at i and i+1. These different sensor measurements are fused to determine the physical coordinates of the device 1500 at the two states by triangulation. Asynchronous modes include higher and lower sampling rates by the LDD that are parallelized When a single light is casting shadow on the LDD there is no determinate solution describing the 6DoF of the LDD. By leveraging the strengths of earthbound IMUs, namely 3D acceleration under the influence of gravity, and the rotation of the sensor about its 3 axis directions relative to magnetic North, one additional piece of direction information allows the construction of determinate solution for overall whole device 1500 position and orientation in the instant of measurement. Special considerations may apply to the rotation again as factors including the Abbe angle or sine error and using linear accelerometers to detect torque induced by resistance to change in angular axis are the common ways to measure changes in axial rotation, which doubles the measurement path to the actual measurement variable value.

There are at least three examples in this figure of how an LDD/IMU device 1500 can move between time points. To completely initialize position and orientation (pose) of the device 1500 the LDD/IMU may need at least 3 readings to separate light sources, but some embodiments may only need two light sources for quality measurements based on user need or preference. Or the device 1500 may be paired with an external device such as an HTC Vive, which includes a laser direction source called the Lighthouse 2. With light direction from the base station known, a single reading by the illustrated LDD gives the second direction needed to describe a line. The dual axis laser emitter here gives direction to the light emitted, which is powerful. One way or another device 1500 may play connect the dots with this system. One way is to know what direction and where light was thrown from like the Lighthouse product does. The next part is to catch that light. Some embodiments may have the advantage of measuring what direction that light was approaching from. The Lighthouse and Lighthouse 2 knows at what lateral angle and at what vertical angle its laser beam is directed. Two angles describe a unit vector, with the origin at the laser source. Wherever in 3D space that laser beam strikes an object, if that point is a photodetector, the system can recognize that that sensor lies somewhere along that line. With a second Lighthouse base station also painting the 3D volume with rows and columns of laser light, a second laser strike occurs on that same photodiode, albeit the second laser strike must occur at a temporally proximal time point to add valuable information (often circumvented by having a multitude of photodiodes arrayed across the object in a convex hull for example (such as the outside surface of a Virtual Reality headset or a circular ring on a handheld controller). The Lighthouse can utilize a phase shift such that only one laser is painting the space at a time for disambiguation of which of the two intersecting lines are being constructed: the horizontal and vertical angular departure from each Lighthouse base station device normal. The intersection of the two lines allows triangulation of the photodiode 3D coordinates. Furthermore, a set of photodiodes, each with a triangulated two-line intersection mapping of 3D coordinates, may allow the construction of a rigid body of known points that can then be imparted with a single 6DoF description. To avoid all these extra steps (two measurements per photodiode, minimum of three photodiodes), a single LDD measurement may deliver the equation of the end point for each laser beam. A lighthouse base station knows the equation of light departing the base station's emitter, the LDD knows the equation of light striking its array. Knowing both ends of a line is not a complete description of the state of the LDD, as the length of the line is unknown. The length of the line that connects a Lighthouse base station to an LDD sensor is limited, from zero (plus the space between the Lighthouse 2 base station emitter and the outside of the device housing device itself, and from the LDD sensing array to the outside of the housing that contains the LDD sensor itself) to a generally fixed distance away from the base station given the intensity of the laser, and the sensitivity of the LDD, and to a lesser degree the angle between the line and the LDD sensor. The LDD sensor is less sensitive to excitation the farther from normal light is striking it up to the limit of measurement at approximately 55 degrees away from overhead (normal). This ends up creating a bell-shaped curve of sensitivity that is revolving around device normal (both in LDD sensor local North-South and East-West directions). With a second Lighthouse base station also emitting laser light in known directions, the second LDD measurement completes the full description of LDD pose. Two measurements of a single sensor may now suffice to give the same information as two measurements to each of three locations. By eliminating the need for multiple adjacent 3D measurements and delivery of 6DoF instantly and directly, integration of change in state (especially rotation) is enhanced for accuracy of real-time control of a game or other instrumented device such as a telemedicine surgical tool.

In a concept related to FIGS. 13A and 13B described above, some processing may be focused not only on the shape of the entire shadow, but that some LDDs may be in the shadow and those in shadow create a negative space inside the volumetric model of the object or human being tracked as a set or linked rigid bodies.

For example, a null signal from individual LDD devices while they are mounted on a mocap subject and measuring means that particular LDD sensor is not being struck by light from the light source in the room that is currently powered up. The absence of a measurable shadow cast on the LDD sensor by light emitted from that particular light fixture (LDD sensor completely in shadow) gives information (a solution set of 3D space) in the volume (inside the space formed by the set of system lights) such that the zero signal LDD's position and orientation is collinear with the powered light and some portion of the mocap subject's body or form, which prevents light from striking the LDD sensor. The LDD sensor can also be facing away from the light. The null signal from an LDD sensor can indicate that it is farther from the powered-up light fixture than the mocap subject and/or the LDD sensor is facing away from the powered light (pointed in a direction that orients the FoV of the LDD sensor away from the powered light). Measurements by LDD sensors "in the shade" by any LDD in the volume may allow the construction of a negative image inside the volume between the LDD and the light that is on. This null shadow effect allows a simplified "skeletal solver" to be utilized where segments of the mocap subject are fit into a configuration that blocks the specific LDD sensor(s) not being illuminated by the currently powered light fixture. Since a line (from previous measurements) can be drawn from the light to each LDD, the ones that read zero can only be either pointing away from the light or blocked by the object(s) in motion. Shadow mapping of shade cast by mocap subject by IRED in the Lighting System Units.

The fitting of a linked set of 3D segments that are combined to represent real objects such as the human body may be constrained by a rule that the segments are each a rigid body that does not change shape during motion. The model can be further constrained by limiting the degrees of freedom at each linkage joint between pairs of connected segments. For example, the knee joint can be idealized as a hinge joint with only one axis of rotation (flexion and extension of the lower limb relative to the thigh). The relative segment to segment position and orientation of this set of linked rigid segments may be fitted into a negative space created by the silhouette of the person's body by background subtraction from the scene before they entered the synchronized cameras' FoV(s). This process of model fitting into 3D space is now tasked to machine learning and Artificial Intelligence. As these segments are rigid and generally cylindrical or even doubly curved, as for example the thigh is larger in diameter at the hip than at the knee and the taper of diameter size is non-linear, rotation of the segment as a whole becomes even more difficult to establish from a multi-view set of silhouettes alone. One piece of total direction information referenced to a specific region on a doubly curved cylinder-like segment where the LDD is mounted resolves all remaining orientation details in the data. To a camera, the relative axial rotation of a cylinder cannot be measured, whereas the other two rotations of a cylinder are fairly easy to detect and measure. This lack of precision axial rotation leads to a troubling lack of accuracy in reporting joint rotations in the other planes besides the principal axis of the joint as limited by anatomical constraints. Even a rather tightly constrained joint such as the human knee can have over 140 degrees of flexion extension range-of-motion, but axially between 30- and 90-degrees flexion the knee has 45 degrees external and 25 degrees internal rotation. Rotary motion decreases with further extension and, at 5 degrees of flexion, the knee has 23 degrees external and 10 degrees internal rotation. Additionally, there is a small range of motion in valgus-varus as between thigh and shank at the knee as well. As the human body is not actually composed of rigid geometrical segments, and these segments interact in less than pure angular departures from their adjacent neighbors, fitting such a model on video data remains difficult. The LDD sensor brings a measured value to the estimated fit between model and reality and lessens the need for a highly constrained linked-rigid-body model. When an LDD does not get excited by a light that is currently powered up, the aspect of the human body segment that it is attached to is most likely turned away from that light source location. A negative ray tracing is employed in software to map the spaces inside the 3D capture volume that cannot be lit in each individual light fixtures' casting space because of prior confirmation that the human body of interest (with LDD units attached) stands between the light source and the individual LDDs. Not only is potential for the human body of interest to be between the light and LDD, the LDD location around the circumference of the segment it is mounted to is considered such that for example part of the arm is lit by a light, but the LDD is on the other side of the arm and is not being lit by that same light. The absence of LDD signal when prior knowledge places it mounting location as potentially in the FoV of a specific light, adds to that light's particular modified casting space an additional sub-volume of negative space that for example falls between a human arm the blocks a LDD that is mounted to the hip (left arm, FIG. 1 below).

Furthermore, a LDD sensor that is affixed onto a generally cylindrical segment will rotate with the segment, and while the segment may be illuminated and have line of sight to a particular light source, the rotation of the segment may be such that the aspect of the segment with the LDD tracker does not have line-of-sight with that light source, which leads to a data exclusion range of segment orientations that the LDD and segment may be in relative to that light source. By extracting details of which direction the LDD is not facing, the segments onto which they are attached are likewise forced to reside within those ranges of position and orientation relative to the currently powered light source.

Figure 16:
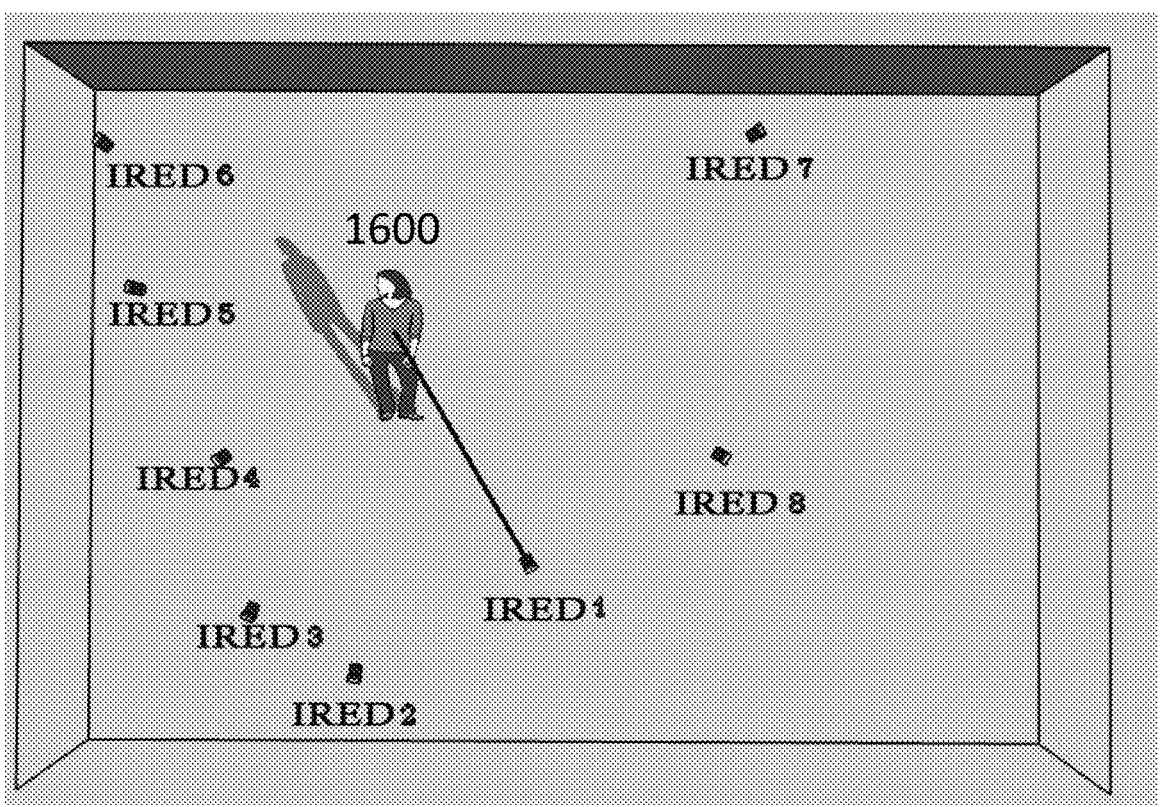
FIG. 16 is a view of a human mocap subject with LDD sensors placed on the body and lights in the environment, according to some embodiments of the present disclosure.

FIG. 16 shows a human mocap subject 1600 with LDD sensors placed on the body, including a number affixed to the posterior aspect of the body. The LDD sensors on the woman's back will have a null shadow signal when IRED 1 (e.g., which may be part of a T shaped LSU as described above with respect to FIG. 4) is lit, and this means the subject's body is positioned between those LDD sensors on her back and the powered light, and potentially the FoV on those LDD sensors on her back are also likely facing away from IRED 1.

Figure 17:
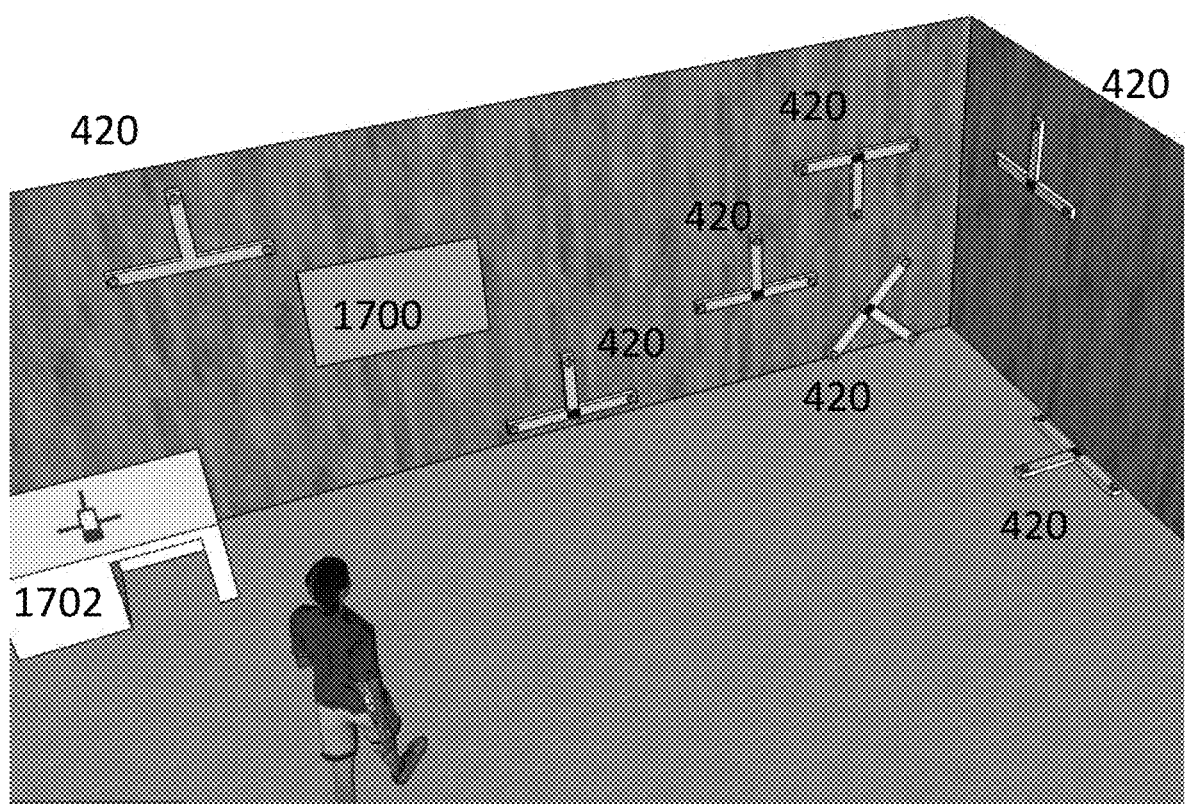
FIG. 17 is a view of an example illuminated environment, according to some embodiments of the present disclosure.

In some embodiments, the LSUs 420 (e.g., as described above with respect to FIG. 4) may be shaped into a T shape. FIG. 17 shows an example illuminated environment with six T shaped light arrays 420 with an LDD at the center, with the array in the upper left corner containing just 3 LEDs. Groups of pixels in the television screen 1700 flash T shaped bursts of white light intermittently and in serial (for example: 1 upper left corner, 2 upper right corner, 3 bottom center) and act as the first T to calibrate LDD.

There may be IRED fixtures at each of the three ends of the T shape and an LDD sensor at the center of the T where the two linear sections intersect. In one embodiment the T shape is made of two extruded aluminum bars, for example 750 mm long, 20 mm wide, and 5 mm thick. At each end of each bar is a mounting fixture that accepts the LDD and its housing, or a LSU. Along each bar is a channel for system wiring and a connection fixture such as a USB male or female port that enables connection of the parts of each T as well as connecting all system T units and independently mounted system lights together. The bars may be bolted together or snap together to form the shape of a T, with 90-degree orthogonal corners, at a point equidistant from top bar ends and together reside in one flat plane. Lights are connected to the distal 3 ends of the T and a LDD is attached near the junction of the bars in the remaining free mounting fixture. The pair of bars can also be configured into an L shape.

Figure 18:
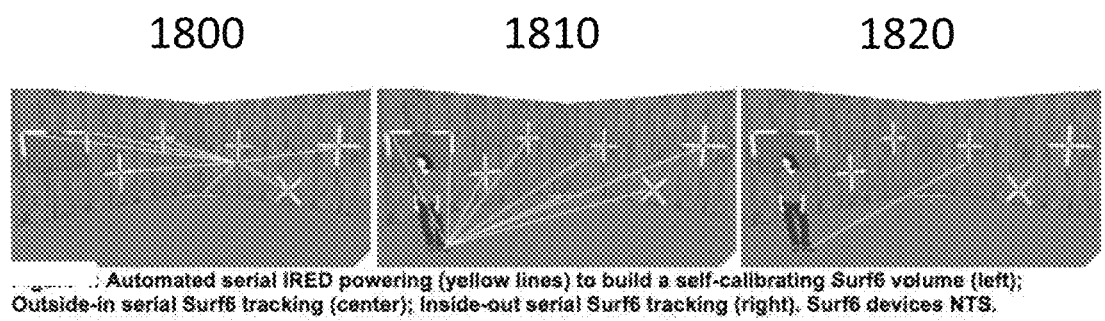
FIG. 18 is a view of an example system within the environment of FIG. 17 in use, according to some embodiments of the present disclosure.

FIG. 18 shows a method of calibrating and/or using the elements in the environment of FIG. 17. In 1810, light elements may illuminate (and be detected by respective other members of the environment) sequentially to self-calibrate. In 1820, outside-in tracking is performed. In 1830, inside-out tracking is performed.

When LDD sensors are in the vicinity of a display screen or projector that operates as a television, computer display 1700, etc., there may be no need for T shaped LDD/LSU around that TV screen if every pixel of that screen is controlled to turn off all pixels for a fraction of a second while leaving small tight pixel groups in a on and off rapidly in different areas of the screen (so fast no one watching would perceive it happening) in at least 3 areas (or the 4 corners or several along each edge) in serial so there is a repeating T pattern (or a rectangular pattern if 4 corners are actualized). The control of pixel groups on such displays in the vicinity of the LDD units can be performed over the internet, for example. Each of the four patterns of localized (near each corner) activated cluster of pixels is inserted into the running stream of video on screen as one frame of information. For laptop and desktop computers, most tablets, and smartphones this is standard practice already. Standard cinematic video for a feature film for example is played at 24 frames per second with a ⅟₄₈ second shutter time. This is known as "black screen insertion". Even if each image is displayed for nearly the entire time as is possible with LCD screens, no loss of picture quality will be experienced by the user if intermittent patterns of pixel activations are intermixed with the video, as the majority of the screen (>90%) will remain dark as usual. For larger screens not connected to a computer, a special Wi-Fi enabled cable box will supply the control of the connected display and flash the 4 frames of signal light between video frames, or during black frame insertion periods with the same schema.

There may be a T shape cradle 1702 for a smartphone for when larger distances from smartphone screen to LDD are encountered (shorter distances can use pixel groups on the screen as T shaped LSU. In an example embodiment, the T shaped cradle has three lights affixed to arms of plastic that can be 20 centimeters long, 1 cm wide and 5 mm thick, and that have a channel and wiring to light the LED or IRED. The three arms extend orthogonally from a center rectangular tray that has a third support leg that folds away but is positioned for when in use to project from the rear of the unit to form a stable platform formed between the bottom short edge of the tray rectangle and the end of the support leg. The support leg and the bottom of the tray may have non-slip rubber or other surface texture applied to improve stability. The angle of the support leg to the tray may be adjustable to change the viewing angle between the tray and the user. The tray has a ledge that the user's smartphone or tablet can be rested against with the back side of the display in contact with the available portion of the rectangular tray. The tray device can be powered and have Wi-Fi, and possibly a charging port for certain devices or a wireless charging coil embedded in the main body of the plastic rectangular tray. In some cases, Bluetooth or other near field communication may be utilized for passing control signals of the 3 lights on the cradle from the user's device on it to turn the lights on and off. As the function of cradle lights is to excite LDD units in the vicinity, and are controlled by the device placed upon it, the device can use installed software to turn lights on and off, receive incoming Wi-Fi or Bluetooth packets of data from the LDD containing timestamp and double angle data. The device then computes the 6DoF solution of each LDD and passes the pertinent 6DoF data of each LDD into the system control of the device. The 6 doF data may be scaled for instance such that the visual perspective held by the user relative to the device screen is considered to ensure data manipulated on screen relates to scaled movements of the LDD equipped on the body. For example, the tip of each finger of the hand. On power up of the cradle the initial conditions of the cradle, its lights and the user's device in position and orientation relative to any and all LDD units in the vicinity is adjusted from the expected state to the actual state as for example the user may not have placed their device in the exact center of the cradle tray. In the initialization period, the corners of the user's device screen also light to co-locate the screen on the cradle. Following initialization, the screen of the user's device may reduce the frequency of flashing its corner illumination pattern signature, as it is believed that the device has not moved relative to the cradle. The screen of the device will resume its patterned corner flashing if the onboard IMU detects a physical change in location or rotation.

A method to hybridize the LDD system with a camera is possible by taking LDD measurements between camera frames while the camera shutter is closed. In cinema film the feature is typically shot at 24 frames per second with a ⅟₄₈ second shutter time. This frame rate and shutter time creates static images with the appropriate amount of "motion blur" for optimal viewing by a human audience. This classic 180-degree shutter rule leaves the shutter closed half of the time action is being filmed. Motion capture systems use synchronized shutters to ensure pictures of the objects in motion inside their combined FoVs are captured at the same instant in time. The amount of time the camera shutter is left open is adjustable, but too long and objects get contaminated by motion blur, and too short, the image is underexposed and objects fail to be displayed properly. There exists a minimum shutter time as well, which is the period in which data is typically shuttled from the cameras to the controlling capture computer. Marker data is simplified to just the x and y image sensor local centroid location of the marker's full appearance, while full color video must be pixel by pixel transmitted to the base capture computer. No matter how motion is captured (marker of full color video) the shutter-closed time constitutes unused measurement time. For lower capture rates (<60 Hz) the exposure time is typically close to the 180 shutter time leaving 50% of measurement time unused, and at 3 Hz, nearly 90%. Only at very high capture rates does the shutter time begin to approach the software forced minimum needed for data transfer and frame reset and new frame data header writing. Even at the minimum shutter-closed time, several LDD readings can be made before the camera shutters open again for measurement of the next frame of data. By using the LDD during the inter-frame time periods additional data on the state of the object in motion are made available, namely the direction in which it is facing. Many of the common mocap camera systems use an IRED ring that surrounds each camera lens. The lens of each camera has been calibrated in 6DoF within the Global Coordinate System of the volume. By controlling the IRED ring on each camera to quickly flash in series or in pairs, multiple directions to the LDD within the volume are accessible without additional hardware or calibrations. Furthermore, if the LDD unit includes a LED fixture that is activated when camera shutters are open, and deactivated between frames while the LDD is making measurements the camera system can treat the IRED on the LDD unit as an "active marker" and triangulate its 3D position as it would any other active or passive marker inside the camera capture volume. By taking this first step with the cameras of measuring the LDD devices' 3D position, a single direction measurement will suffice to resolve the other 3 degrees of freedom, namely the 3 rotations the object is undergoing. Since the camera ring of IREDs has a known 3D location, the IRED on the LDD device has a known 3D location thanks to the cameras' native processing of ray tracing information, thus forming a 3D line segment, a single angle measurement orients the LDD device entirely at the line endpoint at the LDD device IRED.

Some physical configurations of LDD systems are described above, but others may be possible as well. For example, in some embodiments three or more LDD microchips may be built into ½ of a cube, so measurement ranges overlap and expand total sensitivity to light to a range of over 200 degrees: 55 degrees from LDD 1, 90 degrees between LDD 1 & 2, 55 degrees from LDD2=55+55+90=200.

Some embodiments may have additions beyond the 4 single plane LDD chips built into a pyramid as in FIGS. 7A and 7B. For example, some embodiments may have the IRED on-board as well. In some embodiments, on one microchip, the system may measure four or up to 8 planes of light direction.

These embodiments may include flexible circuitry to make the electronic connection wiring bend at up to 90-degree angles relative to one another to get signals from 3 or 4 individual microchips fixed mounted to a substrate with set relative orientations to one another hard wired together into a unified structure. The black and white pyramid may have flexible electronics to get one differential signal off each chip, but other embodiments of an LDD microchip may have 8 planes of LDD sensitivity on one integrated circuit. Other embodiments may get the 8 LDD readings down to one pair of differential signals off the chip. The 8-plane microchip may have LDD and at least one IRED, similar to FIG. 7A described above.

Figure 19:
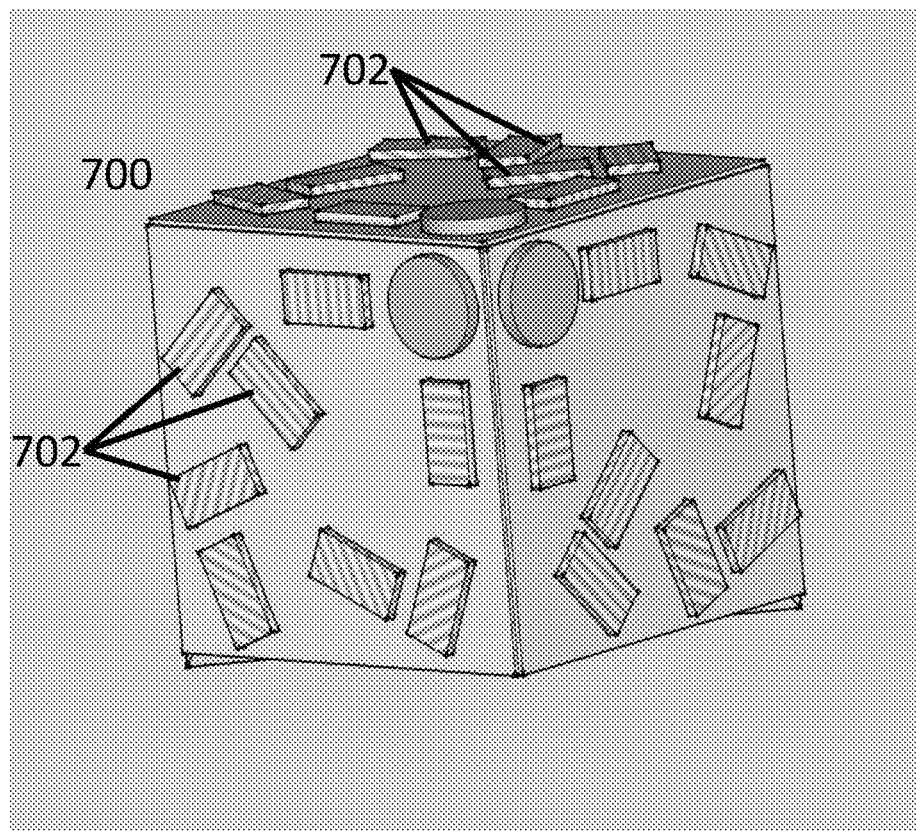
FIG. 19 is a view of an example motion tracker, according to some embodiments of the present disclosure.

FIG. 19 is a view of an example motion tracker 700, according to some embodiments of the present disclosure. The cube 700 in FIG. 19 has 3 of the 8 plane LDD 702 with IRED microchips arranged so the IREDs are all adjacent to each other and will be wired to turn on at the same time. This figure shows how the walls of the LDD arrays are laid out in 8 directions. The cube sides could be 90 90 90, but they could be lower too. GNSS and IMU fit inside.

As described above, multi-plane LDD microchips with a known physical mounting separation create a sensor-to-sensor LDD triangulation to a single light turning on. This gives distance to a light source in a similar manner to stereopsis with cameras without image processing. The pair of LDD structures with a known baseline distance between them (see FIG. 7D, where the distance between trackers 700 is known) may be made just like the embodiment shown in FIG. 7D, but with IREDs and with the 8 plane microchips (not shown) as described herein. Some embodiments may include an IMU 790 on the bar as well. For example, devices may have a single IMU between the two LDD arrays 720 that are mounted to a rigid substrate 703, which gives a fixed baseline to the inter-LDD spacing and relative orientation, and relative location and orientation of the IMU. The substrate can be of any shape and the LDD and IMU can be positioned in any configuration as long as relative position and orientation is mapped during fabrication. For example, one LDD array at each hinge on a piece of eyewear, with the IMU at the bridge. Devices are built to enable the largest FoV for each LDD possible, while some practical effort may be given to creating symmetric physical layout schemas, both with the LDD arrays and the IMU, for example each LDD has the same relative offsets to the center of the eyewear lenses, and the IMU splits that difference symmetrically, in order to reduce sensor signal bias and to distribute error correction evenly. The stereo pair of LDD sensors allows stereopsis without imaging. Measurement of lighting conditions can account for parallax between the pair of multi-plane LDD sensors on a user's eyewear, and a set of multi-plane LDD sensors embedded in the sandwich construction of automotive safety glass. Windshield and side window or other glass fabricated with semi-transparent, or with very small LDD circuit sizes that render sensors small enough to be practically invisible will be positioned in the glass, and outside a driver's primary lines of sight to take multiple geometrically paired light direction readings at two roughly parallel planes: the plane of the vehicle occupant(s) eyewear, and the plane of the vehicle windshield. The two planes will have signature relationships if the driver is not paying attention to the road, for example. This set of plane positions and orientations information will help the planning of future vehicle navigation steps.

Screens (e.g., iPhone iPad TVs laptop screens) may be configured to flash specific tight groups of pixels very fast in serial, as mentioned above. This can occur during black frame insertion events common to the operation of high-frequency (>120 Hz) display screens. When each group of pixels is on all other pixels are turned off to make every screen into an LSU. The tight groups may be bright enough to cast a good shadow on the LDD.

Some embodiments may integrate many different types of light source devices, e.g., Internet of Things (IoT) lightbulbs and/or other IoT devices. IoT light bulbs can also be wired devices that serve as part of a Visible Light Communication (VLC) system as the emitter (also referred to as "LiFi") and for which the LDD sensor can act as a receiver. IoT devices can be programmed to all turn off and on independently for fractions of a second, emitting specific steradians with a terminal end in the shape of a bell shaped-curved cone at 50% power of visible light intensity that can be estimated as emanating from a single point in 3D space. The shape of the light steradian that is emitted from the IoT lightbulb is built into the fixture by its manufacturing process. By knowing the type and make of bulb, the proper light steradian or frustrum (from panel lights) can be ascribed to the volume. In addition to the maximal arc of viewing angle, the shape of the light cone terminates at its 50% illumination threshold distance that the LED can effectively cast light to with sufficient power to excite a LDD. The diffusivity of each particular light fixture is also part of the description of the light cone. The IoT light is controlled to turn off and on in rapid succession upon receiving a wireless communication packet from software on a nearby control device to do so. This control software can be on a handheld device, or personal computer as long as that system is connected to the same Wi-Fi network as the IoT light. The control software also receives data packets over the same Wi-Fi or Bluetooth network of timestamped LDD measurements, and correlates that data with the IoT position and timing of shadow casting light pulses that strike the LDD being queried. Before the system can operate for mocap the IoT light bulb 3D coordinates are mapped by available nearby LDD sensors and or LDD sensors that are paired with a IMU and or a GNSS such as for example what may be in a LDD enabled smartphone. The pulses of light can also be used in communication of the bulb's 3D position and the direction of the normal vector that describes the brightest light emission paths from the fixture (such as a bell shaped cone with light intensity dropping off as angle away from normal increases). For two-way VLC communication each device must have a receiver must have a transmitter LED. For VLC downlink each LED luminaire will have a LDD sensor mounted physically next to or adjacent to the LED circuitry with adequate LoS, with or without an infrared filter. For the uplink mobile devices with the LDD circuitry use the on-chip or adjacently mounted IRED circuitry as the receiver-transmitter pair. VLC uplink communication may cooperate with Wi-Fi or other Radio Frequency communications. With knowledge of the 3D direction from luminaire to a mobile device and the 3D direction from mobile device to the luminaire effectively solves the transformation between the two coordinate systems: The Global Coordinate System of the luminaire(s) and the Local Coordinate System of the mobile device with only the length of the line connecting them remaining unknown. The angle data from both ends of the line allow more accurate estimations of the distance between the light emitters and the light receivers. Knowing the power and shape of light emitted from a LED, and along which direction vector the mobile device is calculated to be located inside that luminaire light steradian, a close estimation of illumination power is possible at all distances in that particular direction. Then with the knowledge of how photoexcitation of the photodiodes in every LDD array varies linearly with the angle of light arriving and striking the photodiode and knowing the angle of the mobile LDD array based device to that light, the expected level of photodiode current generated from light is disentangled from the light intensity effects due to sensor location in the illumination cone of the emitter, excitation levels at the receiver due to the orientation of the mobile LDD sensor along that direction vector, and the actual physical distance between the emitter and receiver both in the uplink direction and the downlink direction. The lights that operate for VLC can be used, when operated with the multi-plane LDD circuits, as part of a commonly described Visible Light Positioning (VLP) system, that also supplies the additional information on the orientation of the sensor at every positioning measurement. We thus refer to LED-LDD systems as a Visible Light Communication, Positioning and Orienting (VLCPO) system.

Some embodiments of the systems and methods described herein may include a haptic fingernail embodiment. Mounting a LDD onto the tip of one or more fingers may serve to convey the end-point movement (position and orientation) of each digit while a 6th LDD per hand on the back of the hand conveys the pose of the body of the hand consisting of the 8 carpal and 5 metacarpal bones. In such embodiments, eye-safe IR light and LDD sensors may be used instead of higher energy radar EM radiation. Any number of LDD that fit on the back of the hand can be implemented. Each fingertip LDD may be positioned on the top of the fingernail of each digit. The whole hand LDD device may rest as close as possible to the intersection of the longitudinal and oblique arches of the hand, as the LDD measures angles linking the direction of the tangency to the anatomical features of the hand will assist in locating and contextualizing motion and rotation data in the same coordinate systems as the structure of the hand. These 6 devices may be wired together with the five finger sensors each supplying a wire lead to the main hand unit. The main hand unit (or sub-units) is of sufficient size to capture a threshold power surplus of light energy that is then stored and distributed system wide for measurement, processing, and transmission of LDD data to the extent possible based on the intensity of light being cast in the vicinity and the amount that ends up striking the LDD sensors given its relative pose. As photodiode excitation drops the father from normal that light is striking its surface, the amount of power generated by the LDD especially in high off-normal angels that approach the 55 degrees from normal limit of the LDD sensitivity range the power generated on such events will aid or supplement on device power systems such that systems of memory, computation, and data transmission are uninterrupted.

LDD is a photodiode. It generates nominal electricity when struck by light (and it measures light direction). A 5 finger glove (Left+Right) with a super small LDD over the fingernail of each digit may be wired to a larger LDD photodiode (or group of LDD photodiodes) on the back of the hand that powers each whole glove of the pair with enough extra energy to transmit all 6 LDD signals (five fingers and back of hand) to the master data set. Either by Wi-Fi (2-way radio) Bluetooth or LiFi from an onboard back of the hand IRED, as described above.

The addition of direction measurements that are relative to the segment the LDD is attached to enable whole segment orientation and positioning to be added to training data used in AI systems that accurately map the connected segments of a system such as the human body. The ability to properly train AI hinges on the accuracy and precision of the feed sources of information. The challenge to image based segmental mapping is the lack of certainty as to the axial rotation of the cylinder sections that make up the model.

6DoF data on the surface of a mocap subject gives machine learning information on how to position more or less cylindrical body segments inside the volume. The head is basically a cylinder, so is the upper arm and lower arm, the thigh and shank, even each foot and the torso are modeled as roughly rigid cylinders. As S6M feeds data pertaining to which is pre-initialized with what "side" of each cylinder an LDD is mounted (or several LDDs per cylinder), the entire segment is easier to resolve, leading to more precise and accurate tracking of the body (or other object with known 3D shape). your leg for instance is long, but more or less round in cross section. With an LDD mounted on the side of the leg, the entire relative location of the rest of the cross section and length of the leg "cylinder" is fixed. This is especially true for the head in particular. It is a cylinder from the neck up. Two LDD with known separation will allow this shape to be tracked perfectly with only one or two lights in the vicinity.

Figure 20A:
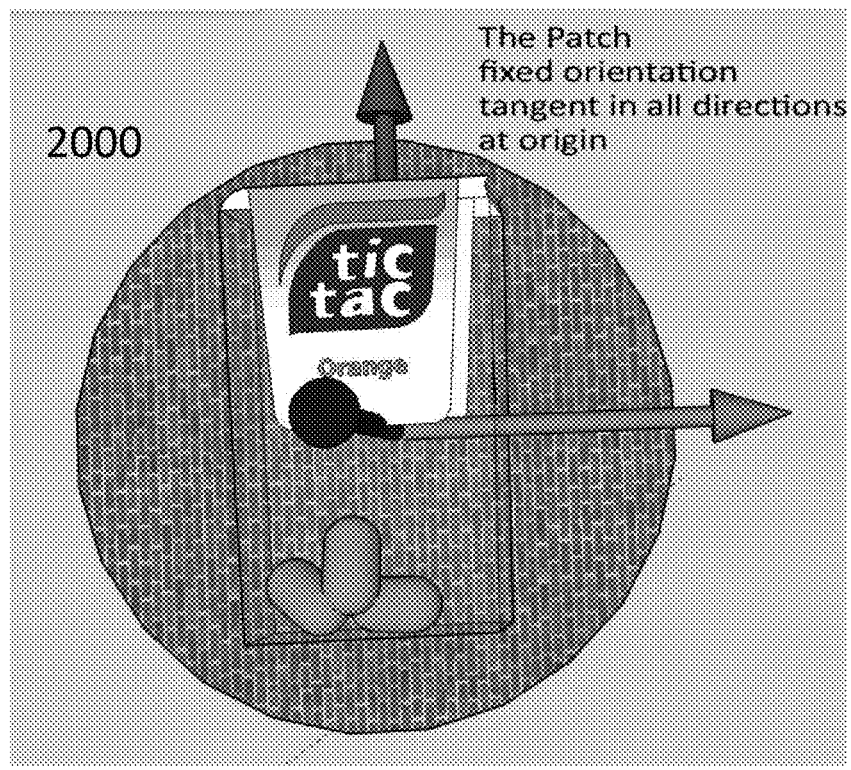
FIGS. 20A-20C are views of bendable surface plane patches, according to some embodiments of the present disclosure.
Figure 20B:
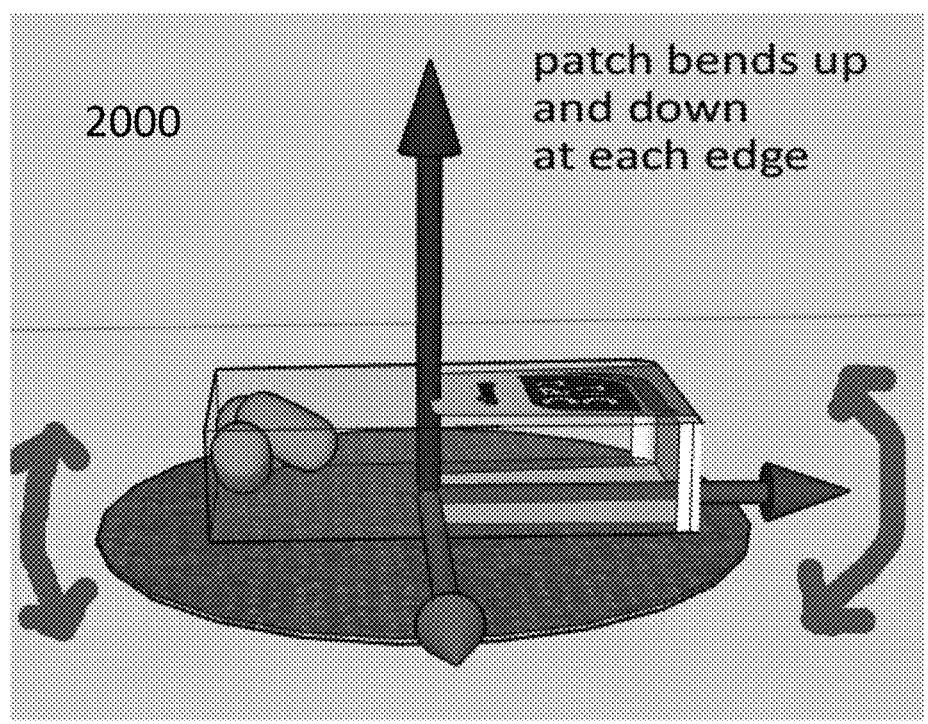
Figure 20C:
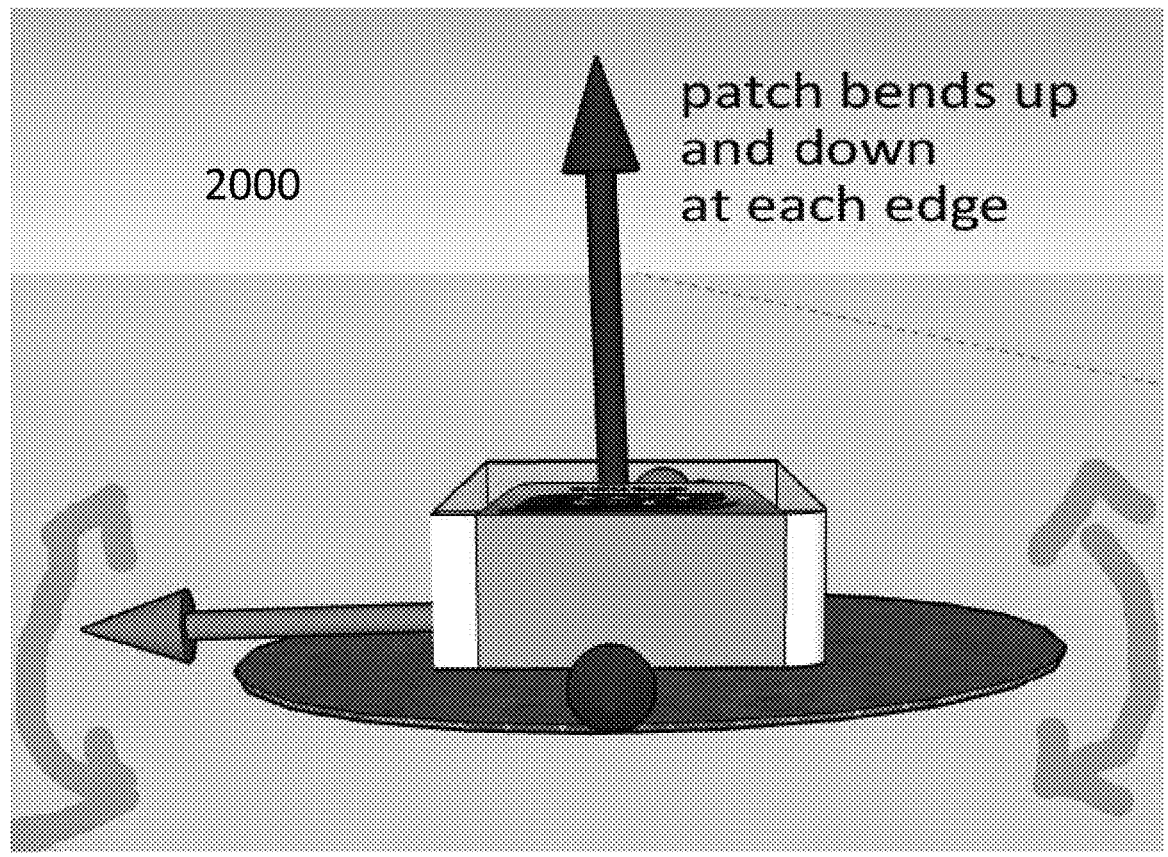

FIGS. 20A-20C are views of bendable surface plane patches 2000, according to some embodiments of the present disclosure. Some embodiments may include a software tool to bend the surface data attached to each LDD for example when the linked segment a group of LDD sensors is attached to is not truly rigid. As the function of the LDD sensor is to map position and orientation of point locations in 3D space, the mounting point of the LDD sensor serves as a miniature platform that is tangent to the underlying object's surface where it is attached to it. The plane of the LDD sensor is built into the device on a parallel plane to the mounting surface of the device, with a minimal vertical offset away and above the actual surface of the measured object or segment of an object. This parallel measurement plane may exist as close as 2 millimeters from the surface plane of the object being measured at the measurement device application point. The LDD sensor data result serves to dictate the contour information on the surface area immediately adjacent and beneath the LDD sensor. The surface data translates and rotates as a single object based on the measured and computed 6DoF of the LDD sensor over time, and is offset to the actual surface of the object of interest from the measurement point by 3D translation and/or 3D rotation as per user input. By default, the LDD device measurement origin has been translated in one direction (−Z) down from the origin of the LDD sensing arrays to the bottom of the LDD unit housing. No other translations or rotations are made in the default setting as the transverse LDD measurement plane is coincident and parallel with the bottom mounting area of the LDD unit as a whole (plastic case or housing). The only translation needed is the vertical offset from sensor to housing. The other two principal directions of the sensing array remain unchanged between the LDD sensor and the plastic housing it is encased in. By coupling the parallel measurement plane of the LDD sensor to the control of how local object surface data is deformed the software connects all adjacent LDD measurement data poses and ultimately fits a curved surface of a non-rigid segment to connect them. The resulting data generated surface is first constructed as a mesh of points in a similar manner as a 3D mocap system, by linear segments between adjacent LDD sensor origins. Then the tangent surface plane underlying each LDD is added to each point location data as a circle of increasing radius tangency. The tangent surface plane can extend undistorted at least as far as the limits of the LDD unit housing. The surface plane tangency begins to warp toward the nearest neighbor LDD generated surface patch in its vicinity. By default, this surface plane warping is executed with a 2nd order curve fit such that the sensor body-local tangency is gradually moved away from as the surface contour changes shape on its path to meet the adjacent surface plane as measured by the LDD unit atop the closest adjacent region(s). Using a 3rd order equation along every LDD-LDD path will cause more surface bending to be placed into the overall surface contour map but will be limited to 3 curvature reversals in any one LDD-LDD path. Other weighting factors can be used to control the rate at which local plane to local plane transitions are handled including a means to add accelerated bend the farther from the LDD sensor the surface is modeled. These factors can include the physiological characteristics of for example human skin and tissue. The LDD-LDD mesh can at first be just the natural intersections of each plane in whatever geometric form they result in depending on the number of LDD devices on the surface being captured. A minimum of two LDD devices will create a local surface map that is connected along the path from LDD-LDD with a bendable surface between, while all other edges extend 10 centimeters away from the LDD sensor in all other directions. In this way the bendable portion of the surface under and between the LDD-LDD units can flex in a normal direction bending twist along the LDD-LDD axis and distort if either or both LDD devices twist relative to the surface plane. This surface plane twisting of LDD units can occur for example at the corners of the mouth when smiling as the lip moves up and in but also twists into an upward curve. With this software the system can bend a "patch" in LCS relative X and Y directions more and more the further away from the origin of the LDD sensor the surface data is projected. Adjacent patches can be bent so that at desired LDD sensor to sensor distances (as placed in setup) where the projections of each patch meet, the tangencies between adjacent patches are blended to meet. The LDD is at the origin of these larger "Tic Tac" boxes (not to scale as LDD centric "boxes" can be much smaller than a real tic tac box). The patch (brick surface area) is projected from the LDD sensor outward, and the patch bends in two directions to meet up with projections of surface texture data emanating from adjacent tic tac boxes' surface patches.

Figure 21A:
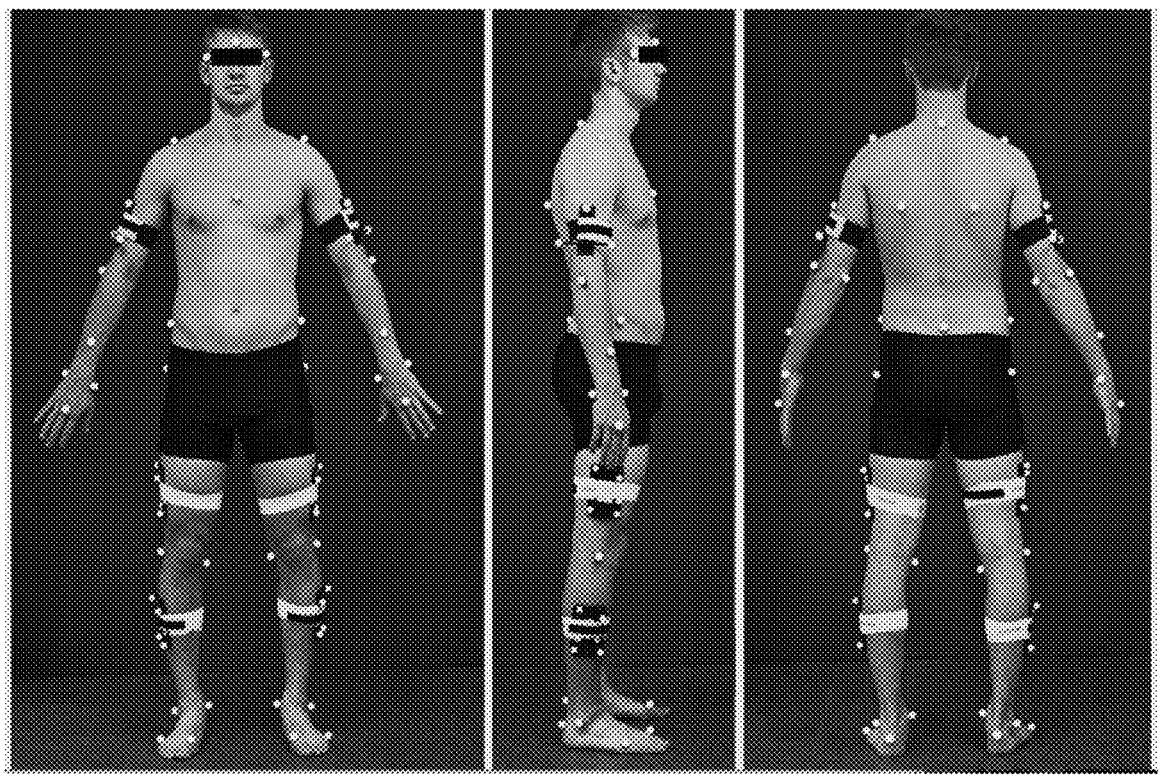
FIGS. 21A-21C are views of a human biomechanical model, according to some embodiments of the present disclosure.
Figure 21B:
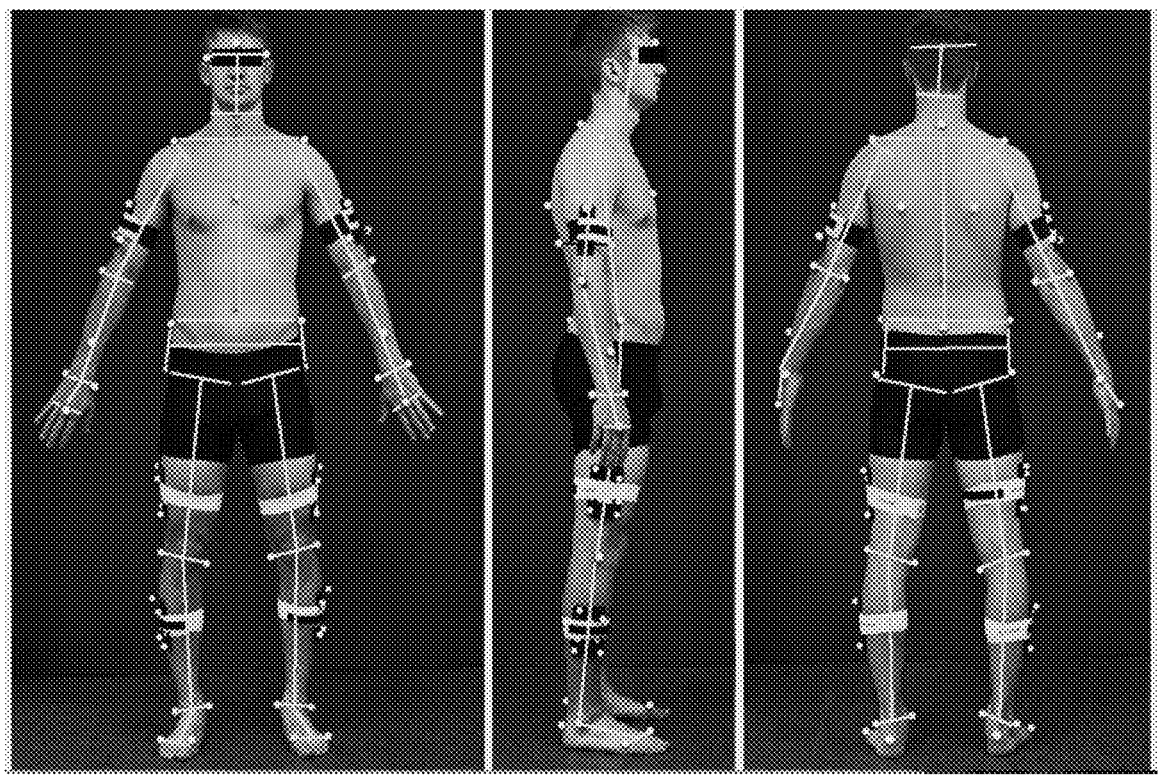
Figure 21C:
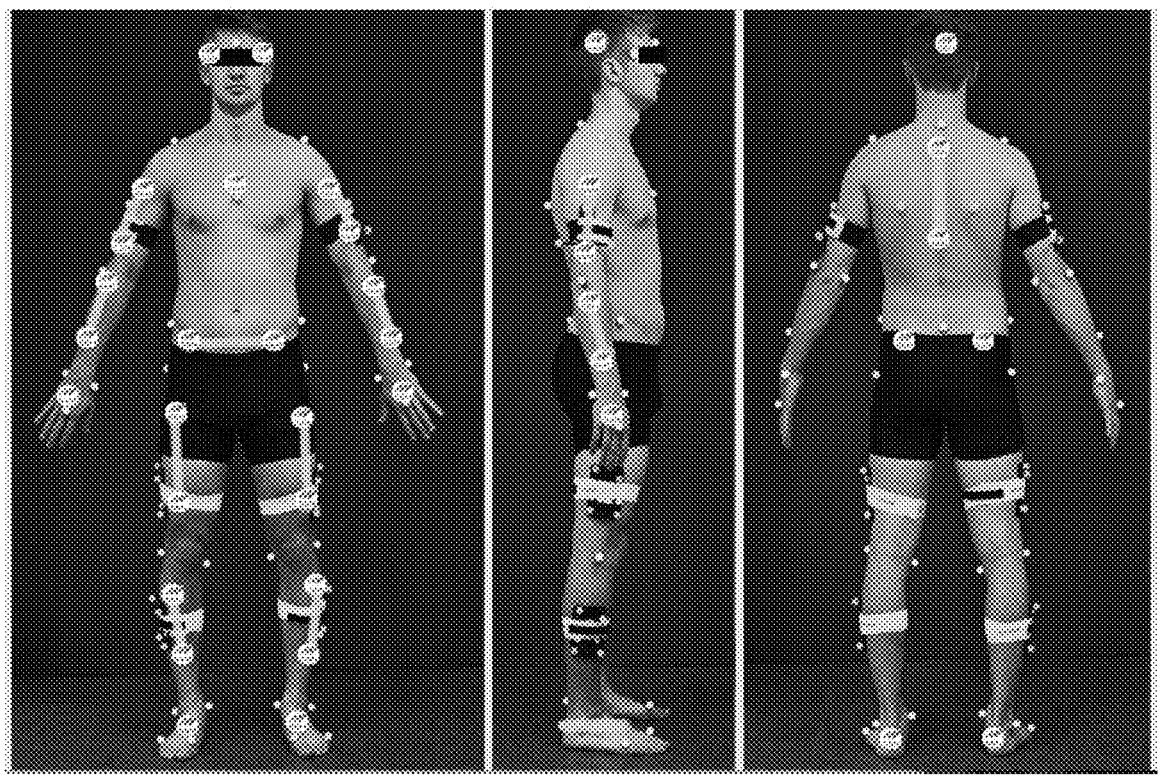

FIGS. 21A-21C are views of a human biomechanical model 2100, according to some embodiments of the present disclosure. In FIG. 21A, connecting the dots can make a linked rigid body model of the human body. Every segment is imagined as a rigid body (thigh, shin for example), see FIG. 21B. Embodiments herein may give the same data with fewer devices. (Note the two LDD chips on the temples with known physical separation for tracking eye balls). Embodiments may leverage known geometrical relationships between LDD devices in the volume, and on the mocap subject. In FIG. 21C, while the calibration markers are still shown (knees, ankles, hips, shoulders, elbows, wrists, etc.), by pairing a device described herein on the body with a video camera, joint centers can be found by computer vision or a stylus wand like that described with respect to FIG. 9 above.

Some embodiments may include underwater LDD sensors mounted with adherable blister housings. The ability to capture a swimming human in water is a specific sport application. The most common way to do this utilizes underwater housing to enable a standard camera-based motion capture system to be mounted underwater. Additionally, blue green lights are used to illuminate retroreflective markers, as this color travels the furthest underwater. In order to function the standard mocap cameras must shoot larger than normal (18 mm diameter) retro-reflective marker spheres that are posted and adhered to the swimmer. These marker spheres cause significant hydrodynamic drag, and only deliver 3D position data. This system described here uses waterproofed underwater blue green lights around the circumferential edge of the pool spaced 20 centimeters under the surface and placed every 50 cm along the edges. Additional lights can be added to the bottom of the pool along the edges or midline of the swimming lane of interest. The athlete is asked to wear a special instrumented suit with a predetermined layout of LDD devices sewn into the garment. The arms being of ¾ length design, and the legs of full-length design. Additional waterproof ports allow the addition of gloves and foot coverings if the biomechanics of each hand and each foot are required. The LDD devices in the garment may be connected to a waist belt measurement collection apparatus with a wireless two-way communication device therein. The form factor of the central device may be as small and low profile as possible. Each LDD location on the garment will have an optically transparent covering and a waterproof permanently wired configuration. The LDD sensor itself will thus be as slim as possible so as not to disturb the hydrodynamics of the swimmer to a noticeable degree. These LDD underwater units may be constructed of pliable rubberized housing and may not exceed 5 mm in thickness, and cover a surface area not to exceed 3×3 centimeters. Together with the optic window and housing, each LDD sensor may weigh less than 8 grams. Since each LDD sensor captures 6DoF data, fewer LDD sensors will be needed to completely describe a swimmer as compared to 3D markers.

To make the sensor readings more discernible in conditions where the walls in an array are casting virtually no shadow, as occurs when the incident light angle to the sensor approaches normal to a plane of light direction detectors, in some embodiments the walls of the light direction detection arrays may have a rectangular top layer of a prescribed width greater than the underlying wall thickness, to physically cause particular identifiable light direction signatures of light and shadow cast on the photodetectors laid on the substrate. FIGS. 22A-22G are views showing the manufacture and use of light direction detection arrays 2200, according to some embodiments of the present disclosure. At normal light direction the T 2210 atop each wall can cast an equal shadow on both sides of the array cell 2220. At light angles slightly away from normal, the T 2210 atop each wall can continue to cast a shadow on both sides of the wall. Based on the height of the wall and the distance the overhanging material on each side of the wall in the top layer projects beyond each face of the wall, a shadow may be cast on each side of the wall until the angle is sufficiently off-normal. Once the light direction has changed to an angle sufficiently larger than the ratio between wall height and overhang size, the "sunny side" photodiode that has a larger photo potential of the two sides of the array cell of the detector may be fully illuminated, while the shadow length on the "shady side" photodiode with a smaller photo potential of the two sides may continue to grow. This jump from partially shaded to fully illuminated as the light angle changes can yield an identifiable inflection that matches a specific angle detection value and is considered a part of how angle is ascertained. Also based on wall height and overhang size, the angle at which the "sunny side" wall face may begin reflecting photons back down to the photodetector on that side, thus forming a signature jump in light intensity captured by the photodiode. The shape of the wall with an overhanging top layer causes lower portions of the wall to be in shadow much like the eve of a roof. It is only at sufficiently high angles away from normal that light begins to strike the wall, first near the base, then progressively higher and higher up the wall, causing more light to be reflected downward onto the photos diode on the plane of the microchip. These jumps in photo potential may create new signatures of light direction conditions that can be used to further disambiguate light direction conditions, and create landmarks that can only occur at specific directions. T-shaped walls also aid in the differentiation between direct and diffuse light striking the microchip. When direct light strikes the LDD with normal and T-shaped walls, the patterns of shadows are measurable and can be interpreted to determine light direction. When diffuse light strikes this same LDD, each photodiode in the pair that make up an array cell will read the same voltages, indicating perfectly normal light direction relative to the microchip surface. When both standard and T-shape walls read equal photoexcitation on their pairs of photodiodes, the light is diffuse and arriving from apparently all directions equally. That there is no signature dip in T-shape wall voltages indicates the LDD is not under arriving light that is nearly or perfectly normal to the microchip, but is under diffuse light. The ability to differential between direct and diffuse light gives the LDD an intelligence to determine if a measured light bearing is coming from a known 3D location or otherwise. Voltage excitations of any photodiode will vary with light intensity but at any relative angle of the photodiode to the light propagation-direction of the light source in a known cosine relationship. Since the LDD understands the arriving light direction angle from normal, it removes the effect of the sensor's relative angle to the light, and thus allow for estimates of the distance between the light and sensor.

Figure 22A:
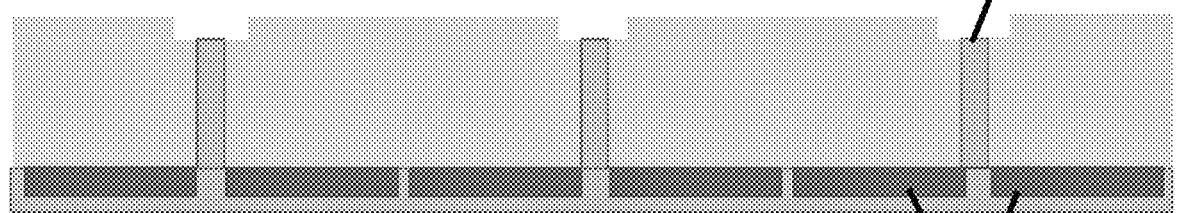
FIGS. 22A-22G are views showing the manufacture and use of light direction detection arrays, according to some embodiments of the present disclosure.
Figure 22B:
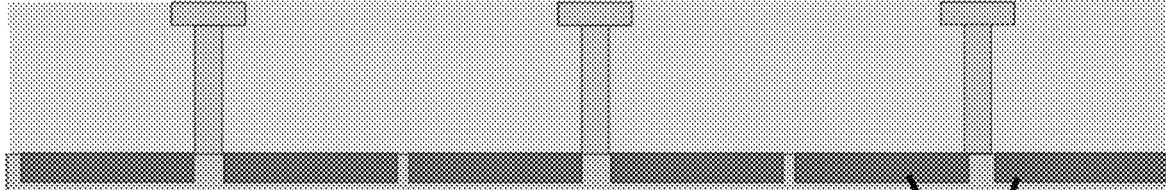
Figure 22C:
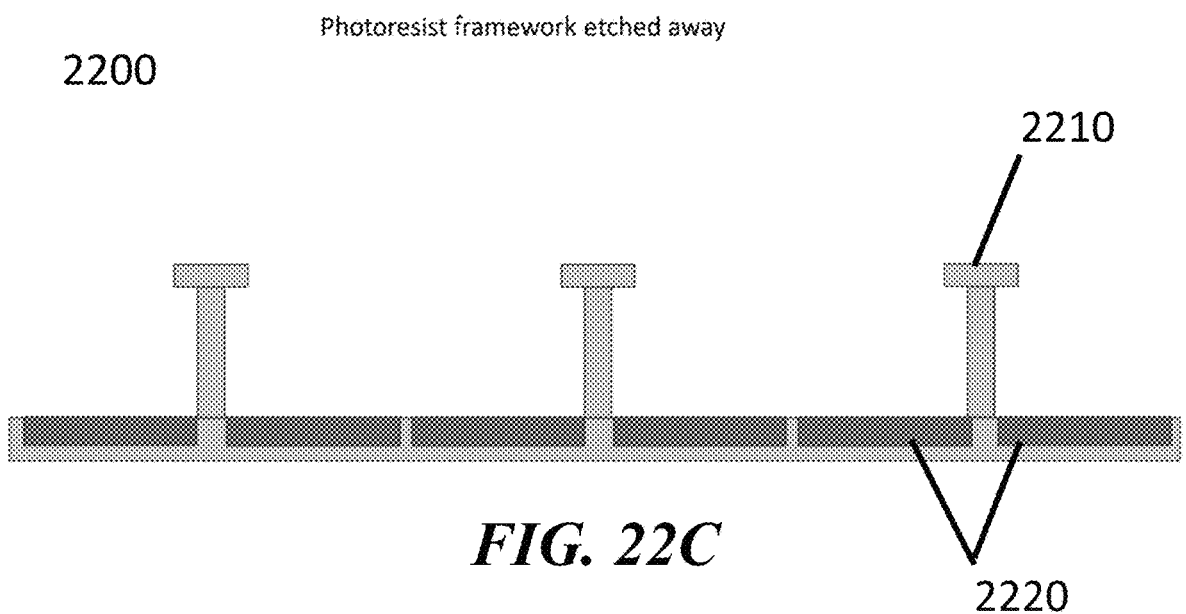
Figure 22D:
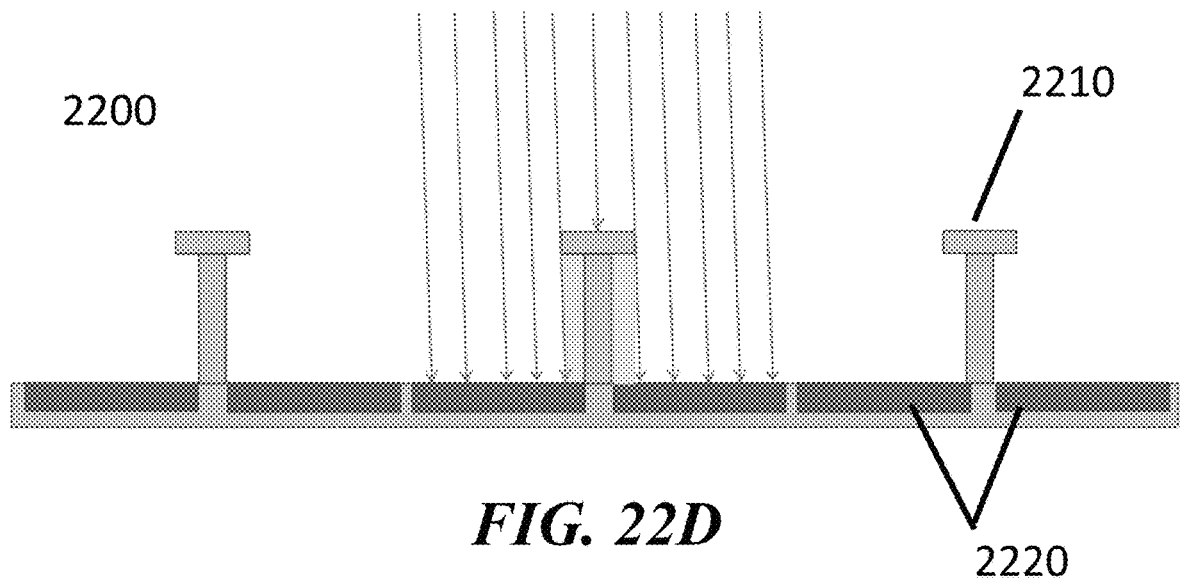
Figure 22E:
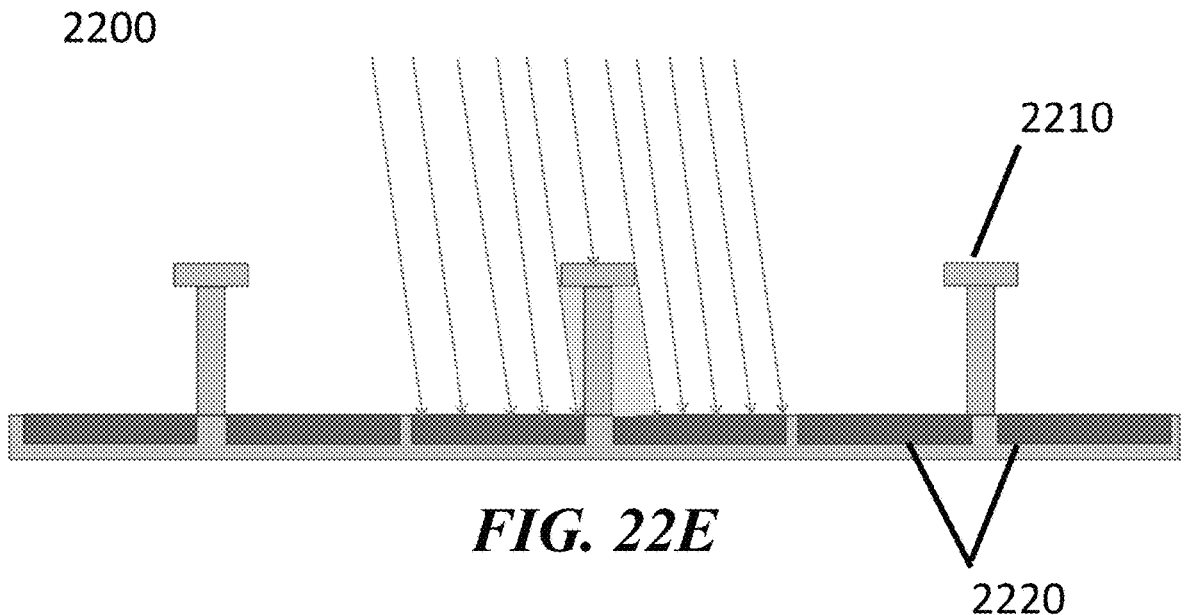
Figure 22F:
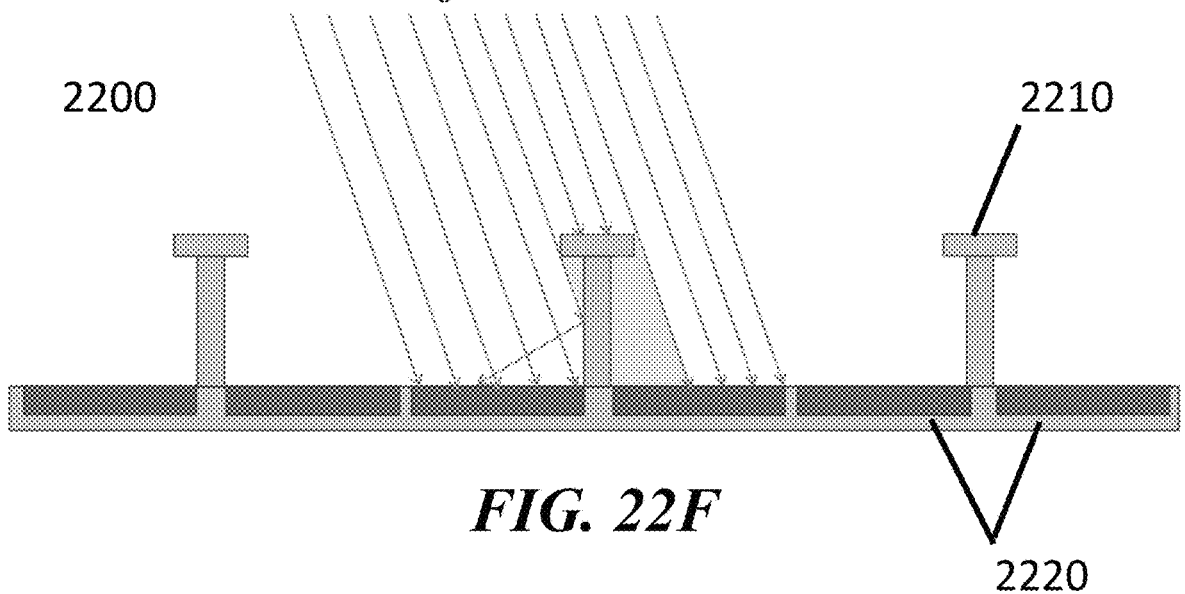
Figure 22G:
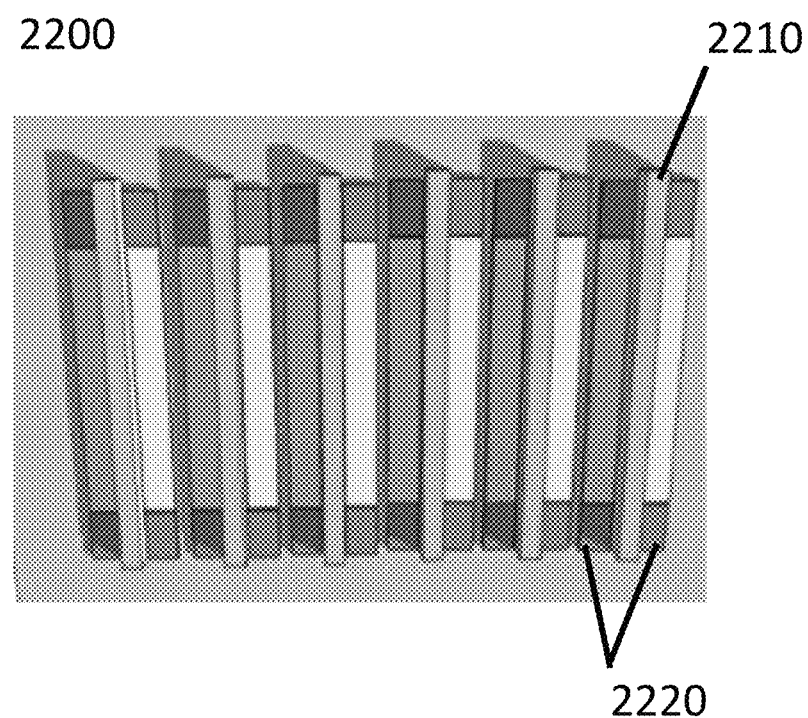

As shown in FIG. 22G in particular, T-shaped corner photodiodes are arranged such that one in each cell is visibly partially lit on the "shady side" when the light strikes the microchip at oblique angles relative to the array main measurement plane. The other shady side photodiode is not lit, and the two on the sunny side are lit. It is this fraction of lit corners from which the measurement comes. With multiple wall/photodiode cells on a microchip, there can be enough current to measure overall. This can be a secondary but perfectly orthogonal measurement from each array, the main measurement may still be the photodiodes 2220 themselves. Each cell in the microchip sensor array can detect light direction in one plane, which is orthogonal to the wall and the pair of photodiodes that make up the cell. The photodiodes 2220 can be shorter in length than the walls with the T 2210 in order to avoid contamination of the principal sensing plane from light that arrives on-chip obliquely. Otherwise as obliquity increases away from the principal sensing plane of the cell, light begins to fall in the regions not blocked by the wall on the "shady side." Oblique light continues to strike the chip surface in these areas, and two paired rectangular or square photodiode cells can be fabricated in these regions between the wall end and the foreshortened principle plane photodiode detectors such that the sensor can make a comparison of the photocurrent being generated at each end of the wall due to arriving light obliquity. These four rectangular or square areas can be connected into a circuit. At 45° obliquity and 45° primary angle, half of the square photodiode at one end is lit, while its mate at the other end of the wall is completely shaded. By this differential in photoexcitation the obliquity of arriving light can be measured. In addition, both rectangular or square photodiodes on the "sunny side" of the wall are completely lit. By comparing the ratio of photoexcitation of the four square photodiodes in each cell a measure of the light direction detection can be afforded in the orthogonal plane to the primary detection plane. Photocurrent expected values can be mapped to the cell for all arriving light angles between normal and the 60° limit of the sensor field of view across all combinations of in-plane and oblique arriving light directions.

Figure 23:
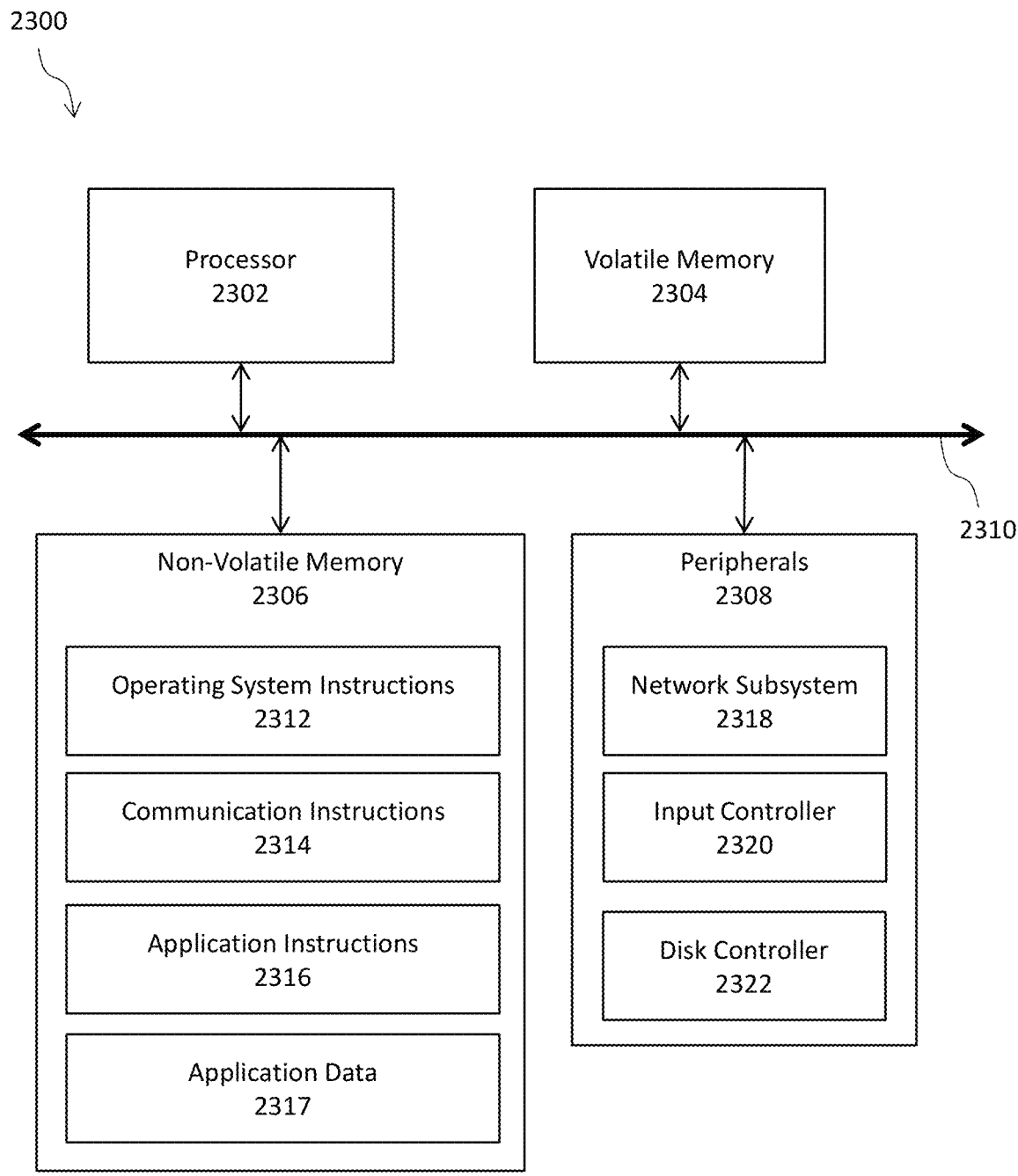
FIG. 23 is a block diagram of an example computer system, according to some embodiments of the present disclosure.

FIG. 23 is a block diagram of an example computer system 2300, according to some embodiments of the present disclosure. The computer system 2300 may be implemented on any electronic device that runs instructions, including without limitation microprocessors, personal computers, servers, smart phones, media players, electronic tablets, game consoles, email devices, etc. In some implementations, the computer system 2300 may include one or more processors 2302, volatile memory 2304, non-volatile memory 2306, or one or more peripherals 2308. These components may be interconnected by one or more computer buses 2310.

A processor 2302 may use any known processor technology, including but not limited to graphics processors and multi-core processors. Suitable processors for the execution of a program of instructions may include, by way of example, both general and special purpose microprocessors, and the sole processor or one of multiple processors or cores, of any kind of computer. A bus 2310 may be any known internal or external bus technology, including but not limited to ISA, EISA, PCI, PCI Express, NuBus, USB, Serial ATA or FireWire. Volatile memory 2304 may include, for example, SDRAM. A processor 2302 may receive instructions and data from a read-only memory or a random access memory or both. The essential elements of a computer may include a processor for executing instructions and one or more memories for storing instructions and data.

Examples of non-volatile memory 2306 may include semiconductor memory devices, such as EPROM, EEPROM, and flash memory devices; magnetic disks such as internal hard disks and removable disks; magneto-optical disks; and CD-ROM and DVD-ROM disks. Non-volatile memory 2306 may store various computer instructions including operating system instructions 2312, communication instructions 2314, application instructions 2316, and application data 2317. Operating system instructions 2312 may include instructions for implementing an operating system (e.g., Mac OS®, Windows®, or Linux). The operating system may be multi-user, multiprocessing, multitasking, multithreading, real-time, and the like. Communication instructions 2314 may include network communications instructions, for example, software for implementing communication protocols, such as TCP/IP, HTTP, Ethernet, telephony, etc. Application instructions 2316 may include instructions for controlling LSUs or motion trackers or for collecting, storing, retrieving or analyzing light- or motion-related data.

Peripherals 2308 may be included within the computer system 2300 or operatively coupled to communicate with the computer system 2300. Peripherals 2308 may include, for example, network interfaces 2318, input devices 2320, storage devices 2322, or display devices. Network interfaces may include Ethernet or Wi-Fi adapters or physical wiring connections. Input devices 2320 may be any known input device technology, including but not limited to a keyboard (including a virtual keyboard), mouse, track ball, or touch-sensitive pad or display. Storage devices 2322 may include mass storage devices for storing data files (e.g., magnetic disks, internal hard disks, removable disks, magneto-optical disks, optical disks).

The computer system may store the 3D coordinate location of each controlled LSU as determined by a calibration procedure, described by example below. In some embodiments, the volume or area encompassed may be scaled from under 1 cubic meter up to or exceeding 5,000 cubic meters or more by adding or removing LSUs. In some embodiments, the LSUs 222 may be affixed on walls ceiling, floors, or may be mounted on free standing poles or tripods.

The present disclosure may be not to be limited in scope by the specific embodiments described herein. Indeed, other various embodiments of and modifications to the present disclosure, in addition to those described herein, may be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art may recognize that its usefulness may be not limited thereto and that the present disclosure may be beneficially implemented in any number of environments for any number of purposes.

What is claimed is:

1. A method for tracking motion comprising:
detecting, at two optically isolated points of a motion tracker device, intensity of a light from a light array comprising a plurality of light sources configured to illuminate in sequence, wherein the optically isolated points are disposed at a distance from one another such that a variation in intensity of light due to shadowing effects from the plurality of light sources is different at the optically isolated points;
generating, by the motion tracker device, a current signal representing a photodiode differential between the two optically isolated points and proportional to the intensity of the light;
generating, by an inertial measurement unit (IMU), an IMU signal representing motion of a body to which the motion tracker device is coupled;
generating a motion signal by combining the current signal and the IMU signal; and
transmitting the motion signal to a computing device.

2. The method of claim 1, wherein the motion tracker device comprises a substrate and at least a first light-direction detector and a second light-direction detector mounted on the substrate at different locations such that an angle of incidence of light from the light array is different on the first and second light-direction detectors.

3. The method of claim 1, further comprising determining, by the computing device, the motion of the motion tracker device with six degrees of freedom based on the current signals transmitted from the first and second light-direction detectors.

4. The method of claim 1, further comprising illuminating the plurality of light sources in the sequence, wherein the plurality of light sources is arranged in a linear arrangement, a rectilinear arrangement, or a T-shaped arrangement and illuminating the plurality of light sources in the sequence comprises individually flashing each of the plurality of light sources sequentially along the linear arrangement, the rectilinear arrangement, or the T-shaped arrangement.

5. The method of claim 1, wherein the plurality of light sources is arranged relative to the substrate such that light output from the plurality of light sources is estimated as a point light source at the motion tracker device.

6. The method of claim 1, wherein the optically isolated points are separated from one another by a T-shaped wall.

7. The method of claim 6, wherein the photodiode differential between the two optically isolated points is affected by a shadow cast by the T-shaped wall.

8. A method for tracking motion comprising:
   detecting, at two optically isolated points of a motion tracker device separated from one another by a T-shaped wall, intensity of a light from a light array comprising a plurality of light sources configured to illuminate in sequence, wherein the optically isolated points are disposed at a distance from one another such that a variation in intensity of light due to shadowing effects from the plurality of light sources is different at the optically isolated points;
   generating, by the motion tracker device, a current signal representing a photodiode differential between the two optically isolated points and proportional to the intensity of the light; and
   transmitting, by the motion tracker device, the current signal to a computing device.

9. The method of claim 8, wherein the photodiode differential between the two optically isolated points is affected by a shadow cast by the T-shaped wall.

10. The method of claim 8, wherein the motion tracker device comprises a substrate and at least a first light-direction detector and a second light-direction detector mounted on the substrate at different locations such that an angle of incidence of light from the light array is different on the first and second light-direction detectors.

11. The method of claim 8, further comprising determining, by the computing device, the motion of the motion tracker device with six degrees of freedom based on the current signals transmitted from the first and second light-direction detectors.

12. The method of claim 8, further comprising illuminating the plurality of light sources in the sequence, wherein the plurality of light sources is arranged in a linear arrangement, a rectilinear arrangement, or a T-shaped arrangement and illuminating the plurality of light sources in the sequence comprises individually flashing each of the plurality of light sources sequentially along the linear arrangement, the rectilinear arrangement, or the T-shaped arrangement.

13. The method of claim 8, wherein the plurality of light sources is arranged relative to the substrate such that light output from the plurality of light sources is estimated as a point light source at the motion tracker device.

14. The method of claim 8, further comprising generating, by the motion tracker device, a motion signal by combining the current signal and an IMU signal representing motion of a body to which the motion tracker device is coupled.

15. A system for tracking motion comprising:
   a light array comprising a plurality of light sources configured to illuminate in sequence; and
   a motion tracker device comprising a substrate, at least one T-shaped wall, and at least one light-direction detector mounted on the substrate and including two optically isolated points on opposite sides of the at least one T-shaped wall arranged such that a variation in intensity of light due to shadowing effects from the plurality of light sources is different at the optically isolated points, the at least one light-direction detector being configured to:
   detect intensity of a light from the light array;
   generate a current signal representing a photodiode differential between the two optically isolated points and proportional to the intensity of the light; and
   transmit the current signal to a computing device.

16. The system of claim 15, wherein the photodiode differential between the two optically isolated points is affected by a shadow cast by the T-shaped wall.

17. The system of claim 15, further comprising the computing device, wherein the computing device is configured to determine the motion of the motion tracker device with six degrees of freedom based on the current signals transmitted from the first and second light-direction detectors.

18. The system of claim 15, wherein the plurality of light sources is arranged in a linear arrangement, a rectilinear arrangement, or a T-shaped arrangement and illuminating the plurality of light sources in the sequence comprises individually flashing each of the plurality of light sources sequentially along the linear arrangement, the rectilinear arrangement, or the T-shaped arrangement.

19. The system of claim 15, wherein the plurality of light sources is arranged relative to the substrate such that light output from the plurality of light sources is estimated as a point light source at the motion tracker device.

20. The system of claim 15, wherein the motion tracker device is further configured to generate a motion signal by combining the current signal and an IMU signal representing motion of a body to which the motion tracker device is coupled.

* * * * *